(12) United States Patent
Vigh et al.

(10) Patent No.: US 9,896,522 B2
(45) Date of Patent: Feb. 20, 2018

(54) SOLID PHASE FLUORESCENCE LABELING REAGENTS AND USES THEREOF

(75) Inventors: Gyula Vigh, Magnolia, TX (US); Roy T. Estrada, III, Houston, TX (US)

(73) Assignee: The Texas A&M University System, College Station, TX (US)

( * ) Notice: Subject to any disclaimer, the term of this patent is extended or adjusted under 35 U.S.C. 154(b) by 635 days.

(21) Appl. No.: 13/819,668

(22) PCT Filed: Aug. 26, 2011

(86) PCT No.: PCT/US2011/049433
§ 371 (c)(1),
(2), (4) Date: May 13, 2013

(87) PCT Pub. No.: WO2012/027717
PCT Pub. Date: Mar. 1, 2012

(65) Prior Publication Data
US 2013/0224870 A1     Aug. 29, 2013

Related U.S. Application Data

(60) Provisional application No. 61/377,777, filed on Aug. 27, 2010.

(51) Int. Cl.
*G01N 33/58* (2006.01)
*C07C 311/39* (2006.01)
(Continued)

(52) U.S. Cl.
CPC ............ *C08F 20/26* (2013.01); *C07C 311/39* (2013.01); *C07D 317/22* (2013.01);
(Continued)

(58) Field of Classification Search
None
See application file for complete search history.

(56) References Cited

U.S. PATENT DOCUMENTS 6,582,917 B1 * 6/2003 Beier ................... B01J 19/0046
435/287.2
2003/0113765 A1   6/2003 Dempcy
(Continued)

FOREIGN PATENT DOCUMENTS

WO          90/05916 A1    5/1990
WO     WO 90/05916    *   5/1990
(Continued)

OTHER PUBLICATIONS

Estrada, III, R. T. "Fluorescent Labeling Reagents Optimized for Capillary Electrophoretic Separations," Dissertation at Texas A&M University, May 2010.*
(Continued)

*Primary Examiner* — Lyle Alexander
*Assistant Examiner* — Michelle Adams
(74) *Attorney, Agent, or Firm* — Christensen O'Connor Johnson Kindness PLLC

(57) ABSTRACT

A solid phase reagent and method for simultaneously capturing and fluorescently labeling an analyte with multiple reactive sites to provide a mono-labeled analyte are disclosed. The reagent can be used in the method and comprises a plurality of analyte-reactive groups tethered to a porous solid phase, wherein each analyte-reactive group is covalently attached to a fluorescent group either directly or indirectly, wherein the distance between adjacent analyte-reactive groups is greater than the gyration radius of a captured analyte; the fluorescent group is covalently attached to a cleavable anchor group either directly or through a first spacer; and the cleavable anchor group is covalently attached to the solid phase either directly or through a second spacer, wherein the solid phase is a porous solid or a porous gel.

43 Claims, 43 Drawing Sheets

DIRECT

(51) Int. Cl.
  *C08F 20/26* (2006.01)
  *C07D 317/22* (2006.01)
  *G01N 33/543* (2006.01)
  *C09B 57/00* (2006.01)
  *G01N 33/68* (2006.01)

(52) U.S. Cl.
  CPC ..... *C09B 57/001* (2013.01); *G01N 33/54306* (2013.01); *G01N 33/54393* (2013.01); *G01N 33/582* (2013.01); *G01N 33/6809* (2013.01); *C07C 2603/50* (2017.05); *Y10T 436/173845* (2015.01)

(56) References Cited

U.S. PATENT DOCUMENTS

| | | |
|---|---|---|
| 2003/0152932 A1 | 8/2003 | Kumar |
| 2005/0272088 A1* | 12/2005 | Cook et al. ............... 435/6 |
| 2005/0274662 A1 | 12/2005 | Xie |
| 2009/0062145 A1 | 3/2009 | Liu |
| 2009/0305410 A1* | 12/2009 | Mao ............... C09B 11/08 435/375 |

FOREIGN PATENT DOCUMENTS

| | | |
|---|---|---|
| WO | 02/093131 A2 | 11/2002 |
| WO | 2005/064336 A1 | 7/2005 |

OTHER PUBLICATIONS

Extended European Search Report mailed Sep. 29, 2016, issued in corresponding Eurpean Application No. 11820757.0, filed Aug. 26, 2011, 10 pages.*

Katritzky, A.R., et al., "Fluorescent Labeling of Peptides on Solid Phase," Organic & Biomolecular Chemistry 6(24):4582-5486, Dec. 2008.*

Krull, I.S., et al., "Solid-Phase Derivatization Reactions for Biomedical Liquid Chromatography," Journal of Chromatography B: Biomedical Applications 659(1-2):19-50, Sep. 1994.*

International Search Report and Written Opinion dated Mar. 27, 2012, issued in corresponding International Application No. PCT/US2011/049433, filed Aug. 26, 2011, 11 pages.

Strickland, D.G., and J.G. Santiago, "In Situ-Polymerized Wicks for Passive Water Management in Proton Exchange Membrane Fuel Cells," Journal of Power Sources 195(6):1667-1675, Mar. 2010.

* cited by examiner

SOLID PHASE FLUORESCENCE LABELING REAGENTS AND USES THEREOF

CROSS-REFERENCE TO RELATED APPLICATION

This application claims the benefit of U.S. Provisional Application No. 61/377,777 filed Aug. 27, 2010, which is incorporated herein by reference in its entirety.

BACKGROUND

Fluorescent labeling can improve the detection sensitivity in capillary electrophoretic (CE) separations down to attomolar concentrations. However, most fluorescent labels are not compatible with CE because their fluorescence properties and charge states are pH-dependent, they are often hydrophobic, and they have a tendency to significantly change the properties of the analytes after labeling. Further, to achieve labeling of analytes in a timely manner, it is necessary to use high concentrations of analyte (e.g., preconcentrated analyte). To address this latter problem, the immobilization of enzymes and derivatizing reagents on solid phases has been studied by several groups. The main motivation for doing these reactions on a solid phase was the observation that reactivity could be increased when the reagents were immobilized compared to when the same reactions were carried out in solution. Unintended multiple labeling of an analyte can still be a problem with this approach, however.

SUMMARY

To address the aforementioned deficiencies, a system has been developed to effect simultaneous immobilization and labeling of an analyte in an analyte-containing solution that permits efficient concentration, labeling and controlled release of the labeled analyte, because the system leads to an increase in the local concentration of an analyte in close proximity to a label-bound analyte-reactive group tethered to a solid phase, wherein the local concentration of the analyte is greater than the analytical concentration of the analyte in the bulk solution prior to contact with the solid phase. Since the tethered analyte-reactive groups are spaced farther apart than the gyration radius of the reacted and thus captured analyte, monolabeling of the analyte occurs following reaction of the analyte-reactive group with the analyte. Further, the labeled analyte can be controllably released into solution through exhaustive quenching of the left-over analyte-reactive groups and subsequent cleavage of a cleavable anchor that had secured the labeled analyte and quenched analyte reactive groups to the solid phase.

While fluorophores will typically be employed as the label, the techniques and embodiments herein are not limited to fluorophores. Any detectable label may be used, such as a UV chromophore. UV chromophores may be useful in the context of labeling carbohydrates, for example, where an amino group is an analyte-reactive group for the reducing end of the carbohydrate. Thus, in some embodiments, another detectable label may be substituted for a fluorophore.

Accordingly, provided herein is a system comprising: (a) a fluorophore; (b) an analyte-reactive group; (c) a cleavable anchor; and (d) a solid phase having a pore, wherein: each fluorophore is covalently attached to a cleavable anchor either directly or through a first spacer; each analyte-reactive group is covalently attached to a fluorophore either directly or indirectly; and each cleavable anchor is covalently attached to the solid phase either directly or through a second spacer, wherein the minimum distance between adjacent analyte-reactive groups is greater than the gyration radius of a captured analyte and the maximum distance between the analyte-reactive group and the analyte, when present, is the maximum dimension of the pore.

Also provided is a fluorophore comprising either of the following moieties:

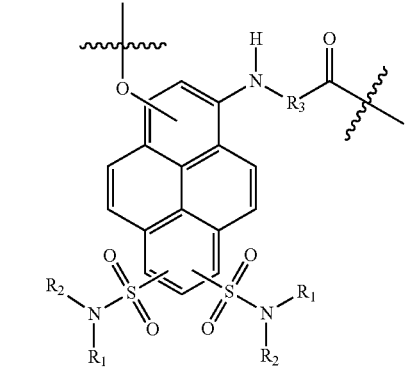

or

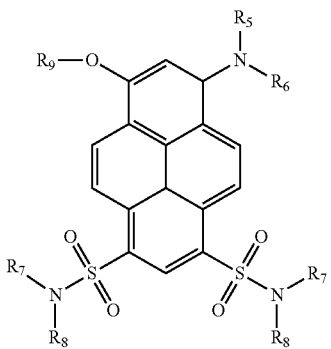

wherein: $R_1$ and $R_2$ are each independently chosen such that the fluorescence of the resulting molecule is pH-independent; and $R_3$ is divalent alkyl$_{C1-12}$ or divalent hetero(backbone)alkyl$_{C1-12}$.

Further provided is a fluorophore having the following formula:

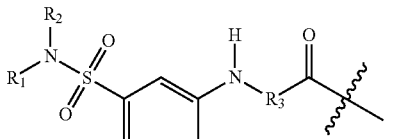

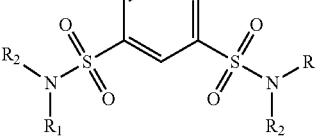

wherein: $R_5$ and $R_6$, independently at each occurrence, is ($—CH_2—$)$_m$, ($—CH_2CH_2O—$)$_n$, or ($—CH_2CH(OH)CH_2O—$)$_p$, wherein one of $R_5$ and $R_6$ independently is connected to an analyte-reactive group and the other comprises a cleavable anchor; and m is an integer ranging from 0 to 12; n is an integer ranging from 1 to 20; and p is an integer ranging from 1 to 20; $R_7$ and $R_8$, independently at each occurrence, is (i) $(-CH_2-)_q$, (ii) $(-CH-)_r$, (iii) $(-CH_2CH_2O-)_s$, or (iii) $(-CH_2CH(OH)CH_2O-)_t$, wherein each of (i), (ii), (iii), and (iv) independently, is connected to a noncharged group, a primary amine, a secondary amine, a tertiary amine, azaaryl, hydroxyaryl, or carboxylic acid, or combination thereof; and wherein: q is an integer ranging from 0 to 12; r is an integer ranging from 0 to 12; s is an integer ranging from 1 to 20; and t is an integer ranging from 1 to 20; and $R_9$ is $(-CH_2-)_t$, (ii) $(-CH-)_u$, $(-CH_2CH_2O-)_v$, or $(-CH_2CH(OH)CH_2O-)_w$, wherein $R_9$ is connected to a noncharged group, a primary amine, a secondary amine, a tertiary amine, a quaternary amine, azaaryl, hydroxyaryl, carboxylic acid, or carboxylate, or combination thereof; and wherein: t is an integer ranging from 0 to 12; u is an integer ranging from 0 to 12; v is an integer ranging from 1 to 20; and w is an integer ranging from 1 to 20.

Further provided is a compound having the following formula:

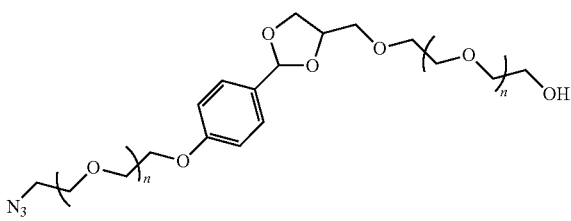

wherein n=1 to 100, independently at each occurrence, or a stereoisomer thereof.

Also provided is a HEMA-based monolith prepared from polymerization of ethylene glycol dimethacrylate (EDMA), HEMA, and methoxyethyl acrylate (MEA).

Further provided is a method of simultaneously immobilizing and labeling an analyte in an analyte-containing solution with a fluorophore, comprising: (a) exposing the analyte to an analyte-reactive group that is covalently attached to a fluorophore either directly or indirectly, wherein the fluorophore is further covalently attached to a cleavable anchor directly or through a first spacer, and the cleavable anchor is covalently attached to a solid phase directly or through a second spacer, and the analyte-reactive groups are spaced farther apart than the gyration radius of a captured analyte; (b) reacting the analyte with the analyte-reactive group, such that the analyte is simultaneously immobilized to the solid phase and labeled with the fluorophore; (c) exhaustively immobilizing the analyte; (d) exhaustively quenching any unreacted analyte-reactive group with a quencher to provide one or more quenched analyte-reactive groups; and (e) cleaving the cleavable anchor to release the labeled analyte and quenched analyte-reactive groups.

Also provided is a method of simultaneously immobilizing and labeling an analyte in an analyte-containing solution with a fluorophore, comprising: (a) contacting an analyte in an analyte-containing solution with the system disclosed herein such that the analyte reacts with the analyte-reactive group to form a covalent bond such that the analyte is simultaneously immobilized and labeled with the fluorophore; (b) exhaustively removing the analyte from the solution by reacting it with the analyte-reactive group; (c) exhaustively quenching any unreacted analyte-reactive group with a quencher to provide one or more quenched analyte-reactive groups; and (d) cleaving the cleavable anchor to release the labeled analyte and the quenched analyte-reactive groups.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 6A: Load; FIG. 6B: Inject.

FIG. 30 and FIG. 30A: Syringe tool for removing the monolith segment from the glass MP tubing mold, wherein FIG. 30A is an expanded view of a portion of FIG. 47.

DETAILED DESCRIPTION

A novel way of implementing a solid phase supported fluorescent labeling reaction has been developed. A distinguishing feature of embodiments herein is that as the analyte is labeled, it is removed from the solution and becomes immobilized on the solid matrix, and it is not released back into the bulk solution until the unused, left-over reactive groups are rendered unreactive by quenching. This process prevents uncontrolled, multiple labeling of analytes with multiple reactive groups. The new solid phase reagent uses a cleavable anchor to connect a fluorophore to a solid phase. The fluorophore has a separate functional group for coupling with the analyte. The cleavable anchor is designed to be stable under the conditions used in fluorophore synthesis yet efficiently cleavable under very mild conditions, ensuring efficient recovery and minimum dilution of the labeled analytes. Methods disclosed herein can therefore achieve simultaneous capture and labeling and efficient release (SCaLER) of analytes. SCaLER can lead to the in situ concentration of analytes that improves detection sensitivity on top of that from the fluorescence labeling. Multiple proportional labeling and mono-labeling of analytes that have multiple possible labeling sites may also be achieved.

The fluorophore can be used not only in the SCaLER construct, but also as a stand alone fluorescent label, either as a trifunctional entity (offering independent, different coupling through the sulfonamide substituents, the alkoxy substituents and the anilinic amino group substituents), or as a difunctional entity (offering independent, different coupling through the alkoxy substituents and the anilinic amino group substituents) and allows for the control of the charge-state of the fluorophore via the substituents of the sulfonamide groups (permanently negatively charged (alkylsulfonate); weakly acidic (alkylcarboxylate); neutral (alkyl or polyalkylene glycol); weakly basic (amino, such as from piperazine); or strong electrolyte cationic (such as from N-trimethyl-N'-methyl-propane diamine)), as desired. It also can be used as a monofunctional entity (offering coupling through either the alkoxy substituent or the anilinic amino group substituents), while using the other groups to adjust the charge-state or hydrophilicity/hydrophobicity as desired.

Figure 43:
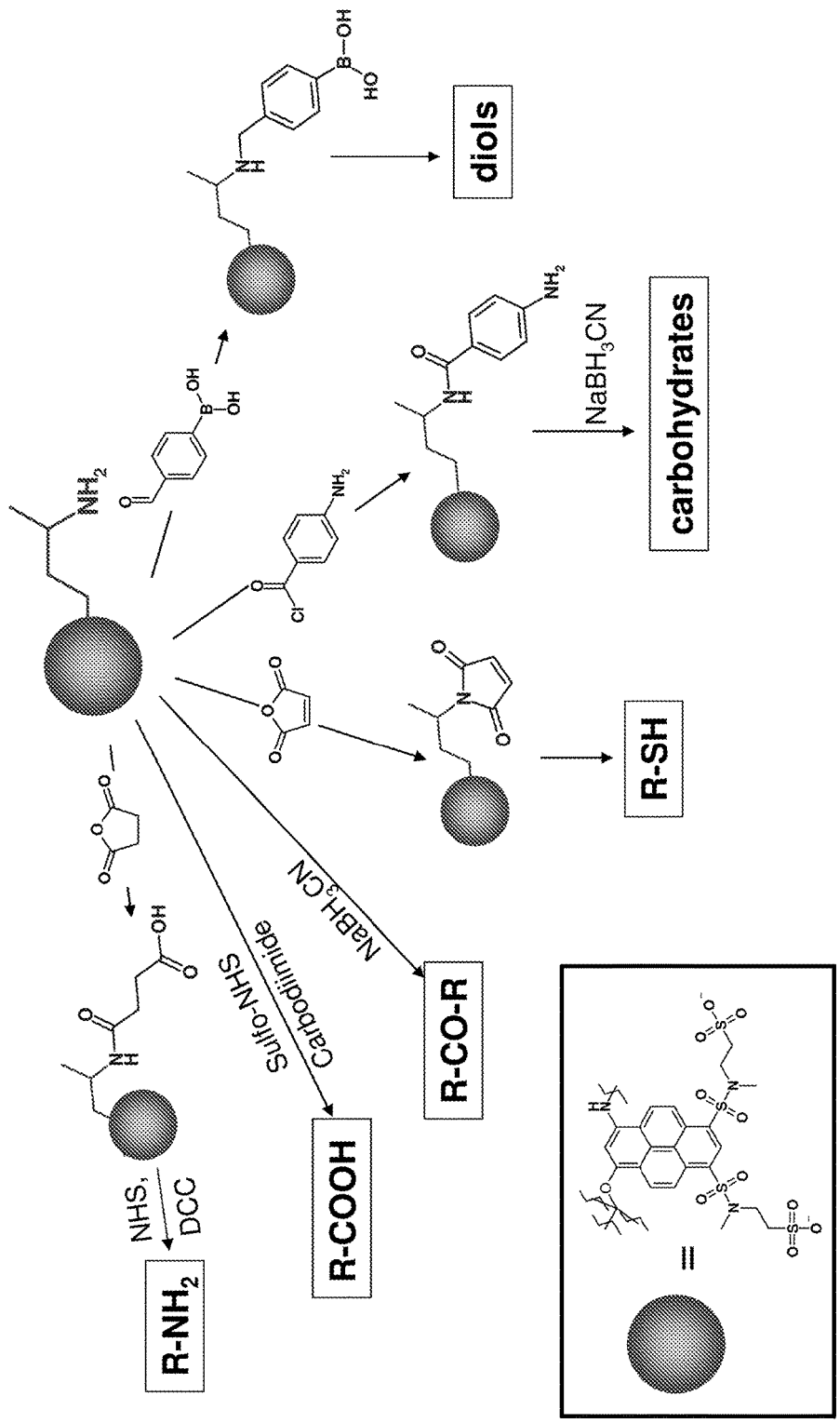
FIG. 43: Exemplary labeling options with a fluorophore of the present invention.

FIG. 43 depicts various fluorescent labeling reaction possibilities using a fluorophore described herein, wherein the fluorophore has been modified such that it presents a —(CH$_2$)—(CH$_2$)—CH(CH$_3$)(NH$_2$) "arm" that may be functionalized in a variety of ways. This arm may be generated from an anilinic 8-amino position of a pyrene-based fluorophore as described herein via a Michael addition reaction between the 8-amino group and the vinyl group of methyl vinyl ketone, followed by reaction with ammonium acetate using reductive amination with sodium cyanoborohydride to obtain the fluorophore with the "arm" as shown. In particular, one-step direct labeling of carbohydrates cleaved from glycoproteins as glycosylamines in basic conditions with such a fluorophore is simpler than present two-step methods involving reductive amination.

Accordingly, provided herein is a system comprising: (a) a fluorophore; (b) an analyte-reactive group; (c) a cleavable anchor; and (d) a solid phase having a pore, wherein: each fluorophore is covalently attached to a cleavable anchor either directly or through a first spacer; each analyte-reactive group is covalently attached to a fluorophore either directly or indirectly; and each cleavable anchor is covalently attached to the solid phase either directly or through a second spacer, wherein the minimum distance between adjacent analyte-reactive groups is greater than the gyration radius of a captured analyte and the maximum distance between the analyte-reactive group and the analyte, when present, is the maximum dimension of the pore. A "captured analyte" refers to an analyte that has reacted with an analyte-reactive group. In some embodiments, the fluorophore is excitable with an argon ion laser at 488 nm. In some embodiments, the fluorescence of the fluorophore is pH-independent between pH 3 and pH 10, inclusive. In some embodiments, the fluorescence of the fluorophore is pH-dependent. The overall charge of the fluorophore may be neutral, anionic, or cationic in the pH range of the experimental conditions employed.

In some embodiments, the experimental conditions employed exhibit a pH ranging from about, at least about, or at most about 1, 2, 3, 4, 5, 6, 7, 8, 9, 10, 11, 12, 13, or 14, or above, or any range derivable there. pH ranges of 1-12, 2-10, and 3-9 are exemplary ranges of experimental conditions.

Any fluorophore herein, whether employed in a system, a method, or as a composition of matter, or other embodiment, may comprise either of the following moieties:

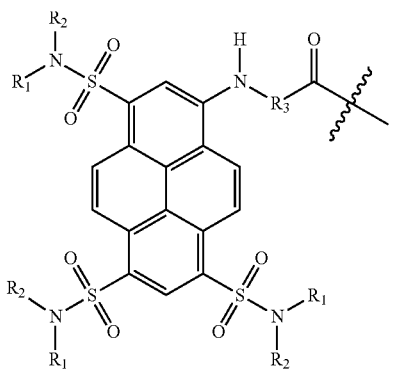

or

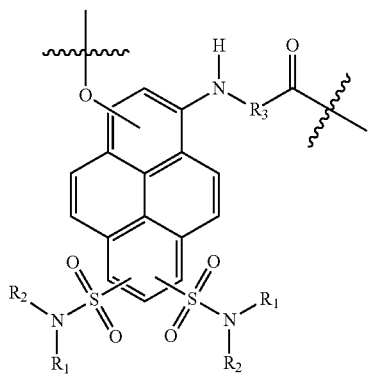

wherein: $R_1$ and $R_2$ are each independently chosen such that the fluorescence of the resulting molecule is pH-independent between pH 3 and pH 10, inclusive; and $R_3$ is divalent alkyl$_{C1-12}$ or divalent hetero(backbone)alkyl$_{C1-12}$. In some embodiments, a fluorophore comprises the following moiety:

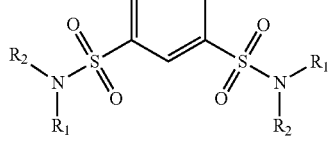

In some embodiments, $R_1$, independently at each occurrence, is hydrogen, alkyl$_{C1-12}$, or hetero(backbone)alkyl$_{C1-12}$, or comprises divalent alkyl$_{C1-12}$ or divalent hetero(backbone)alkyl$_{C1-12}$, wherein at least one hydrogen atom of the alkyl$_{C1-12}$, hetero(backbone)alkyl$_{C1-12}$, divalent alkyl$_{C1-12}$ or divalent hetero(backbone)alkyl$_{C1-12}$ is substituted with a functional group; $R_2$, independently at each occurrence, is hydrogen, alkyl$_{C1-12}$, or hetero(backbone)alkyl$_{C1-12}$, or comprises divalent alkyl$_{C1-12}$ or divalent hetero(backbone)alkyl$_{C1-12}$, wherein at least one hydrogen atom of the alkyl$_{C1-12}$, hetero(backbone)alkyl$_{C1-12}$, divalent alkyl$_{C1-12}$ or divalent hetero(backbone)alkyl$_{C1-12}$ is substituted with a functional group; and $R_3$ is divalent alkyl$_{C1-12}$ or divalent hetero(backbone)alkyl$_{C1-12}$. Any ionic or ionizable moiety present in $R_1$ or $R_2$ of the fluorophore may be four or more sigma bonds removed from the pyrene core. $R_1$ of the fluorophore, independently at each occurrence, may comprise either divalent alkyl$_{C1-12}$ or divalent hetero(backbone)alkyl$_{C1-12}$ and may be connected to an ionic or ionizable moiety in a covalent manner. In some embodiments, an ionic or ionizable moiety is $SO_3^-$, $OSO_3^-$ or $CO_2^-$, or a primary, secondary, tertiary or quaternary amino group. In some embodiments, a fluorophore comprises the following moiety:

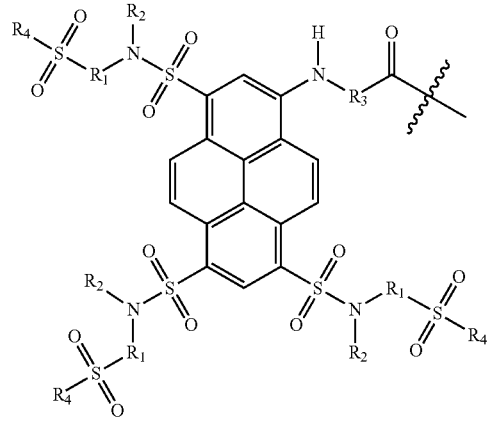

wherein: $R_1$, independently at each occurrence, is divalent alkyl$_{C1-12}$ or divalent hetero(backbone)alkyl$_{C1-12}$; $R_2$, independently at each occurrence, is hydrogen, alkyl$_{C1-12}$, or hetero(backbone)alkyl$_{C1-12}$; $R_3$ is divalent alkyl$_{C1-12}$ or divalent hetero(backbone)alkyl$_{C1-12}$; and $R_4$ is $O^-$ or OH. In some embodiments, $R_3$ comprises one or more oxyethylene groups. In some embodiments, a fluorophore comprises:

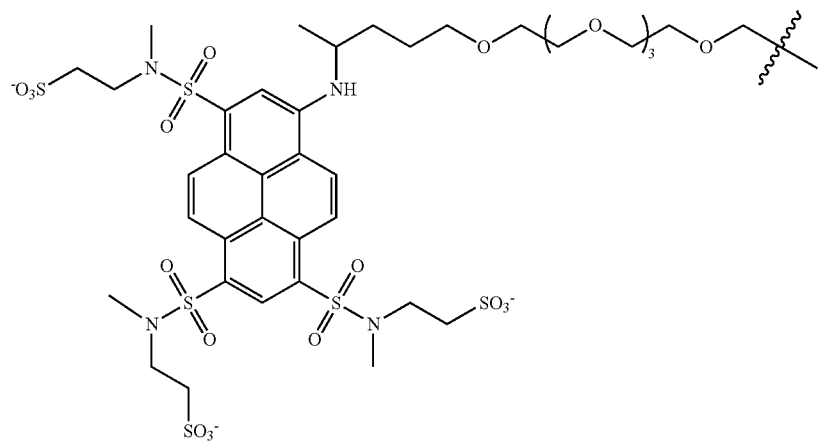

or

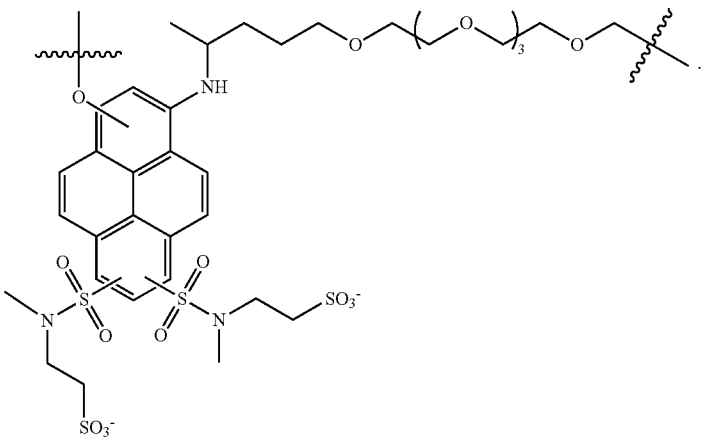

Any fluorophore herein, whether employed in a system, a method, or as a composition of matter, or other embodiment, may comprise the following:

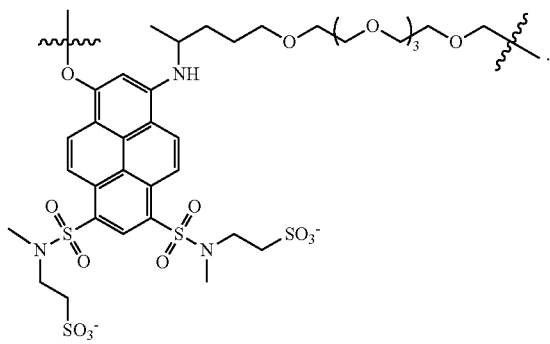

Any fluorophore herein, whether employed in a system, a method, or as a composition of matter, or other embodiment, may comprise the following:

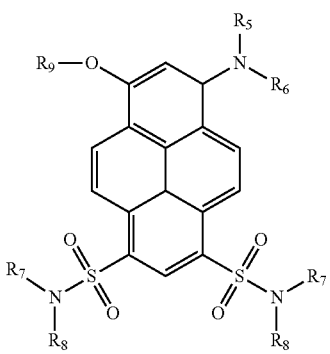

wherein: $R_5$ and $R_6$, independently at each occurrence, is (—$CH_2$—)$_m$, (—$CH_2CH_2O$—)$_n$, or (—$CH_2CH(OH)CH_2O$—)$_p$, wherein one of $R_5$ and $R_6$ independently is connected to an analyte-reactive group and the other comprises a cleavable anchor; and m is an integer ranging from 0 to 12; n is an integer ranging from 1 to 20; and p is an integer ranging from 1 to 20; $R_7$ and $R_8$, independently at each occurrence, is (i) (—$CH_2$—)$_q$, (ii) (—CH—)$_r$, (iii) (—$CH_2CH_2O$—)$_s$, or (iii) (—$CH_2CH(OH)CH_2O$—)$_t$, wherein each of (i), (ii), (iii), and (iv) independently, is connected to a noncharged group, a primary amine, a secondary amine, a tertiary amine, azaaryl, hydroxyaryl, or carboxylic acid, or combination thereof; and wherein: q is an integer ranging from 0 to 12; r is an integer ranging from 0 to 12; s is an integer ranging from 1 to 20; and t is an integer ranging from 1 to 20; and $R_9$ is (—$CH_2$—)$_t$, (ii) (—CH—)$_u$, (—$CH_2CH_2O$—)$_v$, or (—$CH_2CH(OH)CH_2O$—)$_w$, wherein $R_9$ is connected to a noncharged group, a primary amine, a secondary amine, a tertiary amine, a quaternary amine, azaaryl, hydroxyaryl, carboxylic acid, or carboxylate, or combination thereof; and wherein: t is an integer ranging from 0 to 12; u is an integer ranging from 0 to 12; v is an integer ranging from 1 to 20; and w is an integer ranging from 1 to 20. In some embodiments, $R_6$ comprises —$CH_2$—$CH_2$—$CH(CH_3)NH$—. In some embodiments, $R_6$ is —$CH_2$—$CH_2$—$CH(CH_3)NH_2$. An analyte-reactive group may be further defined as an amine-reactive group. In some embodiments, $R_9$ is not hydrogen.

It is particularly contemplated that in any fluorophore described herein, the phenolic oxygen-containing substituent of a pyrene core is not a hydroxyl group. Compare, e.g., hydroxy-containing moieties found in pyrene compounds of WO 2004/027388.

A cleavable anchor is covalently attached to the solid phase either directly or through a spacer. A "cleavable anchor" is stable enough to survive the conditions used for the synthesis of the other components of the reagent (i.e., fluorophore, analyte-reactive group, and any spacers) and the derivatization reactions. A cleavable anchor typically has a hydrolytic half-life greater than 5 min above pH 5. At the same time, the cleavable anchor should be cleavable under mild conditions for facile release of the label-analyte conjugates. As such, a cleavable anchor also typically has a hydrolytic half-life less than 10 hours below pH 5. A cleavable anchor may comprise a photolabile group, although the efficacy of photolytic cleavage can be compromised due to the fact that only those anchors that are accessible by light are cleaved: anchors embedded in pore channels may not be reached by light. A cleavable anchor may comprise a disulfide, although reaction rates of disulfides may not be ideal. A cleavable anchor in any embodiment herein may comprise a 1,3-dioxolane. A cleavable anchor may comprise one of the following moieties:

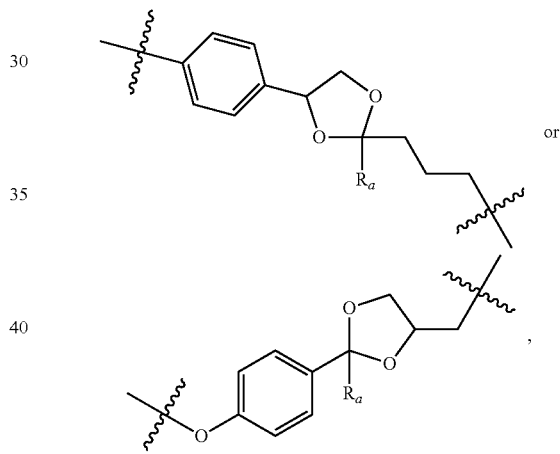

wherein $R_a$ is H or $CH_3$, or stereoisomers thereof, or mixtures thereof. In some embodiments, the cleavable anchor comprises the following moiety:

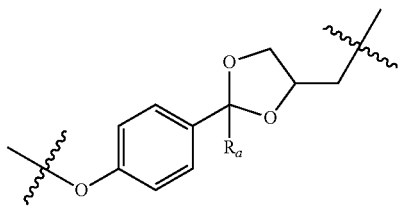

or stereoisomers thereof.

A solid phase in any embodiment herein may be further defined as a particle-based porous solid phase or a monolith solid phase. Non-limiting examples of the former include a crosslinked, porous styrene-based copolymer particle, acrylic acid or substituted acrylic acid-based copolymer particle or polysaccharide-based particle. Common or trade names of such particle-based porous solid phases include Merrifield resins, Tentagel®, Sepharose®, and Sephadex®. In some embodiments, the solid phase is further defined as a monolith solid phase. A monolith solid phase may comprise a functional group selected from the group consisting of epoxy, carboxylic acid, hydroxyl, or combinations thereof. A monolith solid phase may be further defined as a 2-hydroxyethylmethacrylate (HEMA)-based monolith solid phase. In some embodiments, the solid phase is a gel, such as a polyacrylamide where the amide is derived from a hydroxyalkylamine, such as ethanolamine as the active attachment site (analogous to HEMA) and the diluent would be a dialkylamino or —NH2 (analogous to MEA). A solid phase may be a bead.

Any spacer employed herein is a moiety that does not interfere (that is, measurably or detectably interfere) with the function of the fluorophore, analyte-reactive group, cleavable anchor, or solid phase. Spacers may be chosen to increase or preserve the solubility of the components. In some embodiments, the first spacer and/or a second spacer comprises an oligo(oxyethylene) group with a mer-number between 1 and 100. In some embodiments, the mer-number ranges from 2-50. In some embodiments, the mer-number ranges from 3-10.

In some embodiments, the first spacer comprises an oligo(oxyethylene) group with a mer-number between 1 and 100. In some embodiments, the second spacer comprises an oligo(oxyethylene) group with a mer-number between 1 and 100. The analyte-reactive group may be directly covalently attached to the fluorophore. The analyte-reactive group may also be indirectly covalently attached to the fluorophore (that is, through a spacer). Direct and indirect attachment are discussed more herein. In some embodiments, the maximum distance between the analyte and the analyte-reactive group is less than 100 µm. In some embodiments, the maximum distance between the analyte and the analyte-reactive group is less than 10 µm. In some embodiments, the maximum distance between the analyte and the analyte-reactive group is less than 2 µm. In some embodiments, the distance between the analyte-reactive groups is greater than the gyration radius of a captured analyte.

A system may be further defined as:

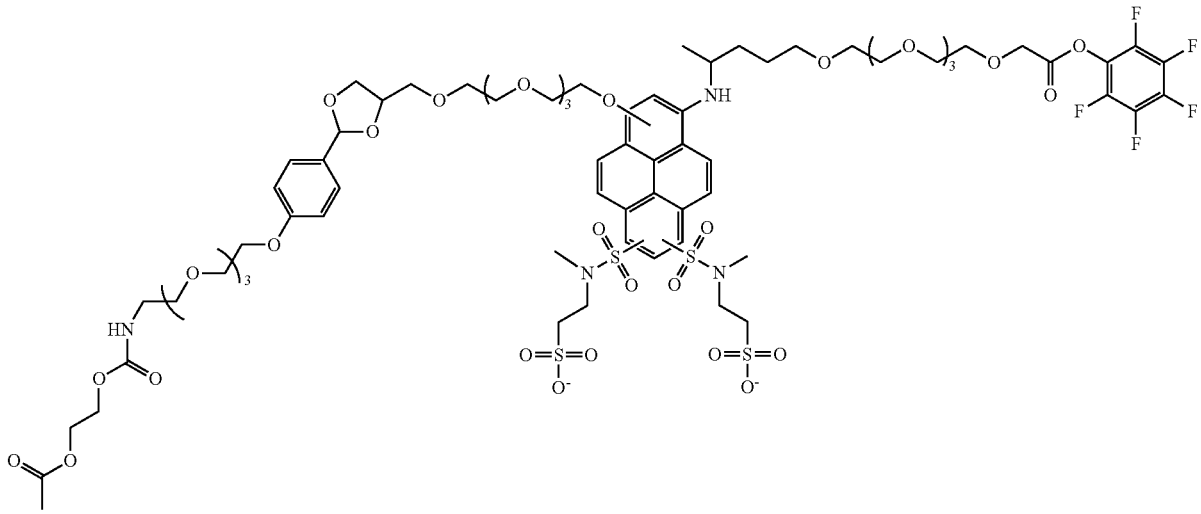

wherein the "Solid Phase" is further defined as HEMA-based monolith solid phase.

Fluorophores described herein do not necessarily need to be employed in a system but may be used for other purposes. A fluorophore employed in any embodiment herein may comprise the following:

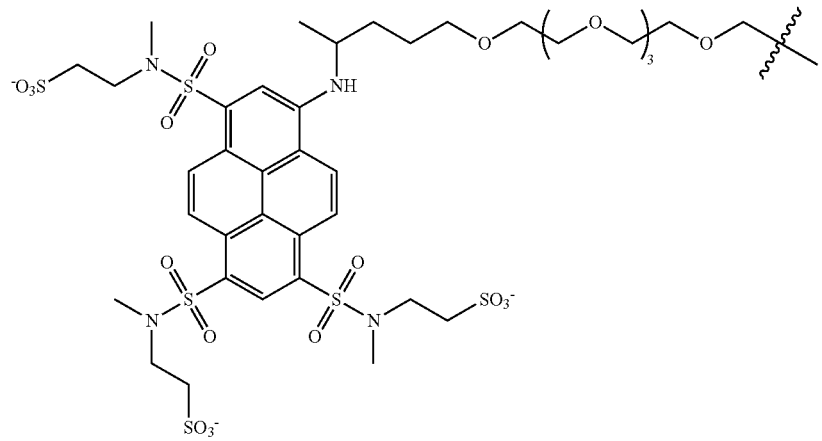

or

-continued
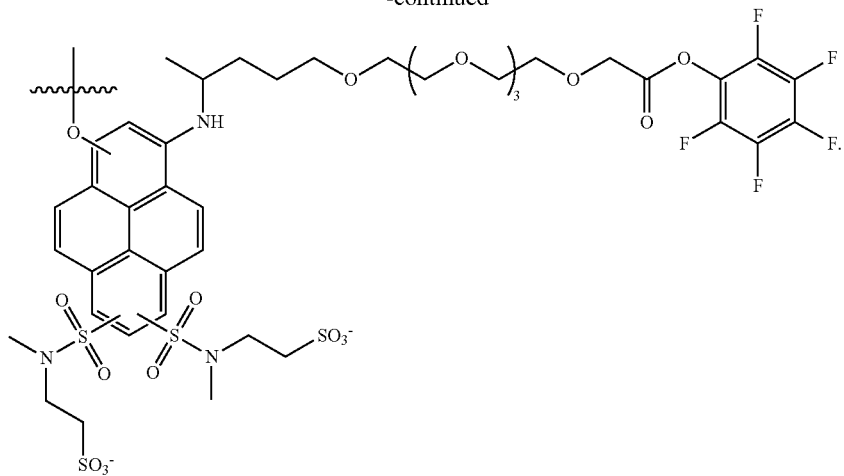
In some embodiments, a fluorophore comprises the following:
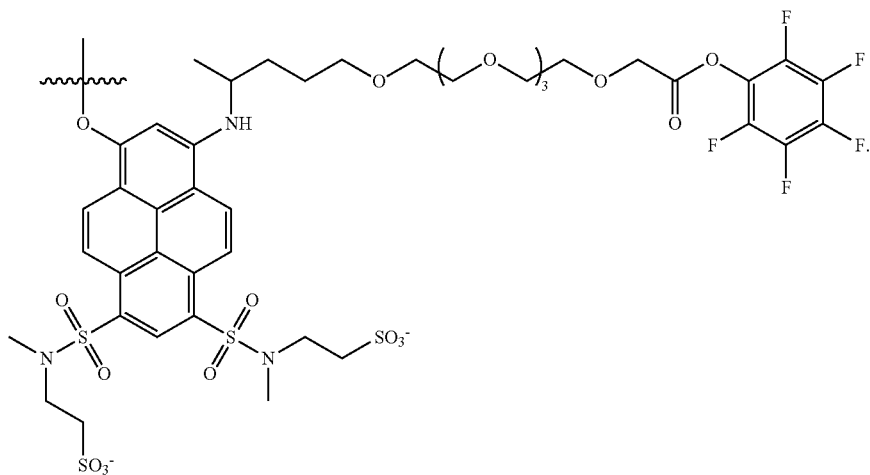
In some embodiments, a fluorophore comprises the following:
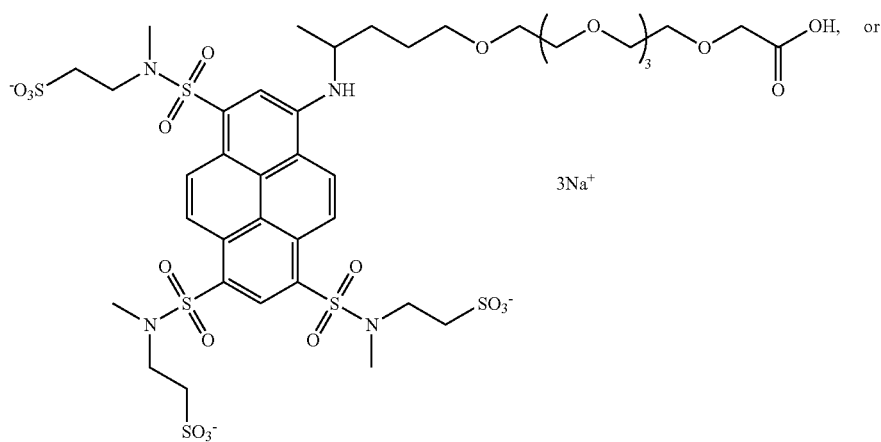

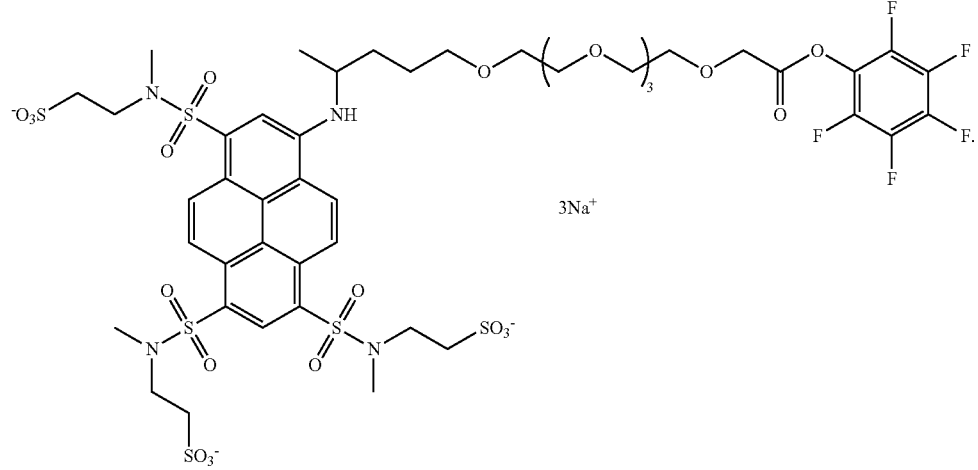

Also provided is a compound having the following formula:

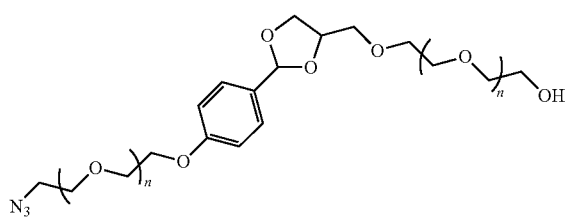

wherein n=1 to 100, independently at each occurrence, and stereoisomers thereof, and mixtures thereof.

Further provided is a HEMA-based monolith prepared from polymerization of ethylene glycol dimethacrylate (EDMA), HEMA, and methoxyethyl acrylate (MEA). In some embodiments, the ratio of HEMA to MEA ranges from 10:0 to 1:9 by weight.

Methods are also provided herein, such as a method of simultaneously immobilizing and labeling an analyte in an analyte-containing solution with a fluorophore, comprising: (a) exposing the analyte to an analyte-reactive group that is covalently attached to a fluorophore either directly or indirectly, wherein the fluorophore is further covalently attached to a cleavable anchor directly or through a first spacer, and the cleavable anchor is covalently attached to a solid phase directly or through a second spacer, and the analyte-reactive groups are spaced farther apart than the gyration radius of a captured analyte; (b) reacting the analyte with the analyte-reactive group, such that the analyte is simultaneously immobilized to the solid phase and labeled with the fluorophore; (c) exhaustively immobilizing the analyte; (d) exhaustively quenching any unreacted analyte-reactive group with a quencher to provide one or more quenched analyte-reactive groups; and (e) cleaving the cleavable anchor to release the labeled analyte and quenched analyte-reactive groups. In some embodiments, the analyte-containing solution is subjected to electrophoresis or pressure. In some embodiments, the local concentration of analyte at the site of reaction with the analyte-reactive group is increased relative to the bulk solution concentration due to the fact that the volume of liquid in a solid phase pore is much smaller than in the bulk solution, thus, for the same total number of molecules the local concentration n the pore becomes higher once the analyte enters the pore.

Also provided is a method of simultaneously immobilizing and labeling an analyte in an analyte-containing solution with a fluorophore, comprising: (a) contacting an analyte in an analyte-containing solution with the system disclosed herein such that the analyte reacts with the analyte-reactive group to form a covalent bond such that the analyte is simultaneously immobilized and labeled with the fluorophore; (b) exhaustively removing the analyte from the solution by reacting it with the analyte-reactive group; (c) exhaustively quenching any unreacted analyte-reactive group with a quencher to provide one or more quenched analyte-reactive groups; and (d) cleaving the cleavable anchor to release the labeled analyte and the quenched analyte-reactive groups. In any method described herein, the cleavable anchor may be cleaved with a cleaving agent to release the labeled analyte. A method described herein may further comprise detecting the released labeled analyte. Detection may take place using any appropriate method known to those of skill in the art, such as capillary electrophoresis, high performance liquid chromatography, absorption or fluorescence spectroscopy, or mass spectrometry, or a combination thereof, for example. A method may further comprise isolating the released labeled analyte.

With respect to exhaustive immobilizing and exhaustive quenching, this does not necessarily mean that all analyte has been immobilized and all unreacted analyte-reactive groups have been quenched. A skilled artisan will be able to determine when exhaustive immobilization and quenching have occurred. For example, one may test the flow-through eluent for the presence of the unbound analyte. Once the detection level reaches an acceptable level, the method may be ceased such that exhaustive immobilizing and exhaustive quenching has been achieved. The acceptable level will be left to the researcher to determine. A method may further comprise recirculating the analyte-containing solution to maximize immobilization and labeling of the analyte, and may further comprise multiple additions of quencher. Exhaustive quenching facilitates avoidance of multilabeling of analyte, which is a problem with other techniques.

Persons of skill in the art will be familiar with suitable analytes. In some embodiments, an analyte is a small organic molecule having a molecular weight of less than 1000 g/mol. In some embodiments, the small organic molecule has a molecular weight of at least about, at most about, or about 10, 35, 50, 75, 100, 150, 200, 250, 300, 350, 400, 450, 500, 600, 700, 800, 900, or 1000 g/mol, or any range derivable therein. In some embodiments, an analyte is a small organic molecule having a molecular weight of greater than 1000 g/mol. An analyte may comprise a peptide, a protein, a carbohydrate, an oligonucleotide, an DNA, or an RNA, or a combination thereof. In some embodiments, an analyte comprises an amino group that reacts with the analyte-reactive group.

As used herein, an "analyte-reactive group" refers to a leaving group. As used herein, the term "leaving group" refers to a group readily displaceable by a nucleophile, such as an amine, an alcohol, or a thiol nucleophile. Such leaving groups are well known and include carboxylates, N-hydroxysuccinimidate, N-hydroxybenzotriazolate, triflates, tosylates, mesylates, alkoxy, thioalkoxy and the like. In some embodiments, an analyte-reactive group is further defined as one that is introduced under basic conditions (that is, a pH above 7) and does not hydrolyze under the experimental conditions employed, such as pentafluorophenylate. In some embodiments, the analyte-reactive group is an amine-reactive group.

Typically, the molar amount of analyte-reactive groups will exceed the molar amount of analyte. In this way, the opportunity for capturing all available analyte will be maximized as the analyte-containing solution traverses the pores of the solid phase. In some embodiments, the molar amount of analyte-reactive groups is at least 100 times that of the molar amount of analyte. In some embodiments, the molar amount of analyte-reactive groups is at least 1,000 times that of the molar amount of analyte. In some embodiments, the molar amount of analyte-reactive groups is at least 10,000 times that of the molar amount of analyte.

The phrase "wherein the fluorescence of the fluorophore is pH-independent" refers to a fluorophore that does not exhibit a change in the excitation maximum or emission maximum wavelengths or quantum yield over the pH range of the experimental conditions employed, or exhibits a maximum change of less than 10% in either or both of them. In some embodiments, the maximum change is less than 5%. In some embodiments, the maximum change is less than 2%. In some embodiments, the maximum change is less than 1%. In some embodiments, the pH range is from pH 3 to pH 10, inclusive. It is noted that at very low pH values (e.g., pH 1), sulfonamides or anilinic amino groups may become protonated; further, sulfonamide hydrolysis typically occurs at pH values above 11.

The term "alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms and includes straight-chain alkyl, branched-chain alkyl, cycloalkyl (alicyclic), and cyclic alkyl. In some embodiments, alkyls of 1-12 carbon atoms are contemplated. In some embodiments, lower alkyls are contemplated. The term "lower alkyl" refers to alkyls of 1-6 carbon atoms (that is, 1, 2, 3, 4, 5 or 6 carbon atoms). The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, and cyclohexyl, are all non-limiting examples of alkyl groups. Divalent alkyl groups are also contemplated.

The term "hetero(backbone)alkyl" refers to a monoradical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, and S, and each heteroatom is located in the backbone of the moiety and each heteroatom is flanked on either side by carbon atoms. For example, a hetero(backbone)alkyl$_{C_1-C_{12}}$ has 1 to 12 carbon atoms and at least one heteroatom in the backbone. A hetero(backbone)alkyl group may be optionally substituted by one or more hydroxy substituents, such as polyvinyl alcohol moieties (—CH$_2$CH(OH)—). That is, the term "hetero(backbone)alkyl" refers to hydroxy-substituted moieties as well as unsubstituted. The following groups are non-limiting examples of hetero(backbone)alkyl groups: —CH$_2$OCH$_3$, —CH$_2$CH$_2$OCH$_2$CH$_3$, —CH$_2$NHCH$_3$, —CH$_2$CH$_2$NHCH$_2$CH$_3$, and —CH$_2$CH$_2$OCH$_2$CH$_2$NHCH$_2$CH$_2$OCH$_2$CH$_3$. Divalent hetero(backbone)alkyl groups are also contemplated, wherein this term also encompasses optional hydroxy substitution.

"Aryl" refers to an aromatic monocyclic or multicyclic hydrocarbon ring system consisting only of hydrogen and carbon and containing from 6 to 19 carbon atoms. Aryl groups include, but are not limited to groups such as phenyl, naphthyl, anthryl, phenanthryl, indenyl, and fluorenyl. As used herein, "azaaryl" refers to an aryl group wherein at least one ring atom is a nitrogen.

As used herein, an "ionizable group" is a group that may form an ion. Non-limiting examples of ionizable groups include —NH$_2$, —NH$_3$, —SO$_3$H, —OSO$_3$H, —CO$_2$H and —OH.

The term "functional group" generally refers to how persons of skill in the art classify chemically reactive groups. Examples of functional groups include hydroxyl, amine, ammonium, amide, carboxylic acid, carbonyl, etc. In some embodiments, the functional group is not a thiol.

As used herein, the term "leaving group" generally refers to a group readily displaceable by a nucleophile, such as an amine, an alcohol, or a thiol nucleophile. Such leaving groups are well known and include carboxylates, N-hydroxysuccinimide, N-hydroxybenzotriazole, triflates, tosylates, mesylates, alkoxy, thioalkoxy and the like.

As used herein, a "peptide" refers to two or more amino acids joined together by an amide bond. In certain embodiments, peptides comprise up to or include 50 amino acids. Peptides may be linear or cyclic. Peptides may be α, β, γ, δ, or higher, or mixed. Naturally-occurring and unnatural peptides are contemplated. Peptides may comprise any mixture of amino acids, such as comprising any combination of D, L, α, β, γ, δ or higher amino acids.

The term "carbohydrate" refers to any compound containing at least one carbohydrate subunit. The carbohydrate subunit may be a monosaccharide (such as glucose or fructose), a disaccharide (such as sucrose, maltose, lactose or trehalose) or an oligo- or polysaccharide (i.e., molecules having a degree of polymerization of 3-10 and of more than 10, respectively). The oligo- and polysaccharides may be of any type, including, but not limited to: galactans, (galacto)-mannans, furanofructans and xylans; α-glucans such as pullulan, starch, starch components (i.e., amylose or amylopectin) or starch derivatives (e.g., dextrins, maltodextrins or cyclodextrins); β-glucans such as cellulose or chitin; fructans such as inulin; natural or artificial gums such as xanthan, guar, gum arabic, agar, carrageenan, and the like.

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

As used herein, "a" or "an" may mean one or more, unless clearly indicated otherwise.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

As an alternative to or in addition to "comprising," any embodiment herein may recite "consisting of:" The transitional phrase "consisting of" excludes any element, step, or ingredient not specified in the claim.

It is specifically contemplated that any limitation discussed with respect to one embodiment of the invention may apply to any other embodiment of the invention. Furthermore, any composition of the invention may be used in any method or system of the invention, and any method of the invention may be used to produce or to utilize any composition of the invention.

Overview of One Embodiment

Solid phase fluorescent labeling reagents (SPR) were designed to simultaneously capture and label analytes, permit the quenching of the unused reactive groups and then efficiently release the labeled-analytes and quenched reactive groups under mild conditions (SCaLER). The SCaLER SPR design incorporates four separate parts: a fluorophore, an amine-reactive group (although other analyte-reactive groups may be employed), a cleavable anchor and a solid phase. In one embodiment, the fluorescent, pyrene-based label 33 was used as the starting fluorophore (see Example 1). A cleavable group was optimized for stability to sustain the harsh conditions during synthesis and conditions during the labeling reaction, and cleavability for ease of release of the labeled analytes under mild conditions. A cleavable group based on an alkoxy-benzyl-dioxolane scaffold was shown to be stable under alkaline conditions but was easily cleaved under very mild conditions ($t_{1/2}$ of 1 min at pH 3.1). Tetra(ethylene glycol) spacers were used in between different parts of the SPR to maintain high aqueous solubility and local hydrophilicity.

The attachment of the cleavable anchor to the fluorophore was accomplished through a facile exchange of one of the sulfonamide groups on the pyrene ring with an alkoxy group. The exchange also improved the fluorescence properties of the fluorophore. The new fluorophore was found to have pH-independent fluorescence properties and charge state as well.

An acrylate-based monolithic solid phase was developed as the SPR solid support. The monolith was prepared by photoinitiated free radical polymerization of HEMA, EDMA and MEA monomers with AIBN as catalyst and 1-octanol as porogen. The monomers were chosen to provide hydroxyl groups on the solid surface to which the cleavable anchor of the fluorophore could be attached. The reactivity of the hydroxyl group as a coupling functionality is orthogonal to that of the amine-reactive group of the fluorophore. The immobilization of the completely assembled fluorophore was proven to not affect the cleavability of the cleavable anchor, thus allowing analyte recovery under mild conditions. Moreover, due to the use of the monolithic solid phase, the elution of the cleaved off sample can be done with a minimal amount of solvent.

Using a pipette tip cartridge format of SCaLER SPR, different amines were derivatized and analyzed by CE-LIF (capillary electrophoresis laser induced fluorescence). A four orders of magnitude wide linear dynamic range was found for 1-methylpiperazine. Without the use of preconcentration or special techniques to improve detection sensitivity, an LOQ (limit of quantification) of 10 nM was achieved. These experiments proved that SCaLER SPR can be used to derivatize and detect analytes at low concentrations even without preconcentration.

Sections I and II below offer further description of this embodiment as well as the Examples.

I. Exemplary Design of a Pyrene-Based Fluorophore

An amine-reactive fluorophore that can be effectively utilized in the SDS-CGE (sodium dodecylsulfate—capillary gel electrophoresis) separation of proteins and other macromolecules will have the following characteristics: (i) it will be negatively charged to minimize non-selective interactions with the SDS-protein complex, (ii) it will be highly soluble in aqueous background electrolytes to minimize protein aggregation even at high label-to-protein ratios, (iii) it will have fluorescence properties that do not vary with the pH of the background electrolyte between pH 3 and 10, and (iv) it will have a charge state that is pH-independent in a particular pH range. It would also be desirable for the fluorophore to have (v) an $\lambda_{max}^{ex}$ that is compatible with the commonly used 488 nm argon ion laser assuring general utility in CE.

8-Aminopyrene-1,3,6-trisulfonic acid (APTS), shown below as a trisodium salt, has been extensively used to fluorescently label carbohydrates:

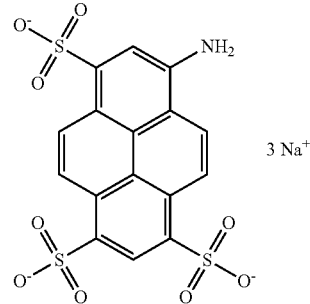

8-Aminopyrene-1,3,6-trisulfonic acid (trisodium salt)
$\lambda_{max}^{ex}$ = 420 nm; $\lambda_{max}^{em}$ = 500 nm The $\lambda_{max}^{ex}$ of APTS around 420 nm. Consequently, excitation at 488 nm makes use of only about 4% of its maximum absorbance. For APTS, altering the electron withdrawing/donating capability of the sulfonic acid and amino groups may provide incremental bathochromic shifts to $\lambda_{max}^{ex}$. Thus, the inventors had the general objective for the development of a pyrene-based fluorophore, which was to build a complete fluorescent labeling reagent (fluorophore, tether and reactive group) out of the APTS core structure while preserving its desirable properties, as stated above, and simultaneously shifting its $\lambda_{max}^{ex}$ towards 488 nm. A general structure of an envisioned amine-reactive label is shown below:

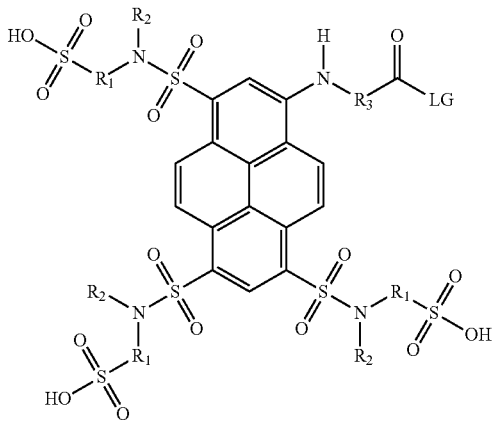

wherein $R_2$ is H or alkyl, and $R_1$ and $R_3$ are alkyl or heteroalkyl groups. LG is a leaving group. The sulfonic acid groups can be sulfonamidated with an aminoalkanesulfonic acid to maintain multiple anionic charges on the molecule. A reactive arm terminated with a carboxylic acid, which is later on activated, can be used for attachment to the anilinic amino group.

There are some considerations to be made in choosing the aminoalkanesulfonic acid to be used for the sulfonamidation reaction. The amino group can either be a primary or a secondary amino group. The selection will determine the form of the sulfonamide nitrogen and may have an effect on the fluorescence properties of the molecule. The sulfonic acid group can come either unprotected or protected. Because these have very contrasting polarities (i.e., one is ionic and the other is not) they may have important implications on the way the fluorophore will be prepared and purified.

There are a number of available aminoalkanesulfonic acids that are suitable for sulfonamidation of APTS, including taurine, N-methyltaurine, homotaurine, 2-cyclohexylamino-1-ethanesulfonic acid (CHES) and 3-cyclohexylamino-1-propanesulfonic acid (CAPS). Taurine and N-methyltaurine are more attractive because these have less hydrophobic alkyl parts than the others and have amino groups that are less sterically hindered in the sulfonamidation reaction. Example 1 below describes various sulfonamidation preparations.

Alkylation of weak anilinic amines can be a challenge but can be accomplished by several methods. Two of the most accessible ones are alkylation by Michael addition and reductive amination. A large number of catalyzed or promoted Michael addition (Firouzabadi, H., Iranpoor, N., Jafarpour, M., Ghaderi, A., *Journal of Molecular Catalysis A: Chemical* 2006, 252, 150-155; Amore, K. M., Leadbeater, N. E., Miller, T. A., Schmink, J. R., *Tetrahedron Letters* 2006, 47, 8583-8586; Hussenether, T., Hubner, H., Gmeiner, P., Troschutz, R., *Bioorganic & Medicinal Chemistry* 2004, 12, 2625-2637; Surendra, K., Krishnaveni, N. S., Sridhar, R., Rao, K. R., *Tetrahedron Letters* 2006, 47, 2125-2127) and reductive amination (Huang, D. W., Jiang, H., Nakanishi, K., Usherwood, P. N. R., *Tetrahedron* 1997, 53, 12391-12404; Verardo, G., Giumanini, A. G., Strazzolini, P., Poiana, M., *Synthesis-Stuttgart* 1993, 121-125; Amokhtari, M., Andersen, K., Ibazizene, M., Dhilly, M., et al., *Nuclear Medicine and Biology* 1998, 25, 517-522; Obrien, P. M., Sliskovic, D. R., Blankley, C. J., Roth, B. D., et al., *Journal of Medicinal Chemistry* 1994, 37, 1810-1822; McLaughlin, M., Palucki, M., Davies, I. W., *Organic Letters* 2006, 8, 3307-3310) reactions have been reported but only a few used aniline substrates that are comparable in nucleophilicity to tris sulfonamide 21 (see Example 1). For both types of reactions acid catalysis appears to be most effective (Hussenether, T., Hubner, H., Gmeiner, P., Troschutz, R., *Bioorganic & Medicinal Chemistry* 2004, 12, 2625-2637; Verardo, G., Giumanini, A. G., Strazzolini, P., Poiana, M., *Synthesis-Stuttgart* 1993, 121-125) and was thus tried for alkylation of amine 21. Reductive amination in the presence of drying agents such as molecular sieves and sodium sulfate has been explored by several groups (Huang, D. W., Jiang, H., Nakanishi, K., Usherwood, P. N. R., *Tetrahedron* 1997, 53, 12391-12404; Amokhtari, M., Andersen, K., Ibazizene, M., Dhilly, M., et al., *Nuclear Medicine and Biology* 1998, 25, 517-522; Obrien, P. M., Sliskovic, D. R., Blankley, C. J., Roth, B. D., et al., *Journal of Medicinal Chemistry* 1994, 37, 1810-1822). This principle was also used in the development of a more efficient way to reductively alkylate amine 21. It was also important to determine from the alkylation tests whether $\lambda_{max}^{ex}$ shifted towards 488 nm.

For the purposes of analyzing protein analytes, a hydrophilic heteroalkyl chain as a tether to the fluorophore was preferred over a hydrophobic alkyl chain in order to reduce the likelihood of nonspecific interactions with the hydrophobic parts of proteins which may have significant and unpredictable effects on fluorescence. A poly(ethylene glycol)-based tether/reactive arm was designed that could be installed using the optimized alkylation method. Example 2 below describes various alkylation reactions of the anilinic amino group.

Neopentyl sulfonate esters are extremely stable and require relatively harsh conditions to deprotect. Roberts et al. reported the cleavage of a neopentyl arylsulfonate ester by heating with tetramethylammonium chloride in DMF at 160° C. for 16 hours (Roberts, J. C., Gao, H., Gopalsamy, A., Kongsjahju, A., Patch, R. J., *Tetrahedron Letters* 1997, 38, 355-358). Adamczyk and others deprotected dyes having alkylsulfonate esters by refluxing them in 1N HCl for 4 to 8 hours (Adamczyk, M., Chen, Y. Y., Mattingly, P. G., Pan, Y., Rege, S., *Journal of Organic Chemistry* 1998, 63, 5636-5639). These and other conditions were investigated to minimize the formation of byproducts.

Once deprotected, the fluorophore becomes tetra-anionic making purification by conventional methods difficult. The use of preparative liquid chromatography was a practical choice but different aspects of the separation had to be carefully considered. For instance, reverse phase liquid chromatography will not be suitable because the very polar compound will not have enough retention in the nonpolar stationary phase. The use of ion pairing agents may be help but these will be difficult to remove from the target later on. Hydrophilic interaction liquid chromatography (HILIC) is another mode of liquid chromatography that is orthogonal to reverse phase in its selectivity and is usually used to separate polar compounds having little retention in the latter. However, there are only a few reports on the use of HILIC for semi-preparative or preparative fractionations (Lindner, H., Sarg, B., Helliger, W., *Journal of Chromatography A* 1997, 782, 55-62; Lindner, H., Sarg, B., Meraner, C., Helliger, W., *Journal of Chromatography A* 1996, 743, 137-144; Zhang, H., Guo, Z. M., Li, W., Feng, J. T., et al., *Journal of Separation Science* 2009, 32, 526-535) and none of these has a highly ionic compound as their target.

A new approach for the semi-preparative HILIC purification of the tetra-anionic target compound was developed with the aim of maximizing throughput without sacrificing the integrity of the separation. Example 3 below describes procedures for the removal of the neopentyl protecting group and purification of a sulfonic acid by preparative hydrophilic interaction liquid chromatography (Prep HILIC). Spectral properties of a sulfonic acid (compound 33) are presented in Example 4. The fluorophore was derived from APTS and its development consisted of red-shifting its $\lambda_{max}^{ex}$ from 425 nm to 502 nm through sulfonamidation and alkylation. Fluorescence labeling tests with the pyrene-based label are described in Example 5.

The fluorescent label has pH-independent electrophoretic mobilities and fluorescence properties with a fluorescence quantum yield that is typical if not better ($\Phi_{fluor33}$ 0.76) than those observed for other pyrene derivatives. The new reagent was successfully applied for the labeling of small diamines affording low nanomolar limits of detection (LODs) (corresponding to low attomol amounts) in their CE-LIF separations at different pH values. The new fluorophore has also been successfully used to label proteins for SDS-CGE-LIF analysis. Labeling did not affect the migration behavior of the labeled proteins as shown by their linear log MW vs $T_m$ plots. The calculated LODs for the labeled proteins were in the low ng/mL or low nanomolar range.

The LIF detection system used for the above experiments had a detection band pass filter centered at 520 nm. At this wavelength only about 5% of the maximum emission of the fluorophore can be harnessed. This means that the limits of detection attained can still be improved by an order of magnitude by using a detection filter centered at around 560 nm.

II. Development of SCaLER (Simultaneous Capture and Labeling, Efficient Release)

Figure 18:
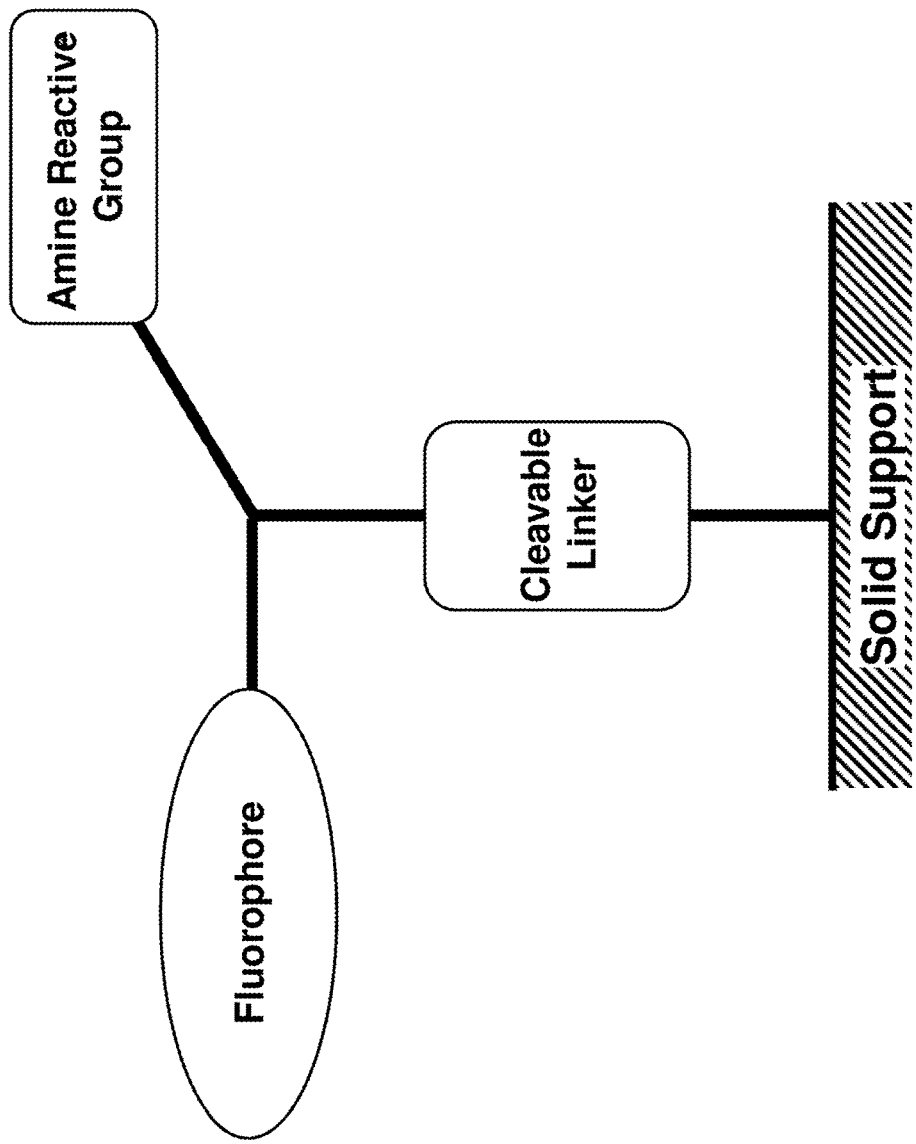
FIG. 18: A cartoon of the proposed general structure of SCaLER (Simultaneous Capture and Labeling, Efficient Release) solid phase reagent (SPR).

A cartoon of a proposed general structure of the SCaLER fluorescent labeling SPR is shown in FIG. 18. A distinguishing feature of this SPR is that the core fluorophore is covalently anchored to the solid support and, in addition, has an independent analyte-reactive moiety. The SCaLER system immobilizes the analyte the moment it is derivatized or labeled (thus, the name, Simultaneous Capture and Labeling). The anchor of the label is designed in such a manner that it can be severed efficiently under relatively mild conditions to release the label-analyte conjugate (thus, Efficient Release). To facilitate efficient removal of the labeled analyte from the spent solid phase, the latter should be designed with minimized mass transfer limitations. The fluorophore and the analyte-reactive group are typically separated by a tether to minimize the effects of the analyte on the fluorescence of the fluorophore.

Figure 19:
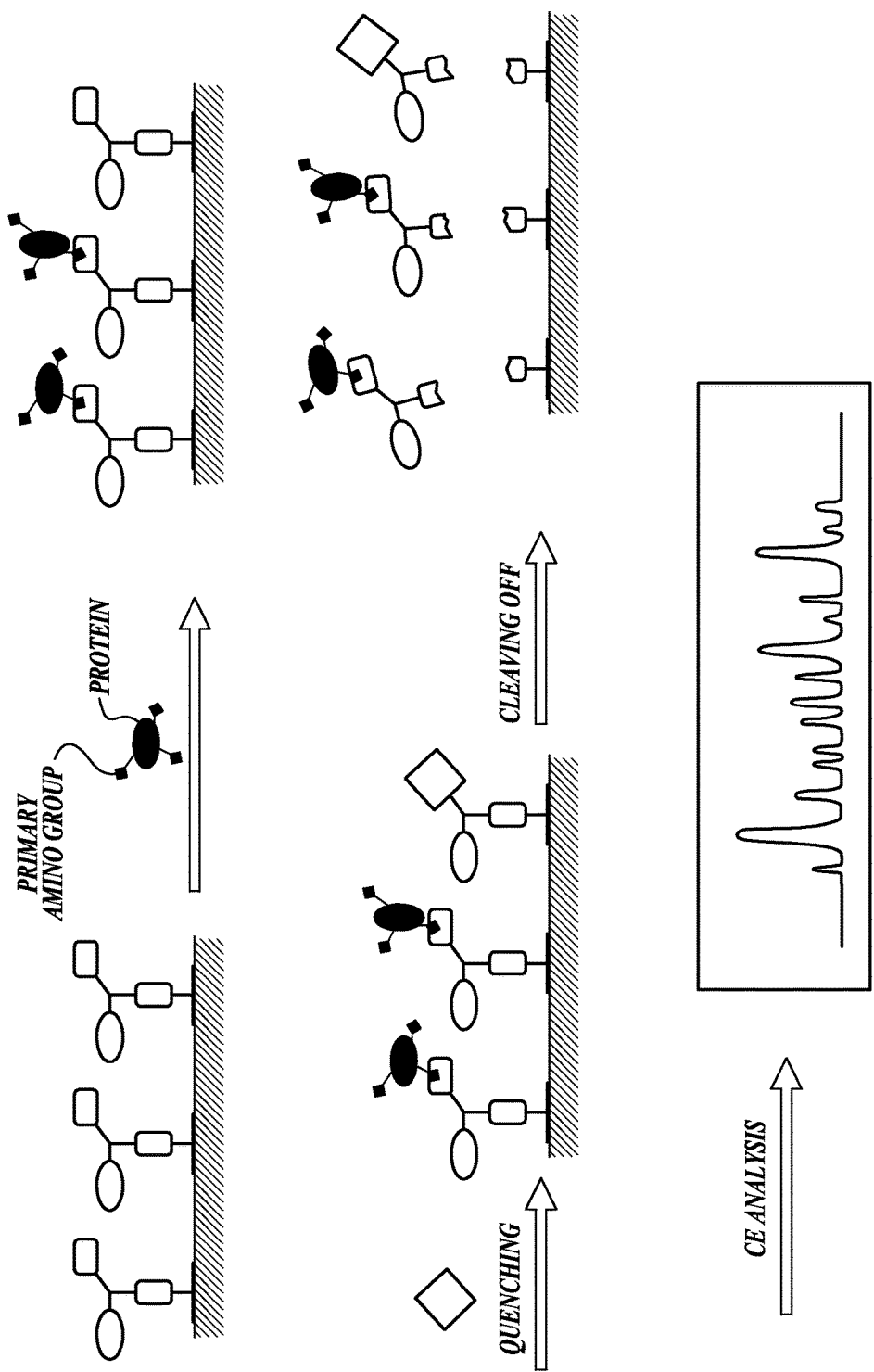
FIG. 19: General schematic of the derivatization process using SCaLER SPR for the fluorescent labeling of proteins.

The general schematic of the labeling process with SCaLER is presented in FIG. 19. It starts by eluting the analyte (a protein is shown in the figure but the analyte can be any molecule with a derivatizable group) through the solid phase to allow contact with the reactive group that is attached to the label. The sample solution can be recirculated over the SPR in order to maximize conversion of the analyte to the labeled derivative. After this, the unreacted label is exhaustively reacted with a quenching compound. A cleaving agent is subsequently flushed through the solid phase to break the cleavable tether. The label-analyte conjugate is released into the bulk solution only at this point and can then be directly analyzed by CE or by any other applicable analytical method such as HPLC with UV, fluorescence or MS detection. The labeled analyte can also be used for biological studies after removal of the cleaving agent.

A benefit when using methods described herein is the in situ preconcentration of dilute samples during derivatization. Large sample volumes with low analyte concentrations can be eluted through the solid phase. During labeling, the analytes are pulled out of the bulk solution into the much smaller volume of the solid support. In this manner, the effective concentration of the analyte is increased versus its concentration in the bulk solution without a traditional preconcentration step. After labeling, the tagged analytes can be cleaved off with a small volume of cleaving agent, thus providing analyte enrichment.

Moreover, the simultaneous capture and labeling system makes the degree of analyte labeling more reproducible. When analytes having multiple reactive sites, such as proteins, are derivatized in solution phase, the number of labels incorporated into the analyte depends on the concentration of both reactants and the reaction time. Both the relative concentrations and the reaction time determine the probability of a collision between the analyte—whether unlabeled or already labeled—and a reactive label initiating the derivatization reaction. In the SCaLER design, once the analyte is labeled and captured on the solid surface, it is prevented from reacting with a label from another part of the reaction space. The average number of labels attached to a certain analyte will now solely depend on the spacing of the reactive labels on the solid support surface and the number of active sites and their spacing on the analyte.

If the distance between the anchored reactive labels is smaller than the gyration radius of the captured analyte, multiple labels will be attached to the analyte, but this will occur in a proportional manner. In this scenario, the incorporation rate depends on the number of active sites on the analyte vis-à-vis the surface density of the reactive label which will be the same for all SPR batches. Proportional multiple labeling in solution phase can only occur if labeling is done exhaustively, that is, when a large excess of the labeling reagent is used which does not have to be the case when using SCaLER. For fluorescence detection, proportional multiple labeling using the SPR can give better quantitation than exhaustive derivatization because the former minimizes the possibility of fluorescence self quenching. This is expected to result in reproducible response factors that are proportional to the number of reactive groups on the analyte.

However, if the distance between the anchored reactive labels (spacing) is larger than the gyration radius of the captured analytes, only mono-labeling can occur, no matter how many reactive sites the analytes carry. In solution phase, mono-labeling can only be achieved when the label-to-protein ratio is low (Unlu, M., Morgan, M. E., Minden, J. S., *Electrophoresis* 1997, 18, 2071-2077): this, unavoidably, leads to labeling only of a small portion of the analyte population. Because the number of reactive labels is limited, their attachment to—and distribution between—the analytes will depend on the respective reactivities of the latter. When done in the SPR format, mono-labeling is achieved even with an excess of reactive labels thereby producing an analyte population that is completely mono-labeled. Mono-labeling can be of high utility when pure standards of the analytes are not available to establish calibration curves, because mono-labeling leads to relative response factors that are more indicative of the molar ratios of the analytes. For proteins and other biological compounds, mono-labeling can be useful in biological assays because this can give optimal quantitation with a minimal change of the analyte structure.

The cleavable anchor should be stable enough to survive the conditions used for the synthesis of the SPR and the derivatization reactions. At the same time, it should be cleavable under mild conditions for facile release of the label-analyte conjugates. Example 6 below describes the preparation of exemplary cleavable linkers. The cleavable part of the anchor can be made from a number of existing cleavable linkers. Holmes (Holmes, C. P., Jones, D. G., Journal of Organic Chemistry 1995, 60, 2318-2319; Holmes, C. P., Journal of Organic Chemistry 1997, 62, 2370-2380) reported that photolabile o-nitrobenzyl linkers could be rapidly cleaved by irradiating with 365 nm UV light. Gupta and others (Kumar, P., Mahajan, S., Gupta, K. C., Journal of Organic Chemistry 2004, 69, 6482-6485; Kumar, P., Bose, N. K., Gupta, K. C., Tetrahedron Letters 1991, 32, 967-970) developed reusable solid phase supports for oligonucleotide synthesis that relied on a disulfide moiety for the cleavable group. The disulfide bond was broken using a reducing agent such as dithiothreitol.

Although not for a solid phase application, a 1,3-dioxolane-based cleavable linker was described by Jaeger and coworkers who designed surfactants for use as vesicular media for reaction catalysis Jaeger, D. A., Chou, P. K., Bolikal, D., Ok, D., et al., Journal of the American Chemical Society 1988, 110, 5123-5129; Jaeger, D. A., Jamrozik, J., Golich, T. G., Clennan, M. W., Mohebalian, J., Journal of the American Chemical Society 1989, 111, 3001-3006). One of these dioxolanes could be cleaved under relatively mild acidic conditions. The linker had a half life of 56 minutes in a pH 3 aqueous buffer. ALS, standing for acid-labile surfactant, is another 1,3-dioxolane-containing surfactant that was developed by Waters Corporation as an alternative to SDS in gel electrophoresis. Several groups reported improved MS analysis of tryptic peptides when ALS was used instead of SDS due to improved peptide recovery after decomposition of the surfactant at low pH (Ross, A. R. S., Lee, P. J., Smith, D. L., Langridge, J. I., et al., Proteomics 2002, 2, 928-936; Zeller, M., Brown, E., Bouvier, E., Konig, S., J Biomol Tech 2002, 13, 1-4; Konig, S., Schmidt, O., Rose, K., Thanos, S., et al., Electrophoresis 2003, 24, 751-756; Yu, Y. Q., Gilar, M., Lee, P. J., Bouvier, E. S. P., Gebler, J. C., Analytical Chemistry 2003, 75, 6023-6028). Yu and others reported a half life of 8 minutes for ALS at pH 2 (Yu, Y. Q., Gilar, M., Lee, P. J., Bouvier, E. S. P., Gebler, J. C., Analytical Chemistry 2003, 75, 6023-6028).

A 1,3-dioxolane group was chosen as a cleavable group of the SCaLER SPR due to its simplicity, ease of cleavage and its stability in both neutral and basic solutions. However, since the half life of 1,3-dioxolanes reported by Jaeger is rather long, the effect of the substituents around the dioxolane ring on the hydrolysis rate was looked into to find structures with desirable rates of cleavage. The synthesis of the cleavable anchor was designed to allow its insertion between the solid surface and the fluorophore. Spacers consisting of well-defined oligo(ethylene glycol) chains were used to maximize hydrophilicity of the construct.

Figure 20B:
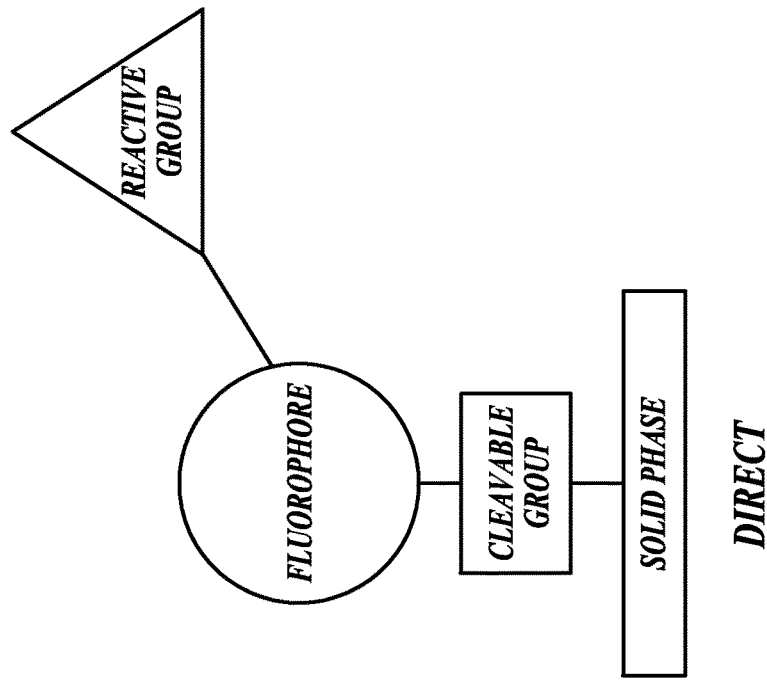
FIGS. 20A and 20B: Comparison of indirect (FIG. 20A) and direct (FIG. 20B) methods of solid-phase attachment of a cleavable anchor or group, fluorophore, and reactive groups.
Figure 20A:
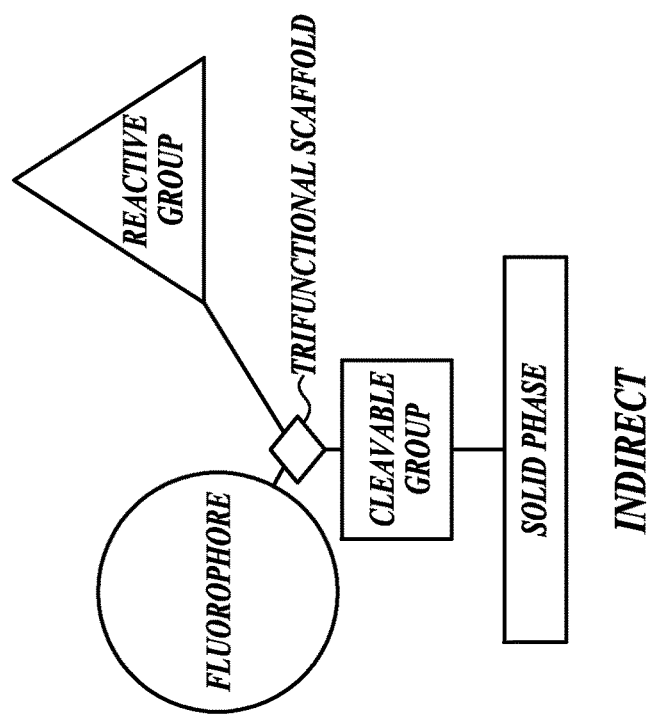

Example 7 describes attachment of a cleavable anchor to a fluorophore. The cleavable anchor can be attached to the fluorophore either indirectly or directly. Schematics are shown in FIGS. 20A (indirect) and 20B (direct).

An indirect attachment requires the use of a trifunctional scaffold that can connect the three main parts of SCaLER together. An example of such a trifunctional scaffold would be based on lysine, where, through proper protection and deprotection strategies, one of the amino groups would be connected to the cleavable anchor, the other amino group would be coupled to the fluorophore, and the carboxylate group would be connected to a tethered reactive arm. Such a scaffold would allow the use of practically any amine-reactive fluorescent label in the SCaLER SPR format.

Direct attachment involves connecting the anchor either to one of the existing substituents or to the core aromatic ring of the fluorophore. This coupling must not impair the fluorescence of the fluorophore or the ability of the reactive arm to derivatize the analyte. The type of coupling to be selected is specific to the type of the fluorophore used for SCaLER.

A synthesis of a solid phase and an immobilization of a fluorophore through a cleavable anchor is shown in Example 8. There are specific preferences for the solid phase of the SCaLER SPR to be effective. One is good mass transfer properties. This allows the analytes to have speedy access to the reactive sites and ensures efficient recovery of the labeled analytes during cleavage. Another preference is a high surface area which allows high loading of the fluorescent label, even at large label-to-label distances. There are different types of solid surfaces that can meet these preferences. Conventional particle-based porous solid supports can have good mass transfer properties and high surface areas, especially when the particle size is very small. However, as the particle size is decreased, the pressure drop across a column packed with the solid phase increases. Monolithic supports form a second group of solid supports. Monoliths are continuous beds of macroporous polymers with through pores that allow mobile phase to flow through the solid support instead of around it (Svec, F., Frechet, J. M. J., Analytical Chemistry 1992, 64, 820-822). Because of its macroporous nature, a large portion of the surface area of the monolithic solid phase is easily accessible by convection, instead of diffusion alone. They are also easily fabricated into various shapes and sizes, without the need for special column or capillary packing equipment.

Because of the above characteristics, a monolithic support is an attractive choice for the SCaLER SPR. There are numerous chemistries in the literature that are used to make functionalized monoliths (Yu, C., Xu, M. C., Svec, F., Frechet, J. M. J., Journal of Polymer Science Part a-Polymer Chemistry 2002, 40, 755-769; Dulay, M. T., Baca, Q. J., Zare, R. N., Analytical Chemistry 2005, 77, 4604-4610; Viklund, C., Svec, F., Frechet, J. M. J., Irgum, K., Chemistry of Materials 1996, 8, 744-750; Palm, A., Novotny, M. V., Anal. Chem. 1997, 69, 4499-4507; Xie, S. F., Svec, F., Frechet, J. M. J., Journal of Polymer Science Part a-Polymer Chemistry 1997, 35, 1013-1021; Peters, E. C., Petro, M., Svec, F., Frechet, J. M. J., Analytical Chemistry 1998, 70, 2288-2295; Dulay, M. T., Quirino, J. P., Bennett, B. D., Kato, M., Zare, R. N., Analytical Chemistry 2001, 73, 3921-3926). Those with functional groups that allow immobilization of the fluorophore are most useful for SCaLER purposes. Monoliths with epoxy, carboxylic acid and hydroxyl groups are some of these examples.

Exemplary labeling tests using SCaLER SPR are presented in Example 9. Different amines were labeled using the SCaLER SPR. Diamines 4-(2-aminoethyl)morpholine (AEM) and 1-methylpiperazine (MP) were used to test the ability of the reagent to effectively label amines at low concentrations. Since the SPR will eventually be used for the ε-amino groups of lysine residues in proteins, a lysine derivative, N-acetyl-L-lysine amide was also used as a test compound to mimic their reactivity.

EXAMPLES

Example 1: Sulfonamidation Preparations

Materials and Methods. 8-Aminopyrene-1,3,6-trisulfonic acid, trisodium salt was provided by Beckman Coulter. 2-Chloroethanesulfonyl chloride (95% purity) was purchased from TCI America. Neopentyl alcohol, chlorosulfonic acid and triethylamine were purchased from Sigma Aldrich. Methylamine was acquired from MC&B as a 40% solution in water. Bare fused silica capillaries for CE analysis were purchased from Polymicro Technologies. All HPLC columns used were purchased from Phenomenex.

CE analysis was carried out in a UV-detector equipped Beckman PA800 system. HPLC analyses were run on a Beckman HPLC system that had a 508 autosampler, 126 pump and 168 PDA (photodiode array) detectors. UV absorbance spectra were taken with the PDA detectors.

Indirect UV detection response factors, degrees of electromigration dispersion and system peak mobilities were simulated with the PeakMaster 5.2 software package (Jaros, M., Hruska, V., Stedry, M., Zuskova, I., Gas, B., *Electrophoresis* 2004, 25, 3080-3085) in order to optimize the background electrolyte compositions for indirect UV detection CE. $pK_a$ values were calculated with the SPARC (SPARC Performs Automatic Reasoning in Chemistry) Online Calculator v4.5 (Hilal, S. H., Karickhoff, S. W., Carreira, L. A., *Quantitative Structure-Activity Relationships* 1995, 14, 348-355).

Sulfonamidation using an aminoalkanesulfonic acid having a primary amine is an attractive option because this will produce a sulfonamide that has an available proton for hydrogen bonding, thus making the fluorophore more water-soluble. However, its calculated $pK_a$ value of this sulfonamido nitrogen is between 9 and 10, making it a weak acid. Deprotonation will affect the electron withdrawing ability of the sulfonamide group and the fluorescence of APTS around this pH region. Furthermore, nucleophilic substitution can also occur at this group. Because of these concerns, sulfonamidation was initially carried out with the commercially available N-methyltaurine. The sulfonic acid groups of APTS were first activated with chlorosulfonic acid and then reacted with N-methyltaurine to make tris sulfonamide 22, shown below.

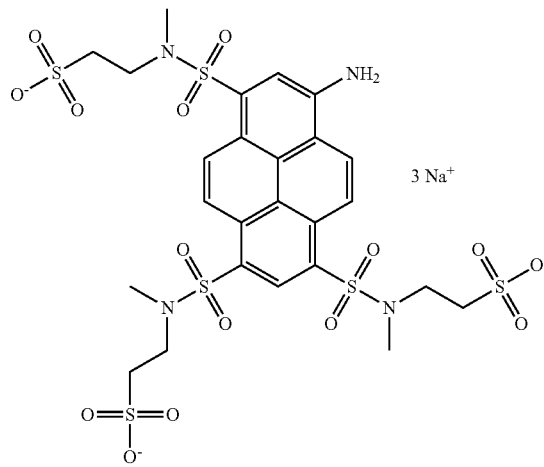

Figure 1:
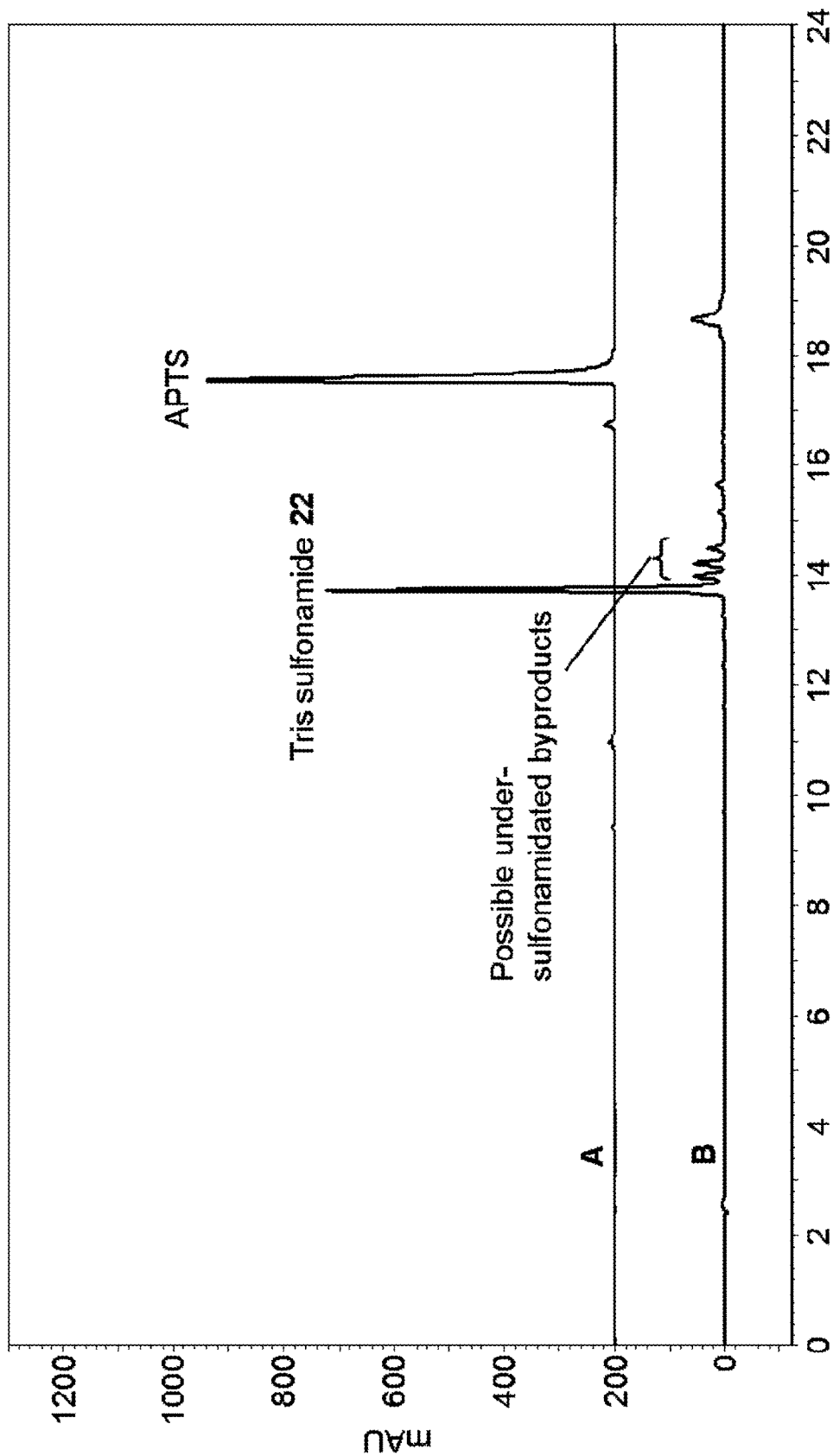
FIG. 1: HILIC analyses of APTS (A) and the sulfonamidation reaction mixture obtained with N-methyltaurine (B). Binary gradient elution: 1 mL/min, 95 to 65% B in 20 min. (A: 100 mM ammonium formate in water; B: ACN).

The starting material and reaction mixture were analyzed by hydrophilic interaction liquid chromatography (HILIC), as shown in FIG. 1. HPLC analysis showed that there were several byproducts that eluted very closely to the target major peak. Their efficient removal by preparative HPLC was only possible up to the second nearest peak. These byproducts were presumed to be under-sulfonamidated APTS molecules which would explain their higher retention and their spectra being an intermediate between those of APTS and compound 22. The highly ionic nature of these byproducts and of the target overwhelms their hydrophobicity differences making selective recrystallization from polar solvents unsuccessful. These difficulties warranted the use of an aminoalkanesulfonic acid with a protected sulfonic acid group for the sulfonamidation reaction.

Figure 2:
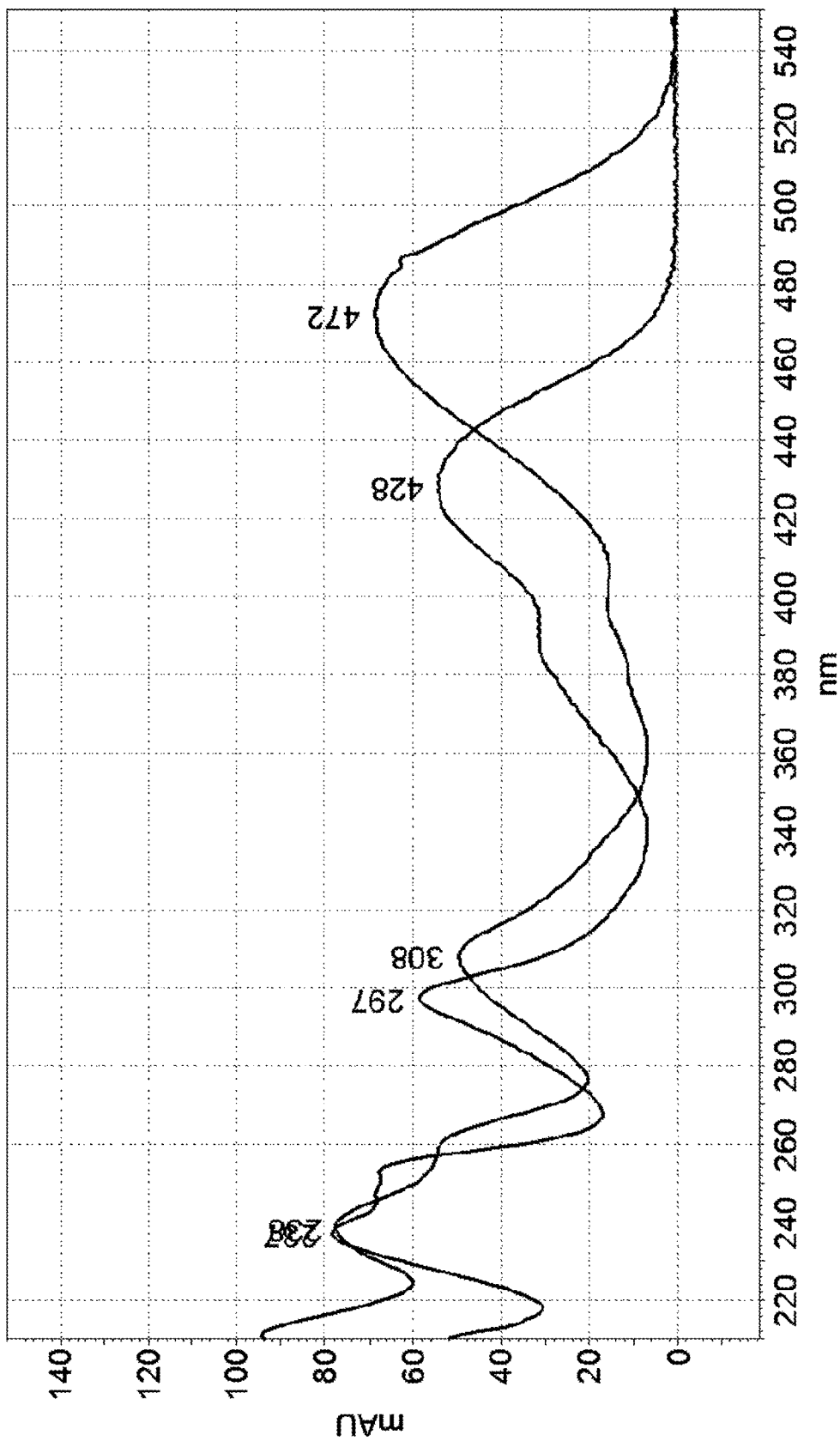
FIG. 2: Overlay of the UV absorbance spectra of APTS and sulfonamidation product 22. The traces are normalized on the 237/238 nm peaks.

The UV absorbance spectra of APTS and tris sulfonamide 22 were compared to see if sulfonamidation indeed brought about an appreciable red shift in $\lambda_{max}^{ex}$. FIG. 2 is an overlay of the UV absorbance spectra of APTS and product 22: indeed, there is a 44 nm shift towards longer wavelength bringing $\lambda_{max}^{ex}$ of the fluorophore closer to 488 nm.

Sulfonamidation with Neopentyl Ester 19. A protected aminoalkanesulfonic acid was prepared from 2-chloroethanesulfonyl chloride:

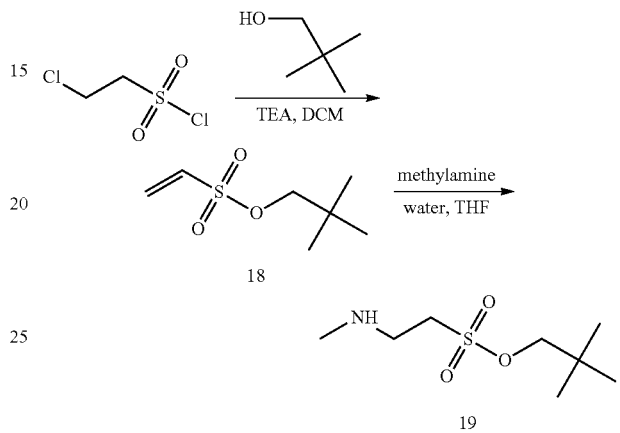

Figure 3:
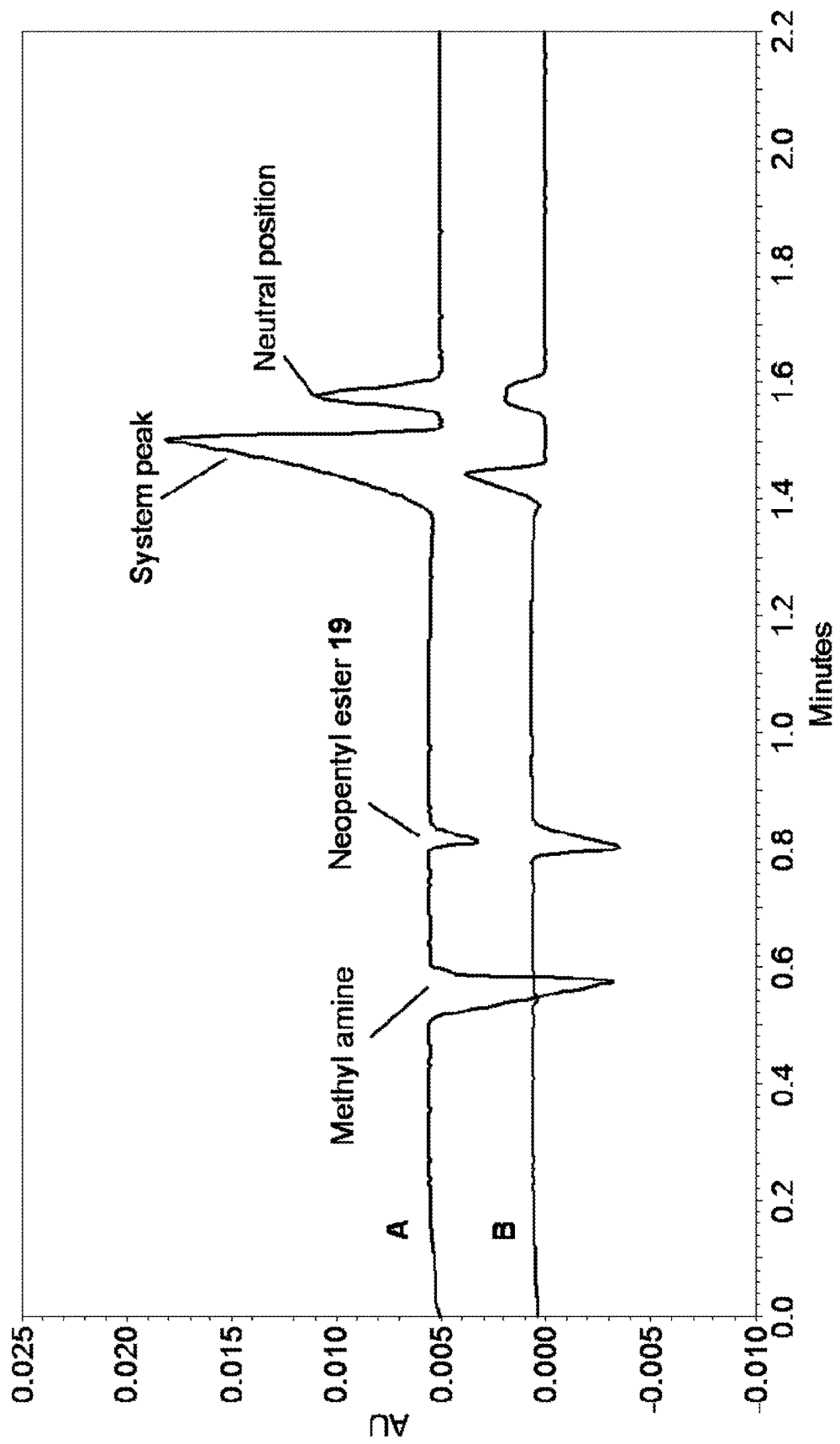
FIG. 3: CE analysis with indirect UV detection of the reaction mixture before (A) and after (B) removal of methylamine.

Reacting the sulfonyl chloride with neopentyl alcohol in the presence of a base formed neopentyl vinylsulfonate ester 18. This was then reacted with excess methyl amine to produce 19, a neopentyl ester of N-methyltaurine. The reaction and workup were monitored by CE with indirect UV detection. FIG. 3 shows the presence of neopentyl ester 19 in the reaction mixture and the removal of methylamine from the final product.

Neopentyl ester 19 was then used for the sulfonamidation reaction after activation of the sulfonic acid groups of APTS with chlorosulfonic acid, as shown below.

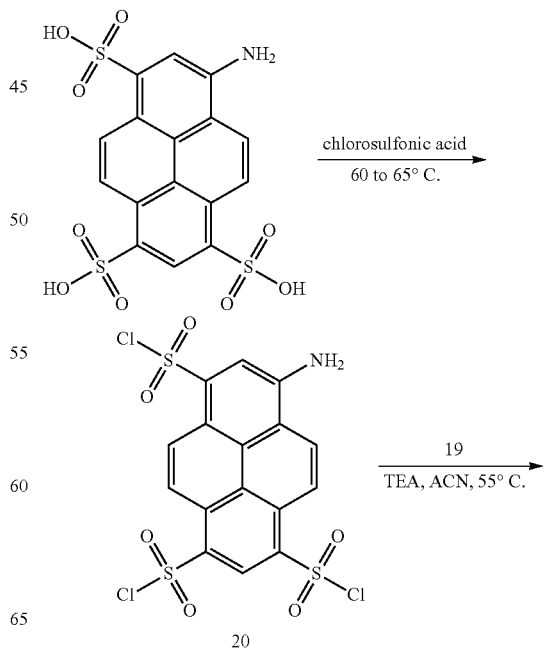

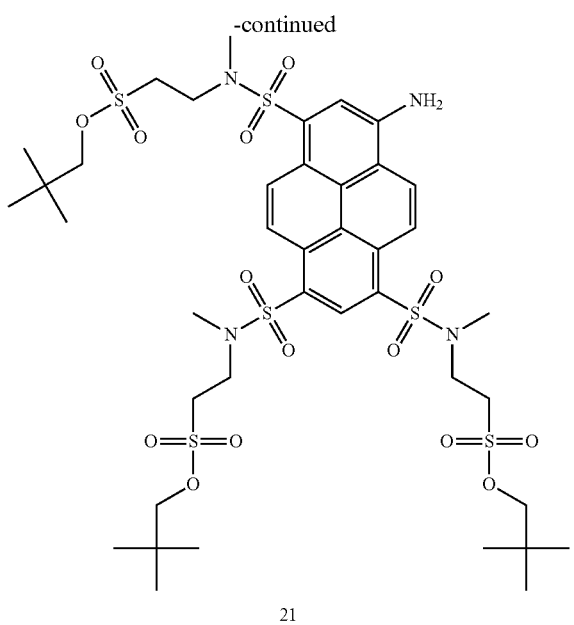

21

Figure 4:
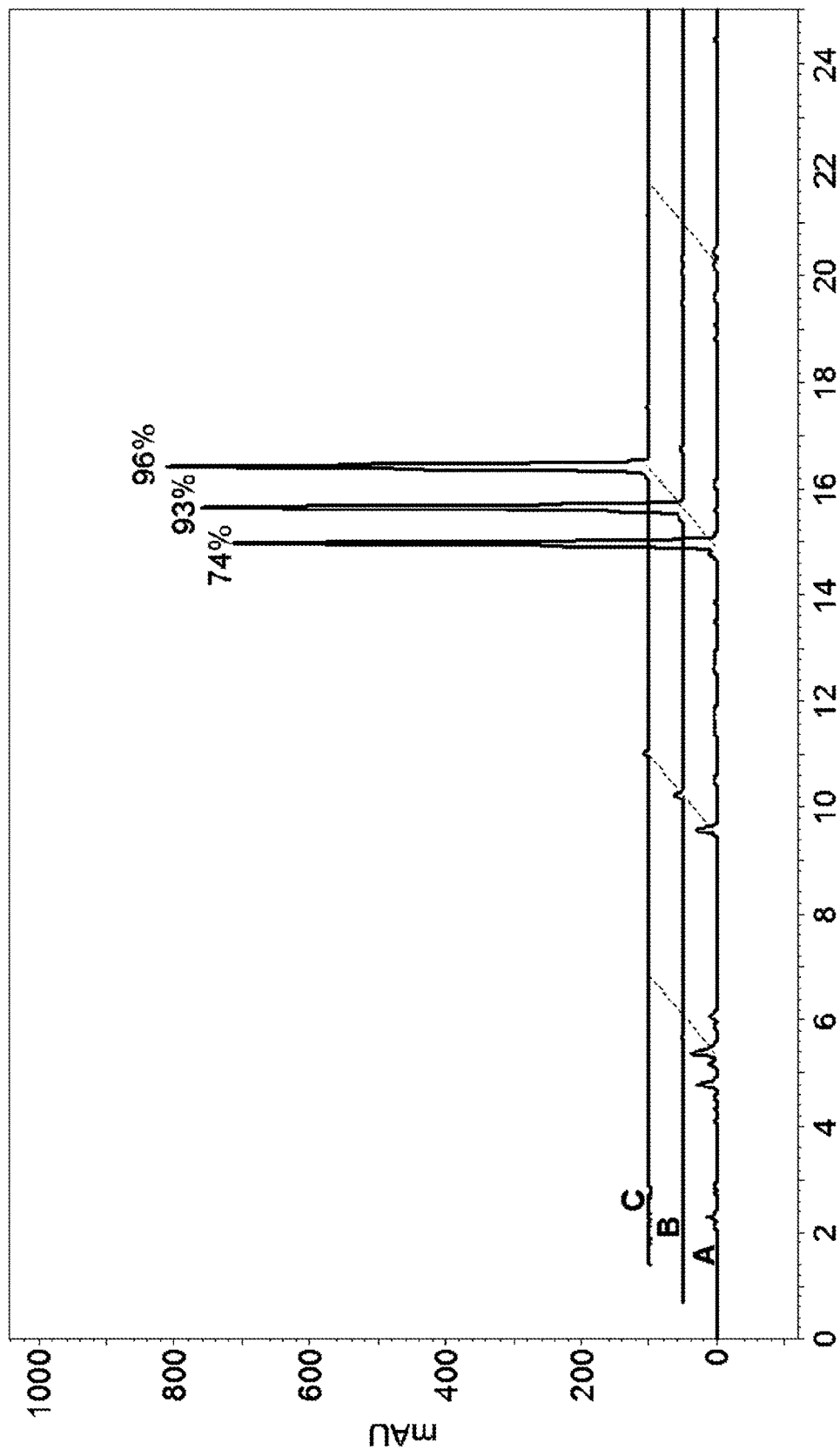
FIG. 4: RP-HPLC of the reaction mixture (A), product from the first recrystallization step (B) and product from the second recrystallization step (C) of trisulfonamide 21. Detection wavelength set at 300 nm. The chromatograms are normalized on the major peak and purities calculated from the peak areas are shown.

The reaction produced tris sulfonamide 21 with an assay purity of 74%. The reaction and work up were monitored by RP-HPLC as shown in FIG. 4. Work up of the material was facile and consisted of two recrystallization steps in a solvent mixture of ACN, formamide and water. The final solid had a purity of 96% based on peak areas detected at 300 nm. The UV absorbance spectrum of tris sulfonamide 21 is almost the same as that of 22 ($\lambda_{max}$ at 239, 308, 476 nm).

Syntheses of 18, 19, 20 and 21 are provided below.

Synthesis of 2,2-Dimethylpropyl Ethenesulfonate 18. 10.0 g (61 mmol) of 2-chloroethanesulfonyl chloride was weighed in a 500-mL round bottom flask. Dichloromethane (150 mL) was added followed by 5.2 g (59 mmol) of neopentyl alcohol. While stirring in an ice bath, 41 mL of triethylamine was slowly added in the span of 6 min. The reaction mixture was stirred at 0° C. for 40 min, then at room temperature for 30 min. Subsequently, the reaction mixture was extracted three times with 150 mL 20% aqueous sodium bisulfate, then once with 150 mL water. The organic phase was dried with anhydrous sodium sulfate and the solvent removed under reduced pressure to give an off-white oily residue (9.54 g, 91% yield).

Synthesis of 2,2-Dimethylpropyl 2-(methylamino)ethanesulfonate 19. Methylamine as a 40% solution in water (83 g, approximately 1 mol) was weighed in a stoppered 500-mL 3-neck round bottom flask with an attached ice water-cooled condenser. Vinylsulfonate 18 (9.5 g, 53 mmol) dissolved in 100 mL tetrahydrofuran (THF) was added to the stirred methylamine solution while in an ice bath. The reaction mixture was stirred for 2 hours at 0° C. and then overnight at room temperature. The solvents were then removed under reduced pressure until a clear oily residue was obtained (11.0 g, 99% yield). The reaction mixture was analyzed by CE with indirect UV detection (254 nm) using a 10 mM acetic acid solution titrated to pH 4.4 with pyridine as BGE (background electrolyte). The capillary used had 50 μm I.D., 360 μm O.D. with inlet-to-detector and total lengths of 20.3 cm and 30.4 cm, respectively.

Synthesis of 8-Aminopyrene-1,3,6-trisulfonyl Chloride 20. 8-Aminopyrine-1,3,6-trisulfonic acid, trisodium salt (4.0 g, 7.6 mmol) was added to 75 mL chlorosulfonic acid while stirring in an ice bath. After addition, the reaction mixture was transferred to a 60 to 65° C. oil bath and was allowed to react for 1.5 hours. The extent of chlorination of APTS was determined by HPLC. An HPLC sample was prepared by adding a 20 μL aliquot of the reaction mixture to 0.2 g of ice in a 1.5 mL Eppendorf tube. After addition, about 0.8 mL of water was added and the slurry was centrifuged. The supernatant was decanted and 50 μL morpholine was added to the solid residue. The sample tube was vortexed for about 5 min and analyzed by HPLC using a Gemini C18 column (3 μm, 100 Å, 150 mm×4.6 mm) with isocratic elution using a binary eluent made of 55% B, at 1 mL/min (A: 2 mM N-methylmorpholine and 1 mM acetic acid in water; B: 2 mM N-methylmorpholine and 1 mM acetic acid in acetonitrile). Once the reaction reached completion, the reaction mixture was cooled to room temperature and added dropwise, very carefully, to 800 g ice-water (the process is very exothermic!). The red precipitate formed was filtered and the pasty solid was used as-is in the next step.

Synthesis of 8-Aminopyrene-1,3,6-trisulfonamide 21. Amine 19 (27 g, 129 mmol) was combined with 50 mL ACN in a beaker and added to 30 mL triethylamine. Sulfonyl chloride 20 was then added to the mixture and transferred to a 250-mL round bottom flask. An additional 100 mL of ACN was used to wash all of the reaction mixture into the flask. The dark brown-red mixture was stirred at 55° C. for about 1 hour, then at room temperature overnight. Subsequently, the solvent was removed under reduced pressure to yield a viscous dark brown liquid. The residue was dissolved in 60 mL ACN and 160 mL formamide at 50° C. Using a dropping funnel, 24 mL of water was added to the solution at a rate of about 1 drop per 3 to 5 seconds while stirring at 50° C. The mixture was then allowed to cool to room temperature to precipitate the desired material. The solid was filtered out and the recrystallization step was repeated one more time. The solid was washed with water to remove excess formamide (3.8 g, 49% yield). The reaction mixture and the products from the recrystallization steps were analyzed by RP-HPLC using the same column as described above. The sample was eluted with a binary gradient of 60% to 90% B in 20 min at 1 mL/min (A: 2 mM N-methylmorpholine and 1 mM acetic acid in water; B: 2 mM N-methylmorpholine and 1 mM acetic acid in ACN). The chromatograms were detected at 300 nm.

Example 2: Anilinic Amino Group Alkylation Reactions

A tether based on tetraethyleneglycol was prepared according to the reaction scheme below:

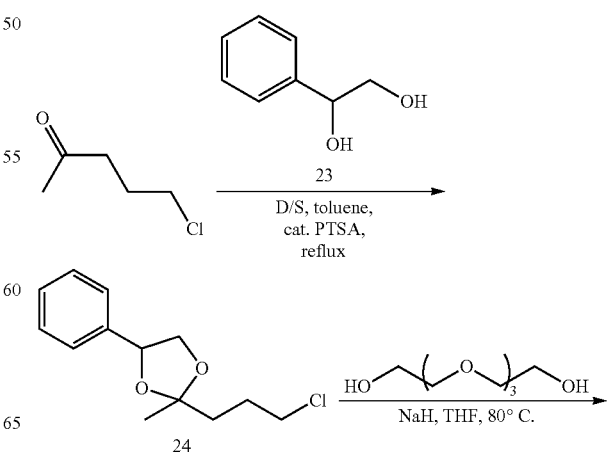

-continued

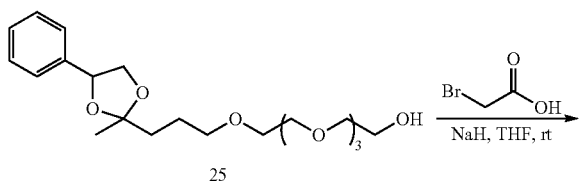

under acidic conditions to form carboxylic acid 27. Since the free carboxylic acid would form an amide with amine 21 under the dehydrating conditions used for the reductive amination, 27 was converted into methyl ester 28 by refluxing in methanol and dichloroethane, with a catalytic amount of sulfuric acid.

Fluorophore tether intermediate 28 was then used for the alkylation of tris sulfonamide 21 to obtain alkylated product 29:

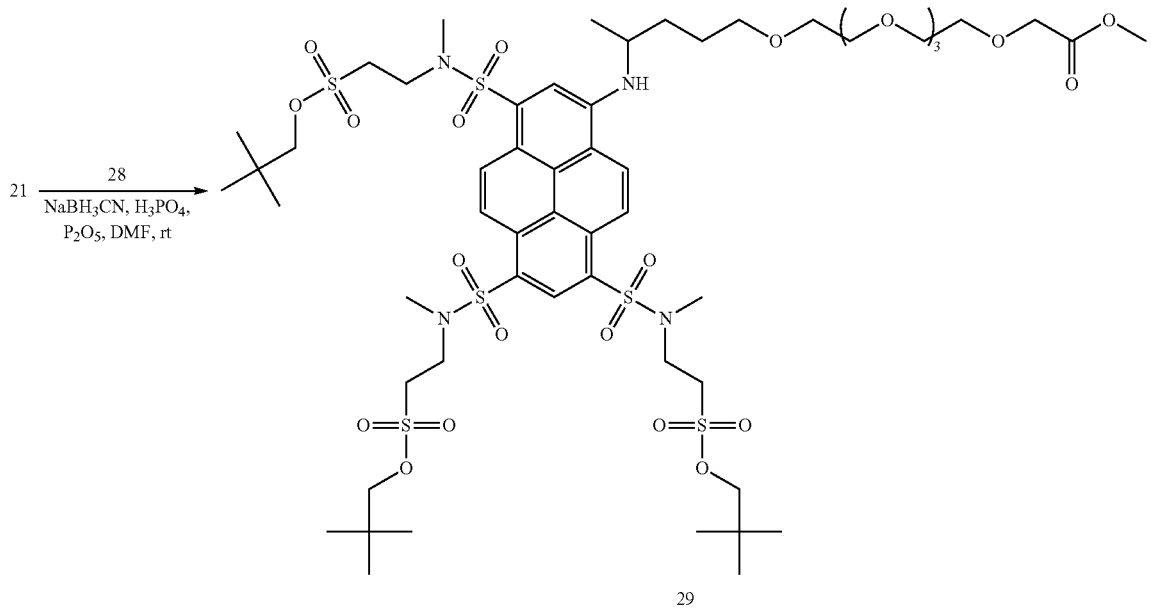

-continued

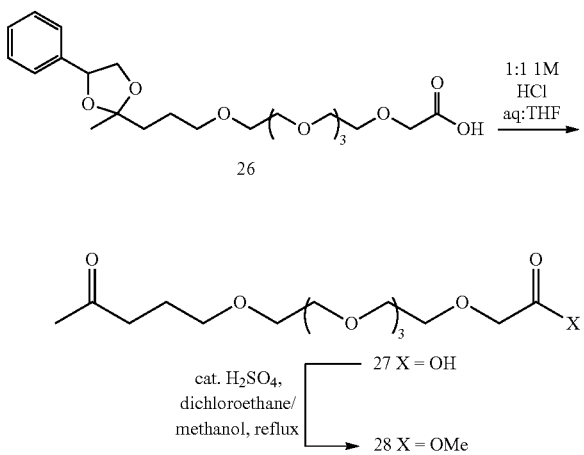

Figure 5:
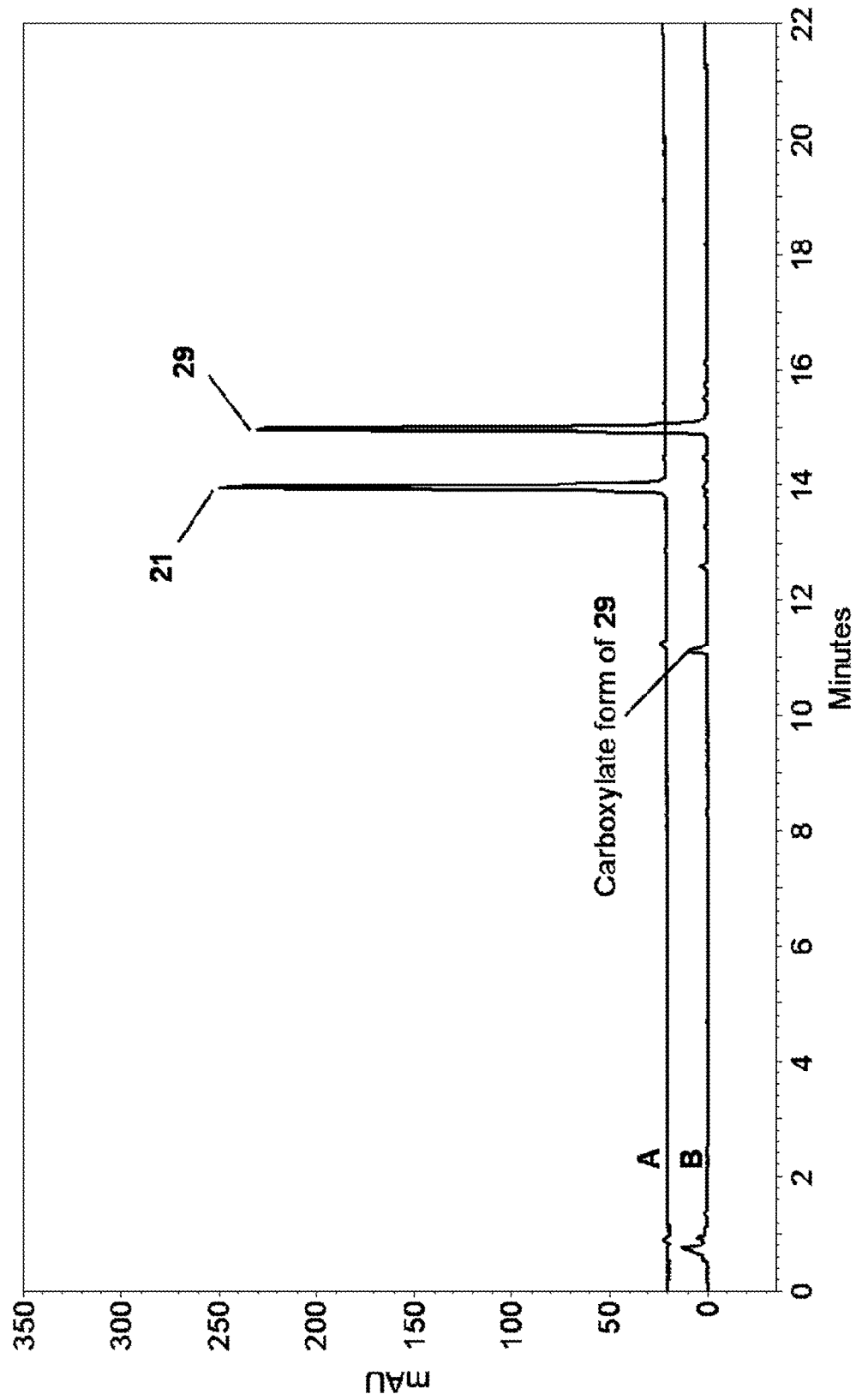
FIG. 5: RP-HPLC of starting material 21 (A) and the reductive amination reaction mixture containing 20 equiv. ketone 28 and 10 equiv. $NaBH_3CN$ in the presence of $H_3PO_4/P_2O_5$ in DMF after 30 min (B).

The preparation started with 5-chloro-2-pentanone to provide the ketone needed for the fluorophore tether. The ketone was protected with 23 as a 1,3-dioxolane to give chloro derivative 24. The latter was subsequently coupled to tetraethyleneglycol to form dioxolane-terminated PEG 25. Bromoacetic acid was reacted with 25 in the presence of sodium hydride to produce dioxolane/carboxylic acid-terminated PEG 26. The dioxolane group of 26 was then hydrolyzed With 20 equivalents of the ketone and 10 equivalents of sodium cyanoborohydride, the reaction went to completion in 30 minutes at room temperature as shown by the HPLC trace in FIG. 5. A small amount of the carboxylate form of 29 was observed because about 5% of PEG-based tether intermediate 28 was present in the carboxylic acid form. However, this was not a concern because the methyl ester was to be hydrolyzed to the carboxylic acid in a later step of the fluorophore preparation scheme. The reductive amination conditions were further optimized by lowering the amount of $P_2O_5$ and using orthophosphoric acid instead of 85% $H_3PO_4$. Only about 2.5 equiv. of sodium cyanoborohydride were added. The ketone was still added in excess at 20 equiv., because a lower excess produced a small amount of an unknown byproduct. The reaction took 16 hours to complete.

Materials and Methods. Acrylic acid, methyl ethyl ketone, ethyl-4-acetylbutyrate, sodium cyanoborohydride, phosphorus pentoxide, styrene oxide, 5-chloro-2-pentanone, sodium hydride (60% dispersion in oil), tetraethyleneglycol, and bromoacetic acid were purchased from Sigma Aldrich.

Synthesis of Styrene Glycol 23. Styrene oxide (150 g) was added to 1.5 L of water and stirred for 3 hours at 60° C., then for about half an hour at 90° C. Subsequently, a 100 g portion of styrene oxide was added and heating was continued for 6 hours at 60 to 70° C., then for 1.5 hours at 85° C. After cooling, water was evaporated under reduced pressure and the solid residue was recrystallized from toluene (twice) giving 23 in 97% purity by HPLC (detection at 270 nm).

Synthesis of Dioxolane 24. A mixture of 23 g (167 mmol) styrene glycol 23, 5.0 g (41.5 mmol) 5-chloro-2-pentanone, 78 mg (0.4 mmol) p-toluenesulfonic acid, monohydrate, and 200 mL toluene was refluxed in a 500 mL round bottom flask with an attached Dean-Stark apparatus. Formation of the dioxolane ring was monitored by RP-HPLC. Reflux was stopped once HPLC showed complete conversion of the ketone to 24 (detection at 270 nm). Subsequently, 24 was filtered from the cooled reaction mixture, digested with 100 mL toluene and filtered again. The toluene filtrates were combined, mixed with 5 g potassium carbonate, stirred and filtered. Toluene was then removed under reduced pressure. The residue was digested in 200 mL hexanes and filtered to remove most of the remaining styrene glycol. The hexanes filtrate was evaporated under reduced pressure and the remaining oil was digested in 48 mL N,N-dimethylformamide (DMF) and 120 mL water. The mixture was allowed to settle and the supernatant was decanted. The DMF/water digestion was repeated one more time on the bottom phase. The oil from the digestions was subsequently partitioned between 20 mL of toluene and 15 mL of water. The solvent from the organic phase was removed under reduced pressure giving a clear colorless oil (6.5 g, 65% yield). The reaction and work up were monitored by RP-HPLC using a Gemini C18 column (3 µm, 100 Å, 150 mm×4.6 mm) with a binary gradient of 20% to 70% B in 25 min at 1 mL/min (A: 2 mM N-methylmorpholine and 1 mM acetic acid in water; B: 2 mM N-methylmorpholine and 1 mM acetic acid in ACN).

Synthesis of Tetraethyleneglycol-decorated Dioxolane 25. Sodium hydride, as a 60% dispersion in oil (2.2 g, 55 mmol) was weighed in a 250 mL round bottom flask and was stirred in 50 mL hexanes under nitrogen blanket. The slurry was allowed to settle and the hexanes were cannulated out. Using a dropping funnel, a mixture of 53 g (273 mmol) tetraethyleneglycol and 50 mL THF was very carefully added dropwise to the stirred sodium hydride. Once gas evolution has ceased, the rate of alcohol addition was carefully increased. The solution was stirred at room temperature for about 10 min. After this, 0.9 g (5.4 mmol) of potassium iodide was dropped in. A mixture of 6.5 g (27 mmol) dioxolane 24 and 20 mL THF was added dropwise using a dropping funnel, then the temperature of the reaction mixture was increased to about 60° C. and THF was distilled off under a light vacuum. After complete removal of THF, the reaction temperature was increased to 80° C. The reaction was complete after 7 hours as determined by RP-HPLC. The reaction mixture was cooled to room temperature and partitioned between 100 mL dichloromethane and 200 mL 10% aqueous sodium chloride. The organic phase was extracted with 200 mL 10% aqueous sodium chloride two more times. The organic phase was dried with sodium sulfate and evaporated under reduced pressure yielding an oil (9.5 g 88% yield). HPLC was carried out using a Gemini C18 column (3 µm, 100 Å, 100 mm×4.6 mm) with a binary gradient of 20% to 70% B in 20 min at 1 mL/min (A: 2 mM N-methylmorpholine and 1 mM acetic acid in water; B: 2 mM N-methylmorpholine and 1 mM acetic acid in ACN).

Synthesis of Dioxolane/Carboxylic Acid-Terminated Tetraethyleneglycol 26. Sodium hydride, as a 60% dispersion in oil (12.0 g, 300 mmol) was weighed in a 1-L round bottom flask and stirred in 100 mL hexanes under nitrogen blanket. The slurry was allowed to settle and the hexanes were cannulated out. 100 mL of THF was then added in. While stirring in a water bath, a mixture of 17.3 g (125 mmol) bromoacetic acid and 40 mL THF was carefully added dropwise using a dropping funnel. The addition rate was controlled to avoid excessive hydrogen formation. A mixture of 45 g (88 mmol) of dioxolane 25 (~77% purity) and 100 mL THF was then carefully added dropwise. Stirring was continued while in a water bath: the reaction was completed in 2 hours as shown by RP-HPLC. 50 mL of methanol was then slowly added followed by 250 mL of 10% aqueous sodium bicarbonate. The solvent was removed under reduced pressure. The wet solid residue was digested in 100 mL ACN at 80° C. for 5 min, cooled in an ice bath and filtered. The solids were washed with 150 mL ACN. More of the solids were forced out from the filtrate by adding 300 mL each of THF and methyl-t-butyl ether (MTBE) and slurry filtered. The filtrate was evaporated under reduced pressure. The oily residue was then redissolved in 100 mL THF to precipitate more of the inorganic solids and centrifuged. To the supernatant, 700 mL MTBE was added, swirled and allowed to settle for 6 hours. Subsequently, the supernatant was decanted leaving a viscous liquid settled at the bottom. The THF-MTBE treatment was repeated one more time. Carried over solvent was evaporated from the bottom phase under reduced pressure to afford a light brown oil with a purity of about 85% as determined by HPLC (39 g, 82% yield). HPLC analysis was performed using a Gemini C18 column (3 µm, 100 Å, 100 mm×4.6 mm) with a binary gradient of 20% to 80% B in 20 min at 1 mL/min (A: 2 mM N-methylmorpholine and 1 mM acetic acid in water; B: 2 mM N-methylmorpholine and 1 mM acetic acid in ACN).

Synthesis of Ketone/Carboxylic Acid-Terminated Tetraethyleneglycol 27. Dioxolane 26 (39 g, 72 mmol) was combined with 500 mL 1:1 mixture of 1M aq. HCl: THF and stirred until dioxolane hydrolysis was complete as determined by RP-HPLC. The mixture was neutralized with sodium bicarbonate until gas evolution has stopped. The solvent was removed under reduced pressure. The residue was partitioned between 200 mL ethyl acetate and 100 mL water to remove styrene glycol. The aqueous phase was extracted two more times with 200 mL ethyl acetate. Carried over ethyl acetate was removed under reduced pressure and the remaining aqueous solution of the target was acidified with 11 mL concentrated HCl. This was then extracted with 200 mL MTBE six times. The acidic aqueous phase was then neutralized with sodium carbonate and water was removed under reduced pressure. The residue was digested in 200 mL ACN and filtered. ACN was evaporated leaving a light caramel colored viscous residue (18.8 g, 73% yield). HPLC monitoring was done using a Gemini C18 column (3 µm, 100 Å, 100 mm×4.6 mm) with a binary gradient of 10% to 50% B in 16 min at 1 mL/min (for monitoring the dioxolane hydrolysis reaction: A: 2 mM N-methylmorpholine and 1 mM acetic acid in water; B: 2 mM N-methylmorpholine and 1 mM acetic acid in ACN; for monitoring the workup: A: 0.1% trifluoroacetic acid in water; B: 0.1% trifluoroacetic acid in ACN).

Synthesis of PEG-based Fluorophore Tether Intermediate 28. 110 mL dichloroethane and 30 mL methanol were added to 18.8 g (53 mmol) carboxylate 27. Sulfuric acid (2.8 g) was carefully added and the mixture was refluxed for about 4 hours or until methyl ester formation was complete as shown by RP-HPLC. The mixture was cooled, then quenched with about 1.5 g sodium bicarbonate in 20 mL water, making sure that the pH of the solution did not go above 7. The solvents were removed under reduced pressure. Subsequently, the residue was digested in 200 mL THF for about 30 min at 65° C., then cooled to room temperature and filtered. The solvent was evaporated under vacuum to afford a brown viscous oil (15.5 g, 84% yield). HPLC monitoring was done using a Gemini C18 column (3 µm, 100 Å, 100 mm×4.6 mm) with a binary gradient of 10% to 50% B in 16 min at 1 mL/min (for monitoring the methyl ester formation reaction: A: 0.1% trifluoroacetic acid in water; B: 0.1% trifluoroacetic acid in ACN; for monitoring the workup: A: 2 mM N-methylmorpholine and 1 mM acetic acid in water; B: 2 mM N-methylmorpholine and 1 mM acetic acid in ACN).

Synthesis of Alkylated APTS Trisulfonamide 29. Method A: Anhydrous DMF (15 mL) and 85% $H_3PO_4$ (2 mL) were combined in a 500-mL round bottom flask with an attached mechanical stirrer. While stirring in a water bath, ~12 g of $P_2O_5$ was slowly added to create a homogenous paste. Then, 3.4 g (9.7 mmol) of ketone 28 was added in. The mixture became more viscous and sticky after the addition of the ketone. This mixture was stirred further for 15 minutes before addition of 0.5 g (0.5 mmol) of amine 21. The mixture was stirred for another 20 min, after which 2.5 mL of $NaBH_3CN$ in anhydrous DMF was dropped in while stirring. The paste color turned from red-brown to red-orange seconds after the addition. The reaction was complete after 30 minutes as shown by RP-HPLC analysis.

A mixture of 27 g $Na_2CO_3$ and 200 mL water was added slowly to the reaction mixture while it was stirred in an ice bath. Ethyl acetate (200 mL) was then added and the mixture stirred for 30 min. The two phases were separated, the organic phase was dried with sodium sulfate and evaporated under reduced pressure. The sticky viscous residue was added to 25 mL water, swirled vigorously and allowed to settle for a few minutes. The supernatant was decanted and centrifuged to recover any carried over target material. Water digestion was repeated for the remaining residue. All the viscous residue was dissolved in 50 mL dimethylsulfoxide (DMSO) and added drop by drop to a stirred, 50 mL portion of a 10% aqueous sodium chloride solution. The slurry was stirred and allowed to settle. The supernatant was decanted and centrifuged to recover the carried over solids. Precipitation was repeated one more time. The resulting sticky solid was dissolved in ethyl acetate, filtered and evaporated under reduced pressure to afford a dark red-orange residue (0.62 g, 91% yield). HPLC analysis was done using a Gemini C18 column (3 μm, 100 Å, 75 mm×4.6 mm) with a binary gradient of 40% to 100% B in 18 min at 1 mL/min (A: 2 mM N-methylmorpholine and 1 mM acetic acid in water; B: 2 mM N-methylmorpholine and 1 mM acetic acid in ACN).

Synthesis of Alkylated APTS Trisulfonamide 29. Method B: 1.2 g of $P_2O_5$ and 1.2 g orthophosphoric acid were weighed into a 25 mL round bottom flask. 10.2 mL anhydrous DMF was added and stirred. The flask was well sealed to keep moisture out. 4.06 g (11.6 mmol) of ketone 28 was added to the DMF mixture and was stirred for 3 minutes before addition of 0.40 g (0.6 mmol) tris sulfonamide 21. The mixture was stirred for another 30 minutes at room temperature, after which 728 μL of 2M $NaBH_3CN$ in anhydrous DMF was added. The color of the reaction mixture turned from red-brown to red-orange and conversion was complete after 16 hours as determined by RP-HPLC analysis.

The reaction mixture was partitioned between 75 mL ethyl acetate and 150 mL 10% aqueous sodium carbonate. The organic layer was extracted again with 150 mL aq. $Na_2CO_3$. The aqueous layers were combined and back-extracted with 75 ml of ethyl acetate. The ethyl acetate phases were combined and washed with 150 mL 1M sodium phosphate, pH 5.6, to neutralize any carried-over sodium carbonate. The organic phase was dried with sodium sulfate and evaporated under reduced pressure. The remaining residue was a dark red brown liquid. To this was added 30 mL methanol, heated to reflux and, while stirring, slowly added 30 mL of water at a rate of 1 drop per second. Red-brown gum precipitated out from solution. The mixture was allowed to cool. The supernatant was decanted and centrifuged to recover carried over material. Precipitation was repeated three more times using 30 mL water and twice more using 15 mL water. Water and methanol residues were evaporated under reduced pressure (0.71 g, 86% yield).

HPLC analysis was done using a Gemini C18 column (3 μm, 100 Å, 150 mm×4.6 mm) with an isocratic elution of 80% B at 1 mL/min (A: 2 mM N-methylmorpholine and 1 mM acetic acid in water; B: 2 mM N-methylmorpholine and 1 mM acetic acid in ACN).

Example 3: Neopentyl Protecting Group Deprotection Procedures and Purification of a Sulfonic Acid Compound Materials and methods. Tetramethylammonium chloride (TMACl), tetraethylammonium chloride (TEACl), benzyltrimethylammonium chloride (BnTMA), tetrabutylammonium hydroxide (TBAOH) and sodium trifluoroacetate (NaTFA) were purchased from Sigma Aldrich. Analytical and semi-preparative HPLC columns were provided by Phenomenex.

Synthesis of Sulfonic Acid 32 (Removal of the Neopentyl Protecting Group). 0.6 g (0.44 mmol) neopentyl sulfonate ester 29 was dissolved in 10 mL DMSO. 1.0 g tetraethylammonium chloride was added and the mixture was heated to 115-120° C. The reaction was monitored closely by HILIC and found to be complete after 4 hours. The target was precipitated by adding 100 mL of a 1:1 mixture of THF and MTBE. The heterogeneous mixture was then distributed into multiple centrifuge vials and centrifuged. The supernatant was decanted and the bottom viscous liquids were dissolved in a total of 10 mL ACN and combined. The target was again precipitated by adding an 80 mL portion of a 1:1 mixture of THF:MTBE. This dissolution-precipitation step in ACN and THF/MTBE was repeated one more time. The resulting red-brown viscous liquid was vortexed in 40 mL THF, centrifuged and decanted twice (the bottom phase was not flowing anymore). The material (32 and carried over TEACl) was used as-is in the next step. HILIC analysis was done using a Luna HILIC column (3 μm, 200 Å, 150 mm×4.6 mm) with a binary gradient of 95% to 75% B in 20 min at 1 mL/min (A: 10 mM 3-morpholinopropane-1-sulfonic acid (MOPS) and 5 mM sodium hydroxide (NaOH) in water; B: 10 mM MOPS and 5 mM NaOH in 5% water in ACN).

Hydrolysis of Methyl Ester 32 to Form Carboxylic Acid 33. The solid from the previous step was dissolved in 5 mL 0.01M aqueous sodium hydroxide and stirred at room temperature. Complete ester hydrolysis was accomplished after 10 minutes as determined by HILIC. The base was then quenched by adding a mixture of 75 μL trifluoroacetic acid, 140 μL triethylamine and 0.5 mL water. The mixture was evaporated under vacuum to afford a dark red gummy solid residue. This was dissolved in 25 mL ACN and added dropwise to a solution of 5 g sodium trifluoroacetate (NaTFA) in 25 mL ACN while stirring. Excess NaTFA ensured that the counterion of 33 during semi-prep HILIC was sodium, not tetraethylammonium. The resulting slurry was centrifuged, decanted and the bottom solid phase set aside. The supernatant was evaporated. The residue went through a series of digestions, first with 100 mL of 1:1 THF:MTBE, then with 50 mL THF and lastly with 50 mL ACN. The red orange solid was combined with the previously set aside solid from the sodium ion exchange step and dissolved in about 3 mL of water. Some of the water was evaporated to reduce the volume to about 2 mL. At this volume, the concentration of 33 was high enough to have a high semi-prep HILIC throughput while the viscosity of the mixture was not too high allowing good injection in the sample loop. HILIC was done the same way as above.

Figures 6A, 6B:
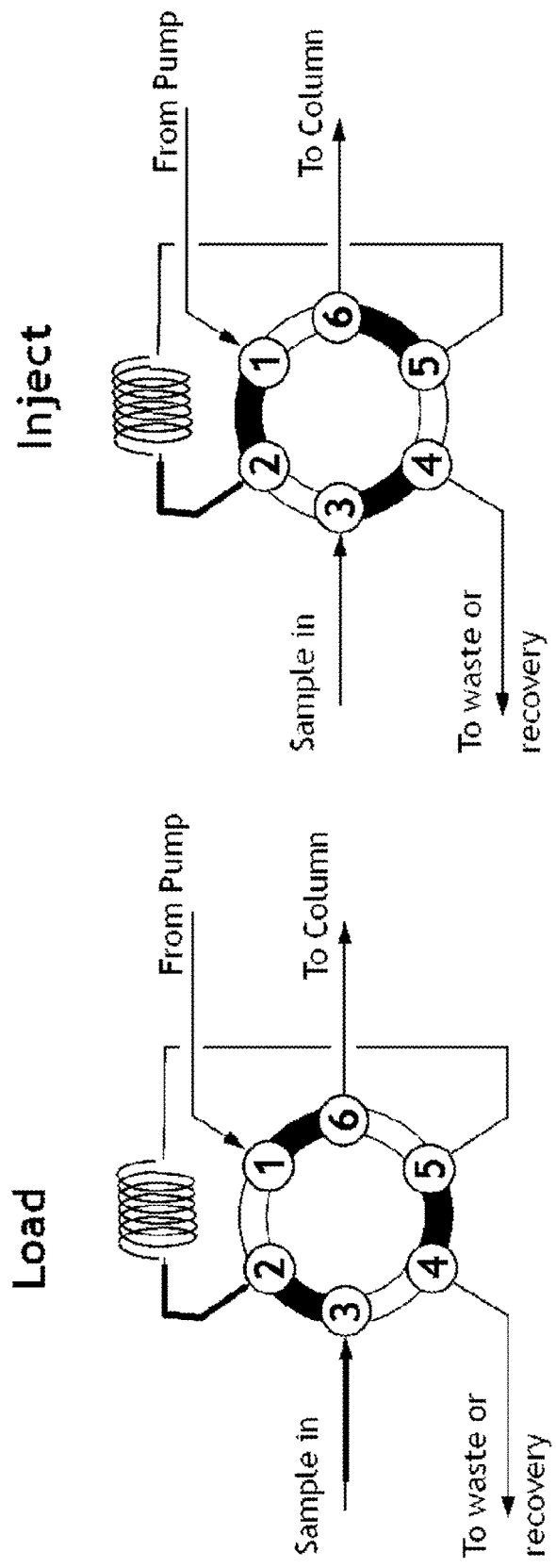
FIGS. 6A and 6B: Sample loop configuration that allows in-line "Taylor" dilution of a sample loaded in a strong solvent for prep HPLC.

Semi-Preparative HILIC of Tetra-anion 33. A solution of 33 from the previous step was used as the feed for the semi-prep HILIC separation. About 200 to 250 µL of the solution, corresponding to approximately 50 mg of dissolved material, was injected. The sample loop configuration is shown in FIGS. 6A and 6B. The sample loop used was a stainless steel 5-mL Rheodyne loop with an approximate I.D. of 1 mm. The semi-prep HILIC separations were carried out in a Beckman HPLC system equipped with a 508 autosampler, 126 pump and 168 photodiode array detector. The HILIC column was a Luna 5 µm HILIC column (250 mm×10 mm) with a HILIC guard cartridge. The flow rate was 5 mL/min. After sample injection, there was a 4 min long isocratic elution segment at 92% B that was followed by a step change to 77% B. The eluent composition was maintained at this concentration until the desired component was eluted, followed by a 5-minute cleaning of the column at 40% B, before going back to the initial composition, 92% B (A: 20 mM sodium trifluoroacetate in water; B: 20 mM sodium trifluoroacetate in ACN). Solvents were filtered through a 0.65 µm PVDF membrane filter from Millipore. The collected fractions had a total volume of 400 mL. A 40-mL aliquot was taken and evaporated under reduced pressure to afford a dark red-orange residue. The solid was then dissolved in 0.5 mL DMSO and reprecipitated with 7 mL ACN to remove sodium trifluoroacetate. The slurry was centrifuged and the resulting orange solid was redissolved and reprecipitated two more times using DMSO and ACN. Finally, the solid was washed with ACN and dried in vacuum over $P_2O_5$ (43 mg, 72% yield for the 40 mL aliquot taken through the deprotection and hydrolysis steps). HILIC was done the same way as above.

Removal of the Neopentyl Protecting Group. One method to remove the neopentyl protecting group from tris sulfonamide 29 is shown below:

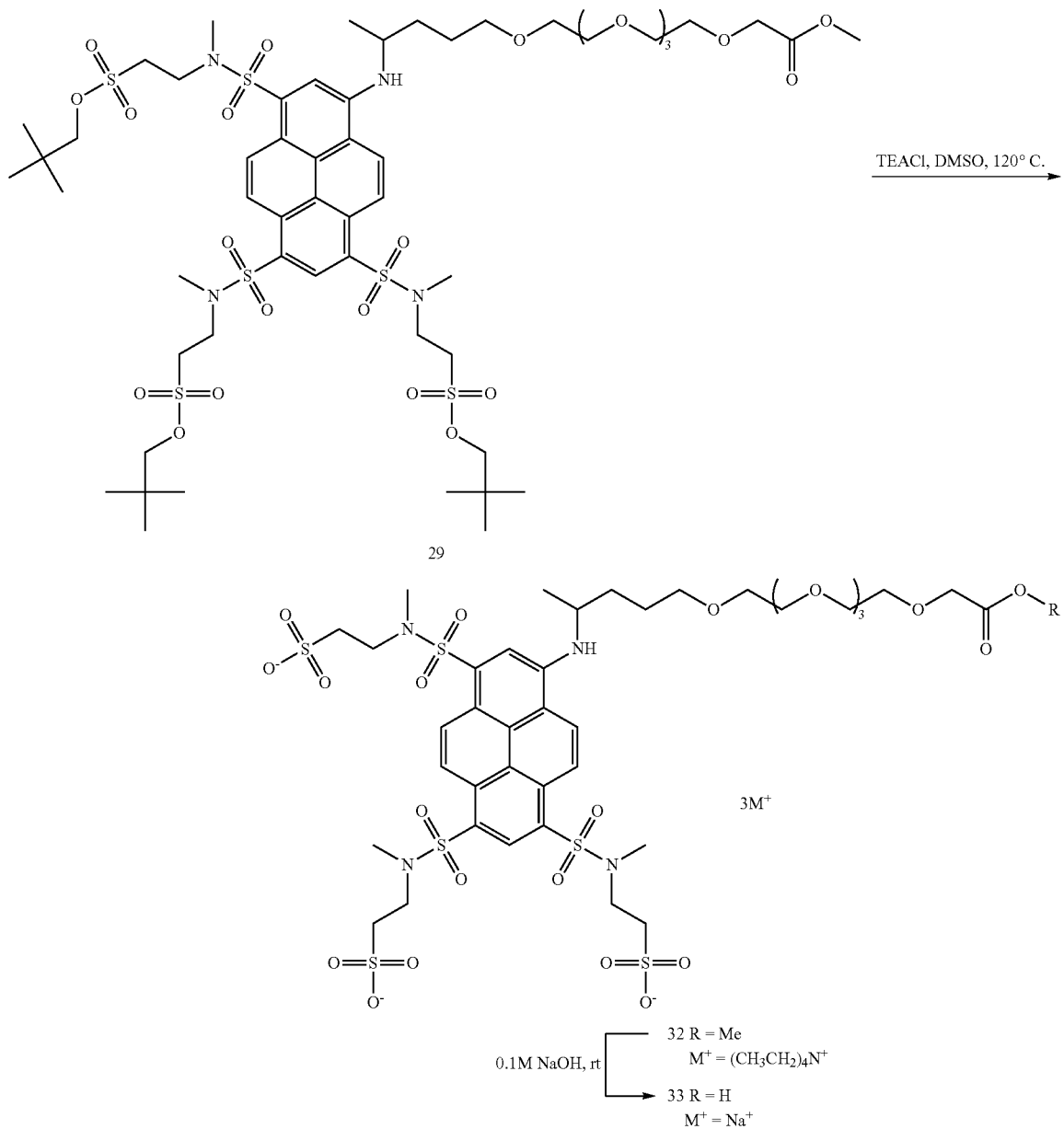

Figure 7:
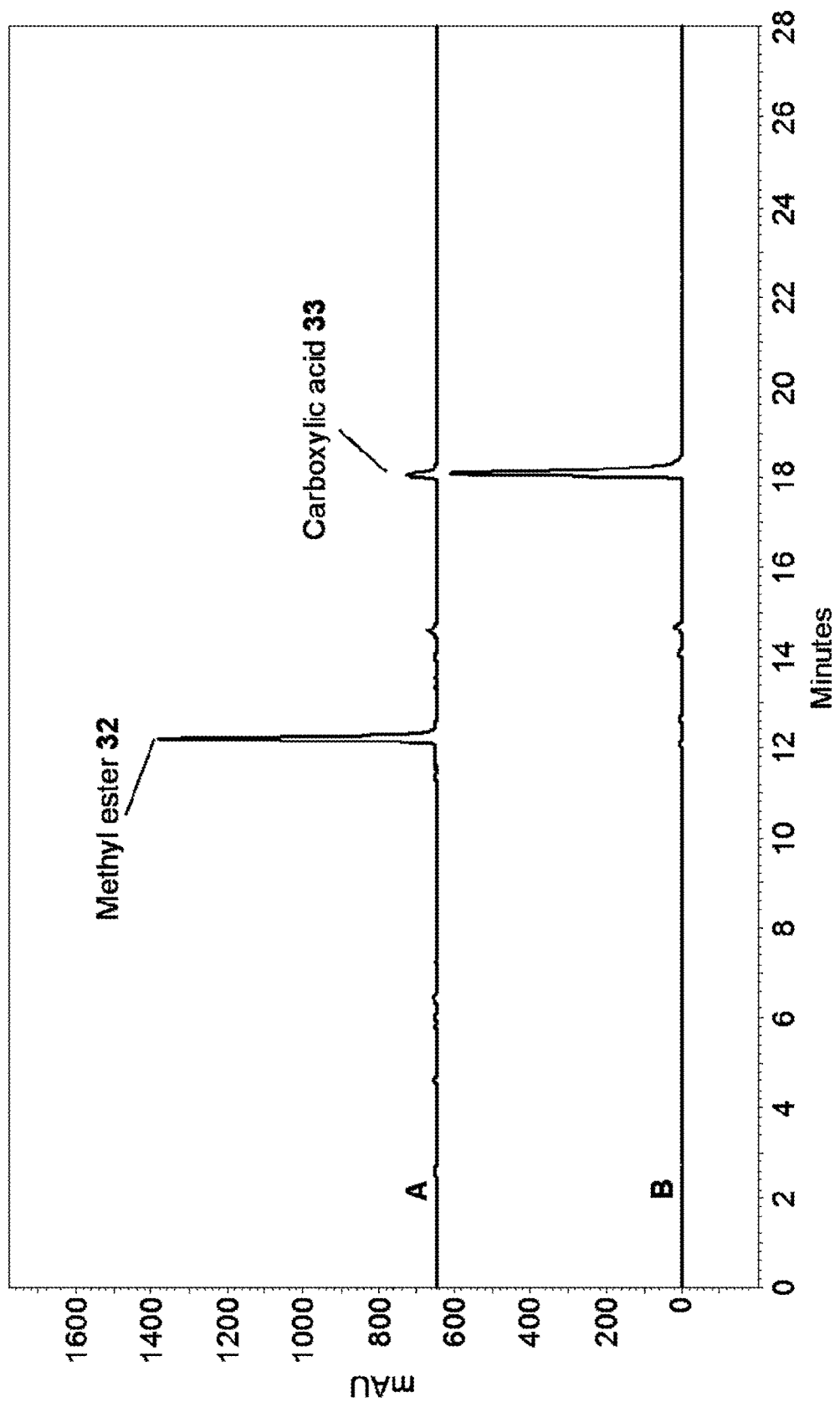
FIG. 7: HILIC analysis of methyl ester 32 (A) and a 10-minute sample of its hydrolysis to carboxylic acid 33 using 0.1M NaOH at room temperature (B).

HILIC monitoring of the cleavage of the neopentyl sulfonate ester of 29 showed minimal formation of byproducts. After the deprotection step the methyl ester of compound 32 was hydrolyzed under basic conditions to form the carboxylic acid, tetra-anionic 33. FIG. 7 shows that hydrolysis was complete after 10 minutes in 0.1M NaOH at room temperature.

Purification of Sulfonic Acid 33 by Semi-Prep HILIC. The first bottleneck in the semi-prep HILIC of tetra-anion 33 was its efficient loading into the column. In preparative chromatography, the sample must be loaded in a solvent that is weaker than the eluent to prevent unnecessary peak broadening. In the HILIC system used, the initial eluent contains 90 to 100% ACN. The amount of the tetra-anionic material that can be dissolved in this solvent is very small, consequently prohibitively large sample volumes would have to be injected to achieve the desired sample loads.

Figure 8:
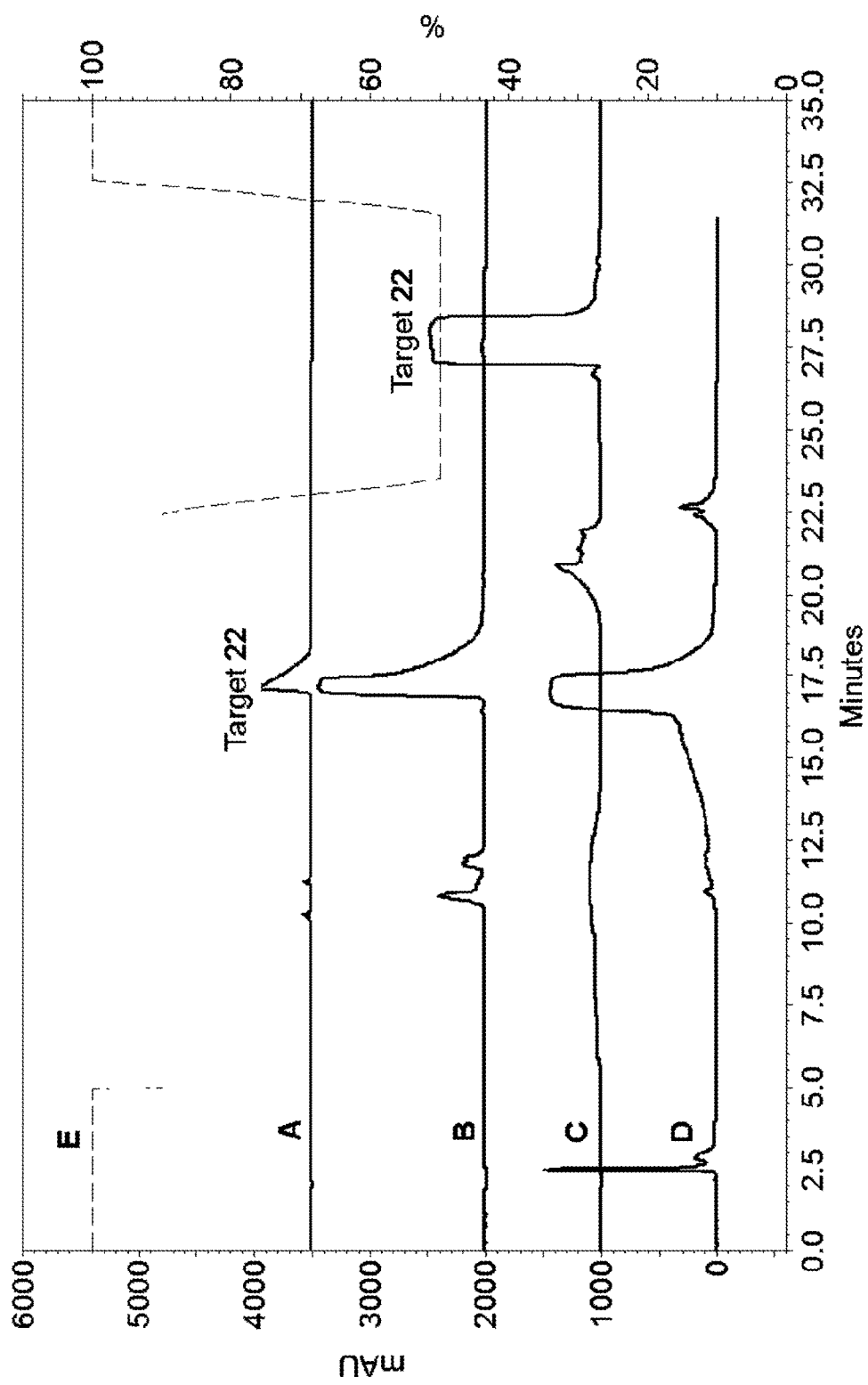
FIG. 8: Semi-prep tests with a Luna HILIC 150 mm×4.6 mm column. The amount and volume of the sample loaded were: 0.1 mg 22 in 0.2 mL mobile phase (A), 1 mg 22 in 2 mL mobile phase (B), 5 mg 22 in 10 mL mobile phase (C) and 2.5 mg 22 in 50 μL water (D). The mobile phase composition (E) is in % B (A: 10 mM $NH_4HCO_2$ in water; B: 10 mM $NH_4HCO_2$ in ACN). Flow rate was 1 mL/min. The flat peak tops are due to detector signal overrange.

To investigate this problem, tri-anionic compound 22 was used as test compound. FIG. 8 is an overlay of the semi-prep HILIC runs obtained with a Luna HILIC 150 mm×4.6 mm column for compound 22. The 5-mg sample had to be loaded in a 10-mL volume due to limited solubility of the highly ionic target in the run eluent (~95% ACN). The step gradient for the 5-mg sample had to be delayed until all of the sample volume was injected into the column adding an additional 10 minutes of elution time for the target peak in (C) lowering throughput. A 2.5-mg sample in a 50 µL volume of pure aqueous solvent was also loaded to see if peak resolution could be maintained without the large sample volume. The peak shape was severely fronting (FIG. 8, trace D) and eliminated altogether the resolution between the target and the early eluting impurities.

To go around this problem, Neue et al. developed a technique that allows the loading of samples which were dissolved in stronger solvent by diluting them at-column (Neue, U. D., Mazza, C. B., Cavanaugh, J. Y., Lu, Z., Wheat, T. E., *Chromatographia* 2003, 57, S121-S127). However, this required the use of an additional HPLC pump and reconfiguration of the HPLC plumbing. A simpler technique was developed to allow maximum loading of a sample prepared in a strong solvent without the need for additional equipment. The idea was to partially fill a sample loop with a plug of the sample in one end and then dilute the plug in-line with the eluent along the length of the loop during injection through Taylor dispersion. The extent of dilution increases with increasing I.D. and length of the sample loop. In the semi-prep HILIC experiments reported here, a 2.0-mL and a 5-mL sample loop, both with a nominal I.D. of 1 mm, were found to be sufficient to effect dilution for a 4.6 mm and 10.0 mm I.D. column, respectively. The sample loop was configured as shown in FIGS. 6A and 6B.

Figure 9:
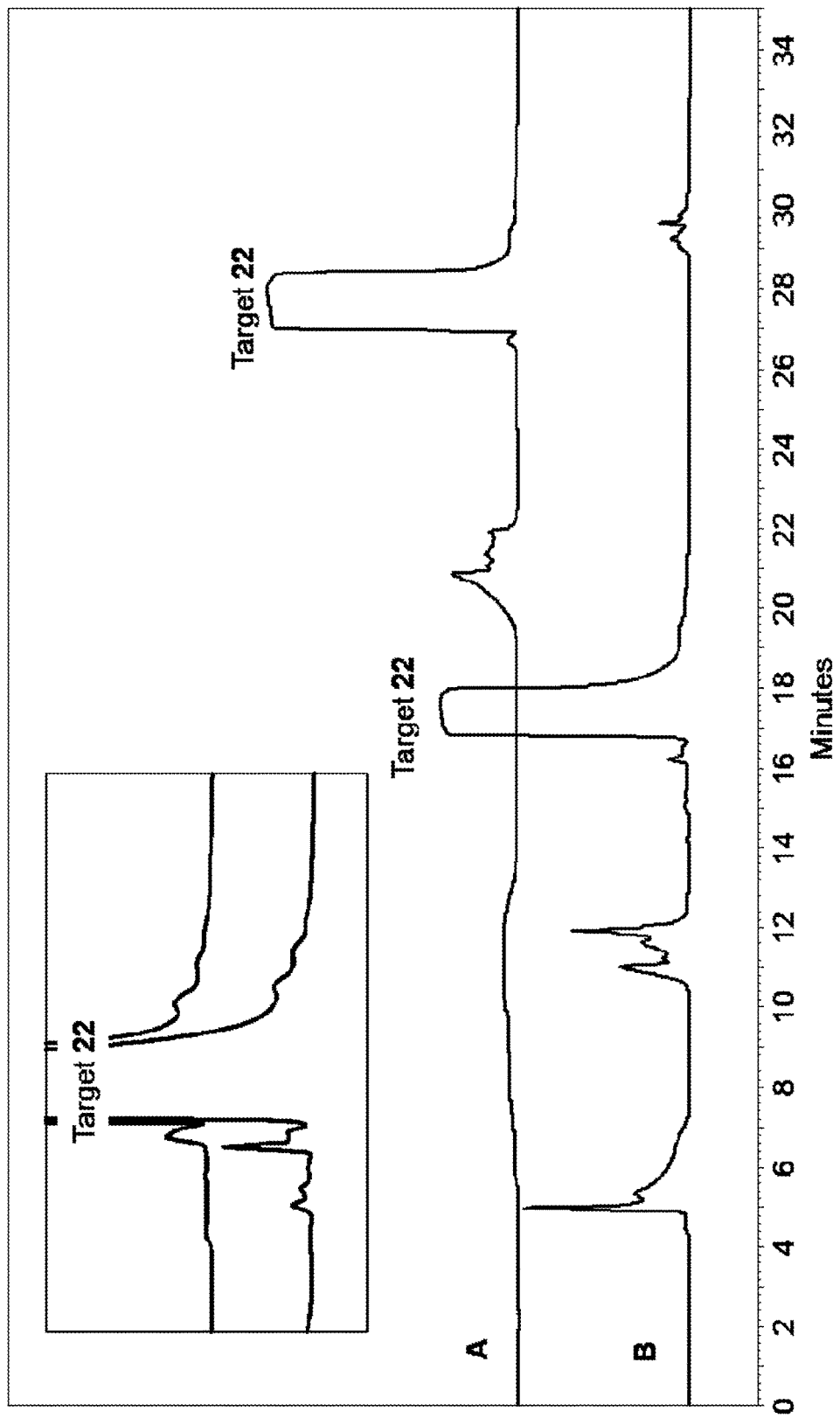
FIG. 9: Semi-prep HILIC separation of 5 mg 22 dissolved in 10-mL mobile phase injected using conventional sample injection (A) and 5 mg 22 dissolved in 50 μL water injected using the Taylor dilution-mediated injection technique (B). In the inset, the target peaks are manually aligned and expanded.

A comparison of a semi-prep HILIC separation of 5 mg 22 dissolved in 10 mL mobile phase and 5 mg 22 dissolved in 50 µL water is shown in FIG. 9. The latter was injected in Taylor dilution mode using a 2.0-mL sample loop. Both runs appear similar, except for the longer elution time for the 10-mL sample. However, a closer look at the impurities (FIG. 9, inset) reveals that the 50 µL injection with Taylor dilution had much better defined impurity peaks (i.e., these peaks were less broadened and thus better resolved from the target peak).

Figure 10:
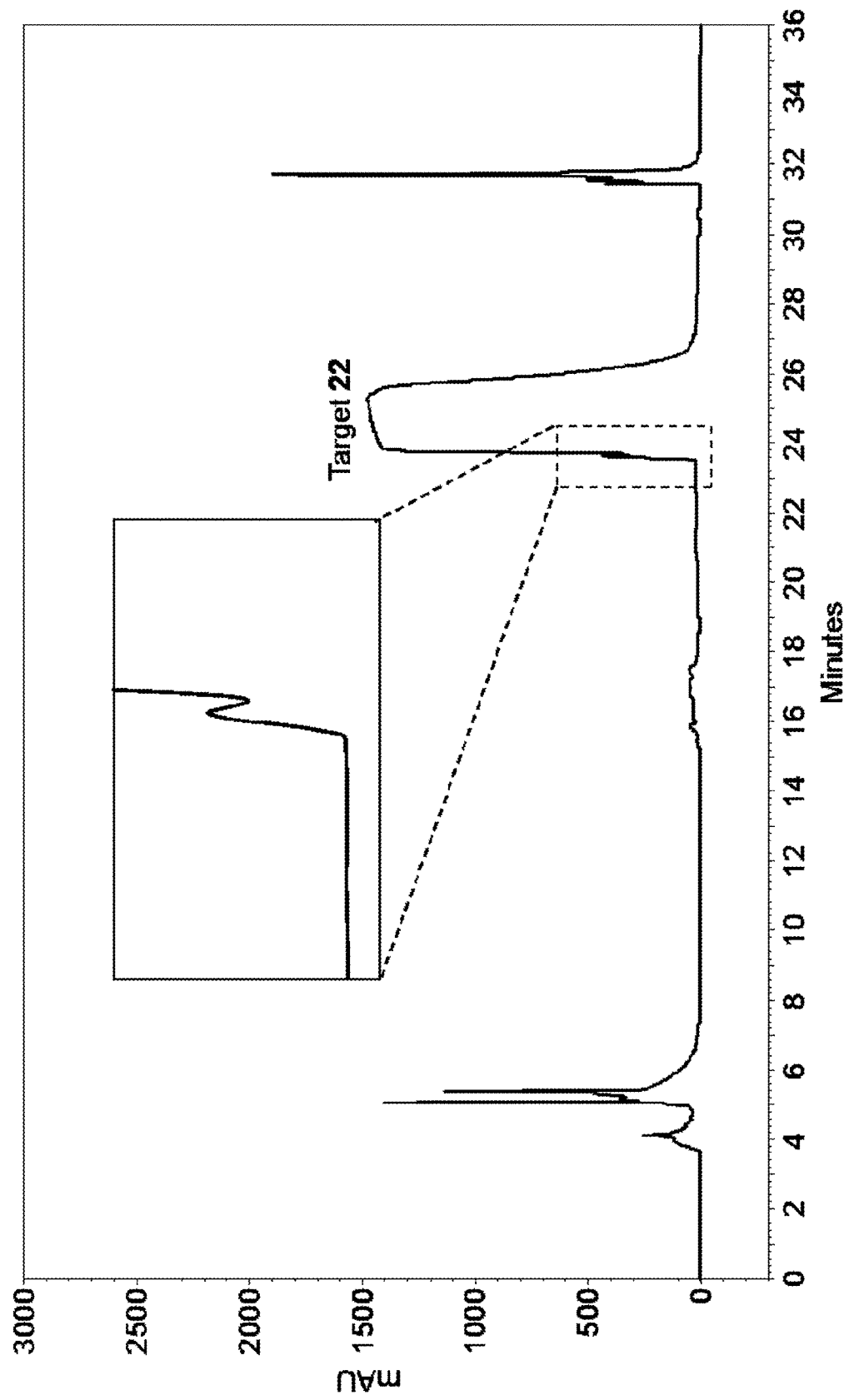
FIG. 10: Semi-prep HILIC separation of 45 mg 22 dissolved in 200 μL, water using Taylor dilution-mediated injection. Inset: expanded view of the front end of the target peak showing a partially resolved impurity peak.

The Taylor dilution-mediated injection technique was then applied with a 10.0 mm I.D. HILIC column using a 5.0-mL sample loop. The sample injected was 45 mg 22 in 200 µL water. FIG. 10 shows a well defined target peak shape that is favorable for fractionation. An early eluting impurity peak is partially resolved (see inset). A conventional injection technique would have required the injection of a 90 mL sample, taking about 20 minutes.

Figure 11:
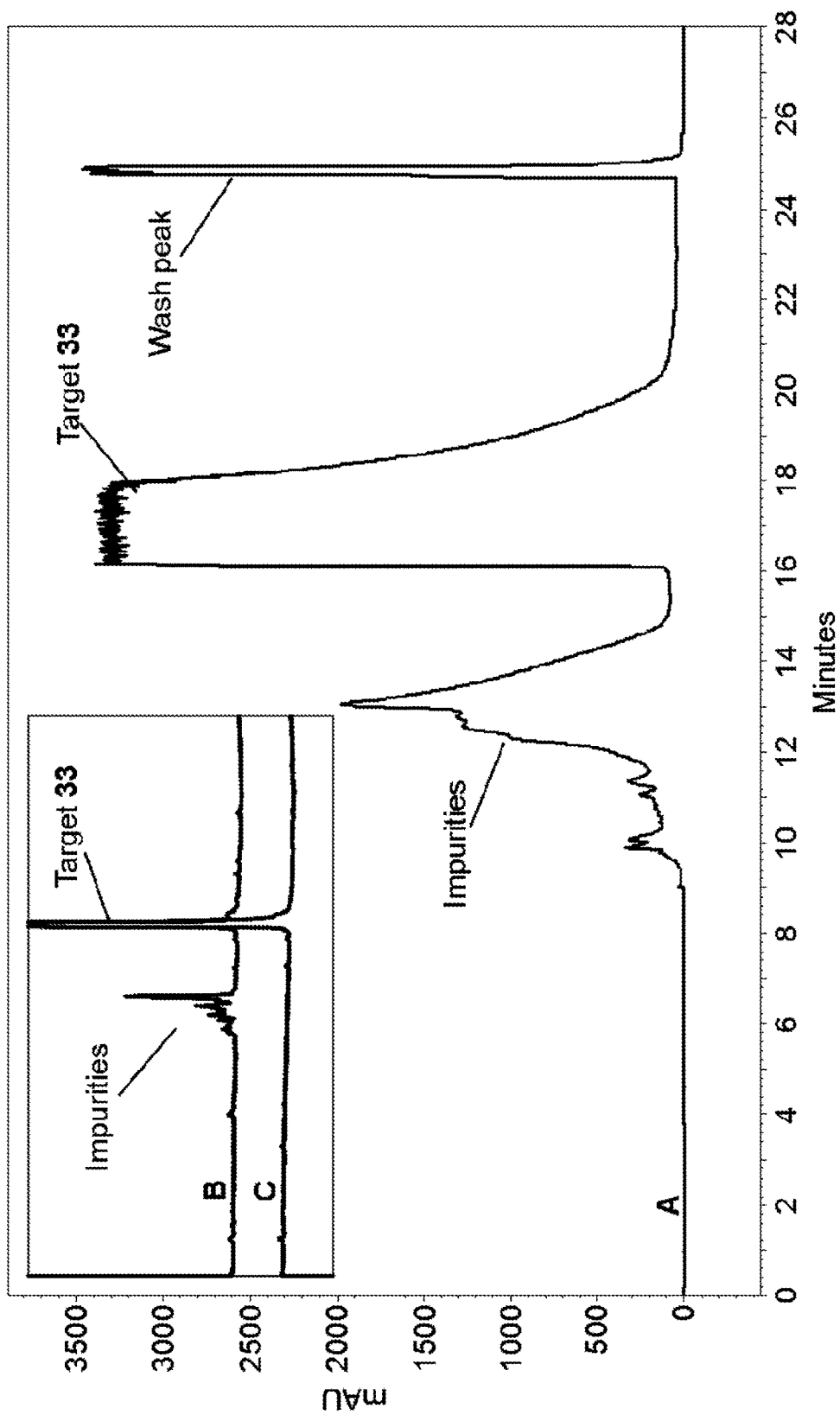
FIG. 11: Semi-prep HILIC separation of 33 (A). Inset shows the analytical HILIC separation of the crude (B) and the fractionated material (C). The target peaks are normalized.

Compound 33 was purified using semi-prep HILIC. To facilitate the removal of the buffer component from the target after fractionation, sodium trifluoroacetate (NaTFA) was used in place of ammonium formate in the HILIC eluent. Since NaTFA is soluble in ACN and the sodium salt of 33 is not, a simple precipitation from ACN can recover the target from the fractions. FIG. 11 shows a semi-prep HILIC separation of 50 mg 33 dissolved in 200 µL water. Because the peaks were well defined, fractionation of the target peak was facile. The inset shows improvement in the purity of the target from 89% (crude) to 99.7% (fractionated material).

Example 4: Spectral Properties of a Sulfonic Acid Fluorophore 33

Fluorophore 33 was designed to have an $\lambda_{max}^{em}$ that is compatible with the 488 nm line of the argon ion laser. It was also developed to have pH-independent fluorescence properties which are important for CE applications. The fluorescence spectra of 33 were recorded in aqueous buffers having different pH values in order to determine if pH had any influence on the fluorescence intensity and $\lambda_{max}^{em}$ of 33. The molar absorbance and relative quantum yield values were also determined using Rhodamine 6G as a standard.

UV absorbance spectra were recorded using a Beckman 168 photodiode detector during the HILIC separations. The eluent compositions at the time of detection were 26 mM $NH_4HCO_2$ 74% ACN/water for APTS, 24 mM $NH_4HCO_2$ 76% ACN/water for trisulfonamide 22 and 10 mM MOPS with 5 mM NaOH in 76% ACN/water for 33. Fluorescence spectra at different pH values were recorded on a Shimadzu RF-5301PC spectrofluorometer. The buffers used are tabulated below:

TABLE 1

Buffers used in the fluorescence versus pH experiments for compound 33.

| pH | Composition | Ionic Strength |
|---|---|---|
| 2.4 | 10.2 mM trifluoroacetic acid/5 mM NaOH | 10 |
| 3.5 | 25 mM formic acid/10 mM LiOH | 10 |
| 4.1 | 50 mM acetic acid/10 mM BisTris | 10 |
| 5.5 | 50 mM MES/10 mM LiOH | 10 |
| 7.1 | 20 mM MOPS/10 mM LiOH | 10 |
| 8.0 | 13 mM HEPES/10 mM LiOH | 10 |
| 9.0 | 50 mM boric acid/20 mM NaOH | 20 |
| 10.0 | 25 mM N,N-diethylethanolamine/10 mM formic acid | 10 |
| 11.2 | 30 mM piperidine/7 mM acetic acid | 10 |

UV absorbance and fluorescence spectra for the quantum yield determinations were acquired using a Varian 100 Bio UV-Vis spectrophotometer and a Varian Cary Eclipse fluorescence spectrometer, respectively. The samples were dissolved in a pH 9 0.1M aqueous sodium bicarbonate buffer.

Figure 12:
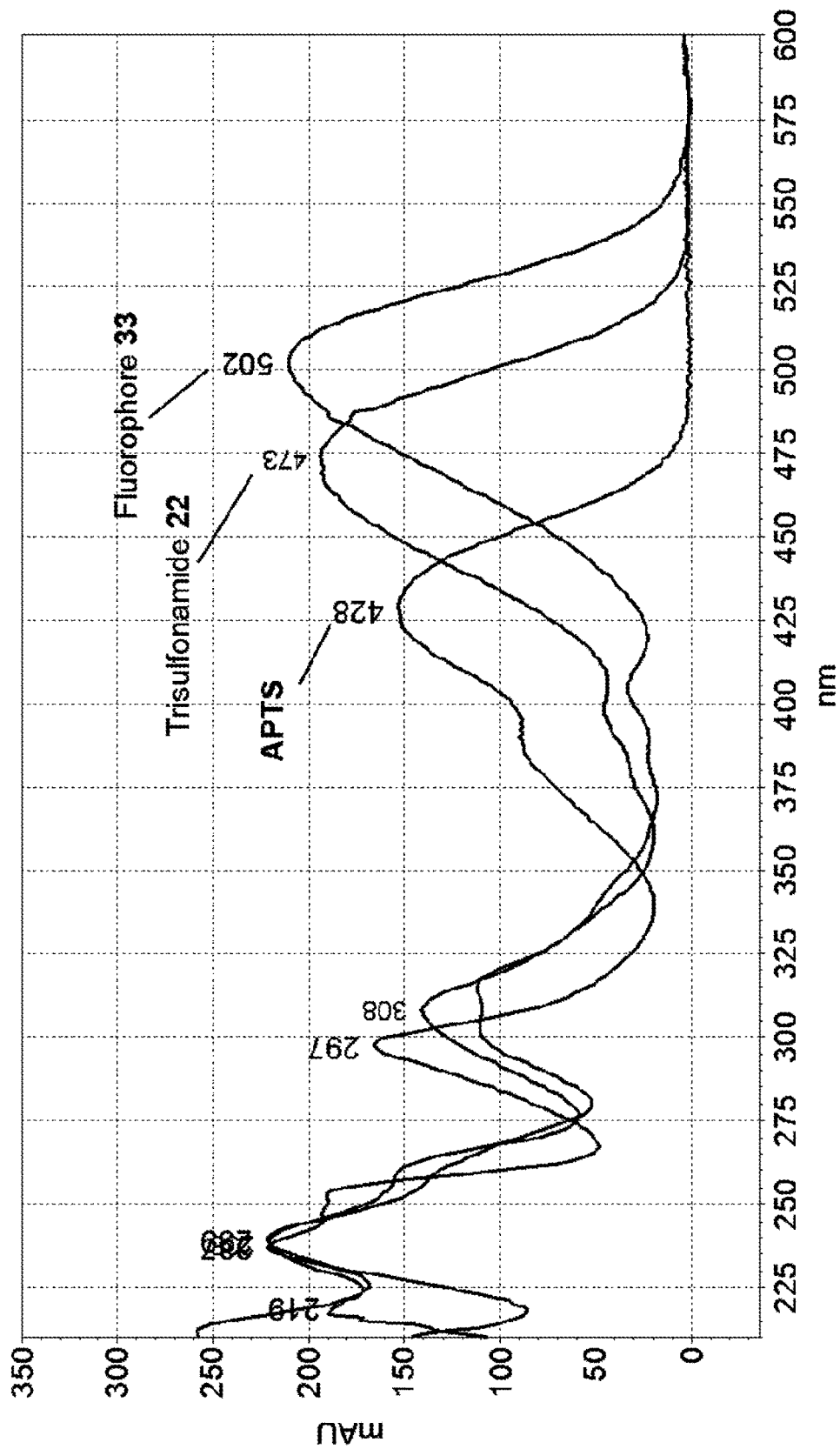
FIG. 12: Overlay of the UV absorbance spectra of APTS, trisulfonamide 22 and alkylated trisulfonamide fluorophore 33.

The UV absorbance spectra of fluorophore 33, APTS (starting material) and 22 (trisulfonamide intermediate) are overlaid in FIG. 12. As anticipated, $\lambda_{max}^{ex}$ of the fluorophore increased with each modification of the functional groups on the pyrene ring. Sulfonamidation and alkylation increased $\lambda_{max}^{ex}$ to 502 nm. About 91% of the maximum molar absorbance can be harnessed at 488 nm.

Figure 13:
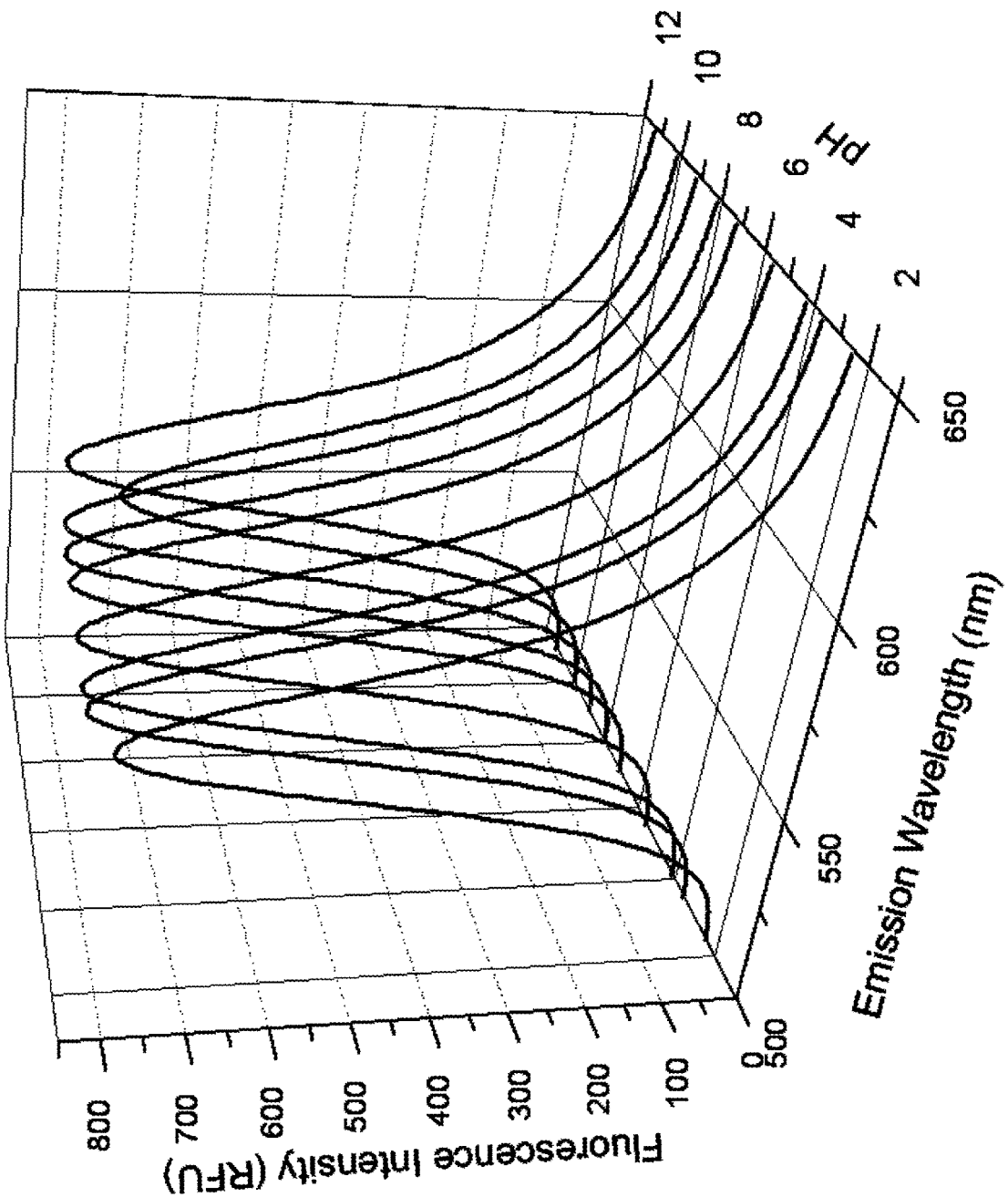
FIG. 13: Fluorescence spectra of fluorophore 33 at different pH values.

The fluorescence emission spectra of fluorophore 33 are virtually the same across the pH range as indicated in FIG. 13. Moreover, $\lambda_{max}^{em}$ is constant at 559 nm across the entire pH range. Fluorescent intensity in the spectrum taken at pH 10 is slightly lower than in the ones at the neighboring pH values and may have been caused by a matrix effect that was specific for the buffer that was used. The molar absorbance of fluorophore 33 at 510 nm, $\epsilon^{510\ nm}$, was determined, yielding a $\epsilon^{510\ nm}$ of about 32,000 cm$^{-1}$ M$^{-1}$. The relative fluorescence quantum yield was also determined with Rhodamine 6G as standard and found to be 0.74, which is typical for pyrene-based fluorophores.

Example 5: Fluorescence Labeling Tests with Fluorophore 33

The utility of the fluorescent label in free zone capillary electrophoresis (CZE) was investigated. Small amines, 4-(2-aminoethyl)morpholine and N-methylpiperazine were labeled and analyzed by CZE in different pH BGEs to determine the effect of the latter on the fluorescence of the label. Proteins of different sizes were also labeled and separated by SDS-CGE. The effect of labeling on the migration time of the proteins through the sieving matrix was investigated.

Materials and Methods. Pentafluorophenyl trifluoroacetate, 4-(2-aminoethyl)morpholine, N-methylpiperazine, polyvinylpyrrolidone (360 kDa), α-lactalbumin (Type III: calcium depleted from bovine milk, 85%), carbonic anhydrase (from bovine erythrocytes), chicken egg ovalbumin and bovine serum albumin were all purchased from Sigma Aldrich. SDSMW kits for the SDS-CGE separation of proteins were provided by Beckman Coulter. Ultrafree®-MC (10,000 NMWL, Biomax-10) centrifugal filter units were acquired from Millipore. CE separations were completed in a PA800 system with a 488 nm argon ion LIF detector.

Activation of Fluorophore 33 as a Pentafluorophenyl Ester. 7 μL of pentafluorophenyl trifluoroacetate, 385 μL anhydrous DMF and 11.5 μL triethylamine were mixed in a 1.5-mL Eppendorf tube. The mixture was immediately added to 10 mg of fluorophore 33. After 2.5 hours at room temperature, MTBE was added, the slurry was centrifuged and the solids were washed with THF. The residue was dissolved in 100 μL DMSO and used as-is as an amine-reactive fluorescent labeling reagent.

Labeling of Small Diamines. A diamine sample containing 1 mM each of 4-(2-aminoethyl)morpholine and N-methylpiperazine in a buffer made from 50 mM boric acid and 20 mM sodium hydroxide was prepared. A 2 μL portion of the activated fluorophore solution in DMSO was added to 40 μL of the diamine mixture and allowed to react at room temperature for 30 minutes. The reaction mixture was then quenched with 3.2 μL of 0.25 M taurine in 0.1M sodium hydroxide solution and allowed to stand for 5 minutes. The mixture was then analyzed by CE-LIF by diluting a 0.5 μL aliquot with 50 μL of 1:3 mixture of BGE:water.

CE-LIF of Small Diamines. CE-LIF was carried out in a fused silica capillary (50 μm I.D/360 μm O.D; 20.35 cm/30.39 cm inlet-to-detector length/total length) having a semi-permanent internal coating. The new capillary was first preconditioned by flushing, sequentially, with water for 2 min, 0.1M NaOH for 3 min, 0.1M HCl for 3 min, water for 3 min, a 2% polyvinylpyrrolidone (360 kDa PVP) solution in water for 2 min and background electrolyte (BGE) for 1 min. All rinses were done at a pressure of 50 psi. The inlet and outlet of the capillary were then immersed in the BGE vials and a potential of 20 kV (negative-to-positive polarity) was applied for 10 min. Before each CE separation, the capillary was sequentially rinsed with water for 0.5 min, the 2% PVP solution for 1 min and the BGE for another 1 min, all at 50 psi. The sample was then injected by pressure at 0.5 psi for 3 sec and separated by applying 20 kV (negative-to-positive polarity). The BGEs used for the CE separations are tabulated below:

TABLE 2

Background electrolytes used for the CE analysis of small diamines.

| pH | Composition | Ionic Strength |
|---|---|---|
| 2.4 | 10.2 mM trifluoroacetic acid/5 mM NaOH | 10 |
| 4.1 | 50 mM acetic acid/10 mM BisTris | 10 |
| 6.1 | 20 mM histidine/10 mM propionic acid | 10 |
| 7.1 | 20 mM MOPS/10 mM LiOH | 10 |
| 8.0 | 13 mM HEPES/10 mM LiOH | 10 |
| 10.0 | 13 mM CHES/10 mM formic acid | 10 |

Labeling of Proteins for SDS-CGE-LIF. A 50 μL portion of each 5 mg/mL protein solution in 0.1M sodium carbonate/bicarbonate buffer (pH 9) was added to the necessary amount of activated fluorophore. 1:1 and 10:1 tag-to-protein labeling ratios were tried. The labeling reactions were allowed to proceed for 20 min at room temperature. A 20 μL aliquot of each of the labeled protein mixture was then loaded into a 10,000 NMWL centrifugal filter unit followed by 200 μL of 0.1M sodium bicarbonate buffer. The units were centrifuged until approximately 10 to 20 μL of solution was left. This process of dilution and centrifugation was repeated twice for the 1:1 tag-to-protein labeling reactions and 5 times for the 10:1 tag-to-protein labeling reactions. The final protein solutions retained above the membrane were diluted with 100 μL of Beckman SDSMW sample buffer, mixed with 5 μL 2-mercaptoethanol and heated at 100° C. in a closed vial for 3 minutes. The solutions were cooled to room temperature and analyzed by SDS-CGE by diluting a 2 μL portion with a 100 μL aliquot of Beckman SDSMW run buffer. SDS-CGE was carried out using the Beckman SDSMW protocol and the 488 nm LIF detector. The separation capillary was a bare fused silica capillary having the following dimensions: 50 μm I.D., 360 μm O.D. and 30.2 cm/20.0 cm total/inlet-to-detector lengths. The capillary was preconditioned as recommended by Beckman for their SDS-MW analysis. Briefly, the capillary was rinsed with a 0.1M aqueous sodium hydroxide solution at 50 psi for 5 min. This was followed by a 50 psi rinse with a 0.1M aqueous hydrochloric acid solution for 2 min, then a 50 psi rinse with deionized water for 2 min. The capillary was then filled with the SDS-MW gel buffer solution at a pressure of 40 psi for 10 min. A 15.0 kV potential was applied (negative-to-positive polarity), with a ramp up time of 5 min and a 20 psi nitrogen blanket on both the inlet and outlet vials.

The SDS-CGE separation was performed by first introducing the protein sample by electrokinetic injection at 5.0 kV for 20 sec. Then the sample was separated by applying 15.0 kV with a 1 min ramp up time and 20 psi of pressure applied on both the inlet and outlet vials.

Figure 14:
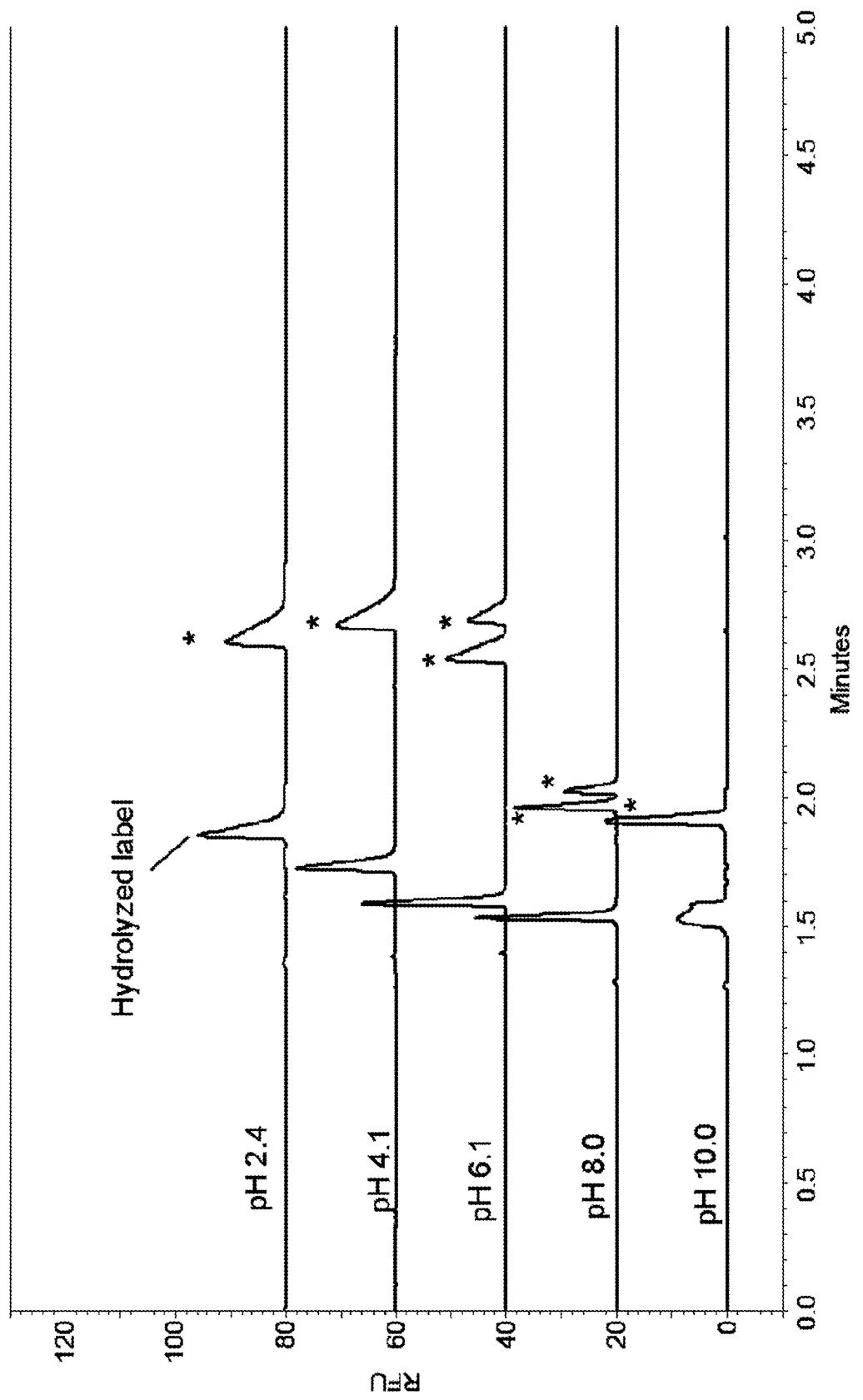
FIG. 14: CE-LIF of labeled 4-(2-aminoethyl)morpholine and N-methylpiperazine (both marked with *) at different pH values.

Results and Discussion. Labeling of the small diamines produced the expected labeled species without the formation of byproducts. The labeled diamines were analyzed in different BGEs having pH values that were evenly spread across the operating pH range of CE. Separations were obtained with negative-to-positive polarity in a capillary that had a semi-permanent coating to suppress electroosmotic flow. Of all the components, hydrolyzed fluorophore 33 is expected to have the highest anionic mobility at any pH due to its smallest size and highest anionic charge. This is evident in FIG. 14 where the electropherograms of the same labeled diamine sample obtained at different pH values are overlaid. It is also clear from these electropherograms that the fluorescence signal stays basically the same across the pH range, irrespectively of the components of the BGE. The relative peak areas of the hydrolyzed fluorophore and the labeled diamines stay almost the same for all the runs (53±1.5 and 47±1.5). The pH scan was used to determine the approximate optimum pH for the separation of the diamines (marked with *). The diamines have good separation selectivity at pH 6.1 and 8.0 ($\alpha_{pH6.1}$=1.05, $\alpha_{pH8.0}$=1.03) but co-migrate outside this pH range. An intermediate pH of around 7 may therefore provide the optimum selectivity.

Figure 15:
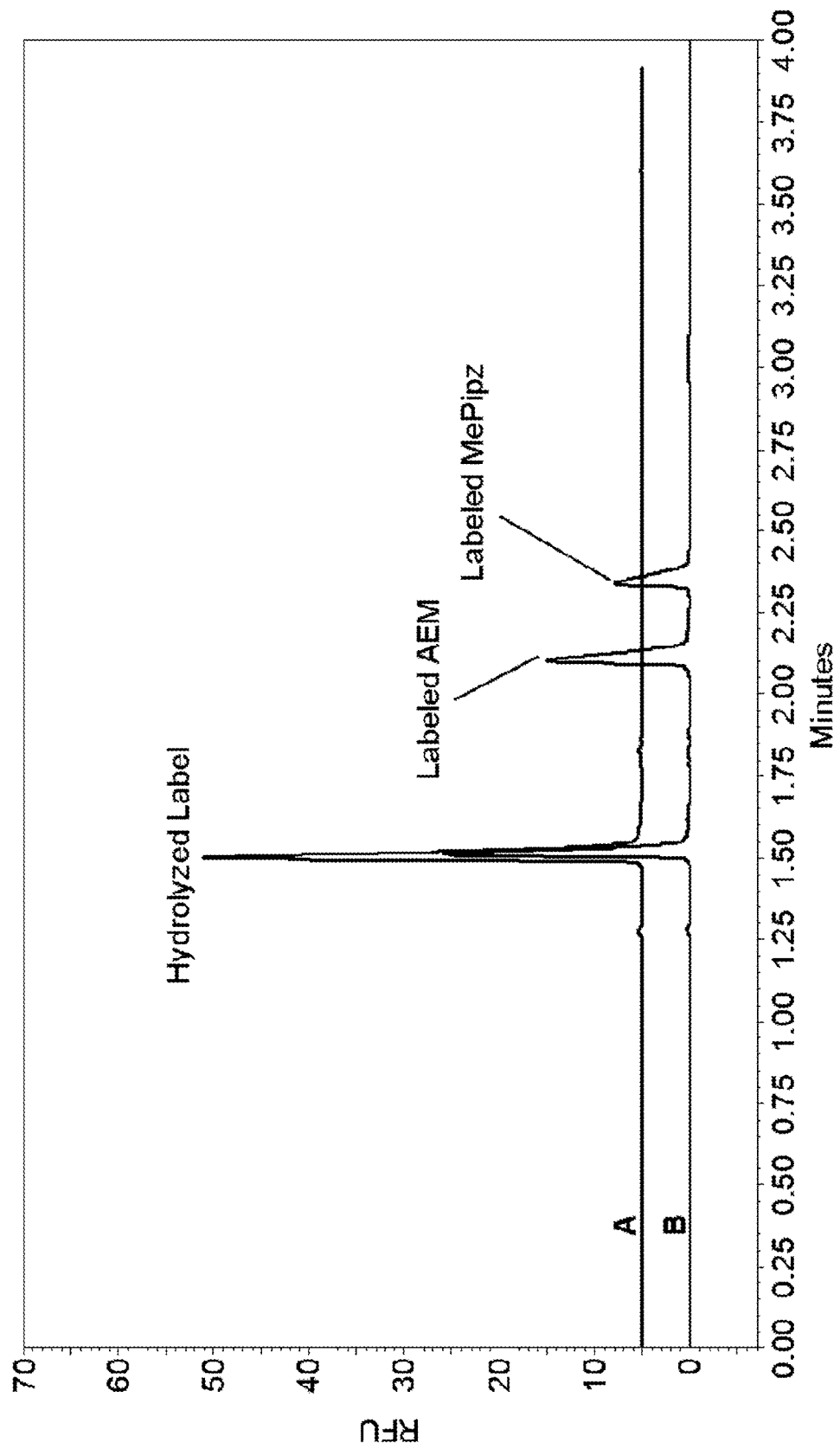
FIG. 15: CE-LIF of a blank labeling reaction (A) and the labeled diamine mixture (B) at pH 7.1.

At pH 7.1, separation selectivity for the labeled diamines is as high as $\alpha_{pH7.1}$=1.11 (FIG. 15). The calculated $LOD_{S/N=3}$ for the labeled AEM is about 5 nM. For an injected volume of about 5 nL, the loaded amount of the analyte is in the low attomol range.

Figure 16:
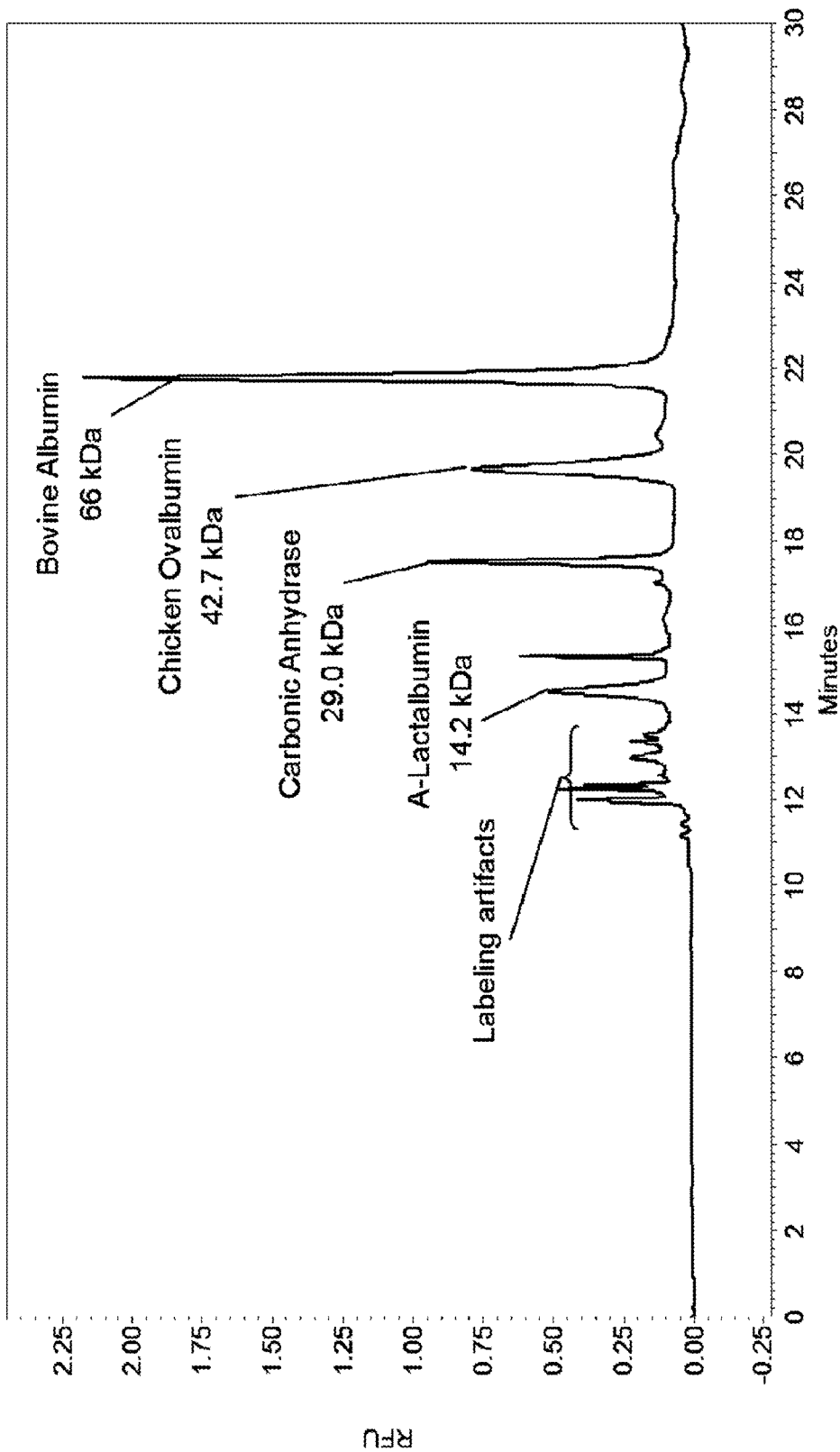
FIG. 16: SDS-CGE of a mixture of proteins individually labeled at a tag-to-protein ratio of 1:1.

Proteins α-lactalbumin, carbonic anhydrase, chicken ovalbumin and bovine serum albumin were also labeled with the PFP activated fluorophore. Individual protein labeling reactions at both 1:1 and 10:1 tag-to-protein ratios (mol:mol) were carried out. The electropherogram of a sample containing each of the labeled proteins is shown in FIG. 16. The logarithm of protein molecular weight (log MW) was plotted against their corresponding migration times ($T_m$) showed the expected linear correlation between log MW and $T_m$. This suggests that the migration behavior of the labeled proteins was not adversely affected when the tag-to-protein labeling ratio was 1:1.

Figure 17:
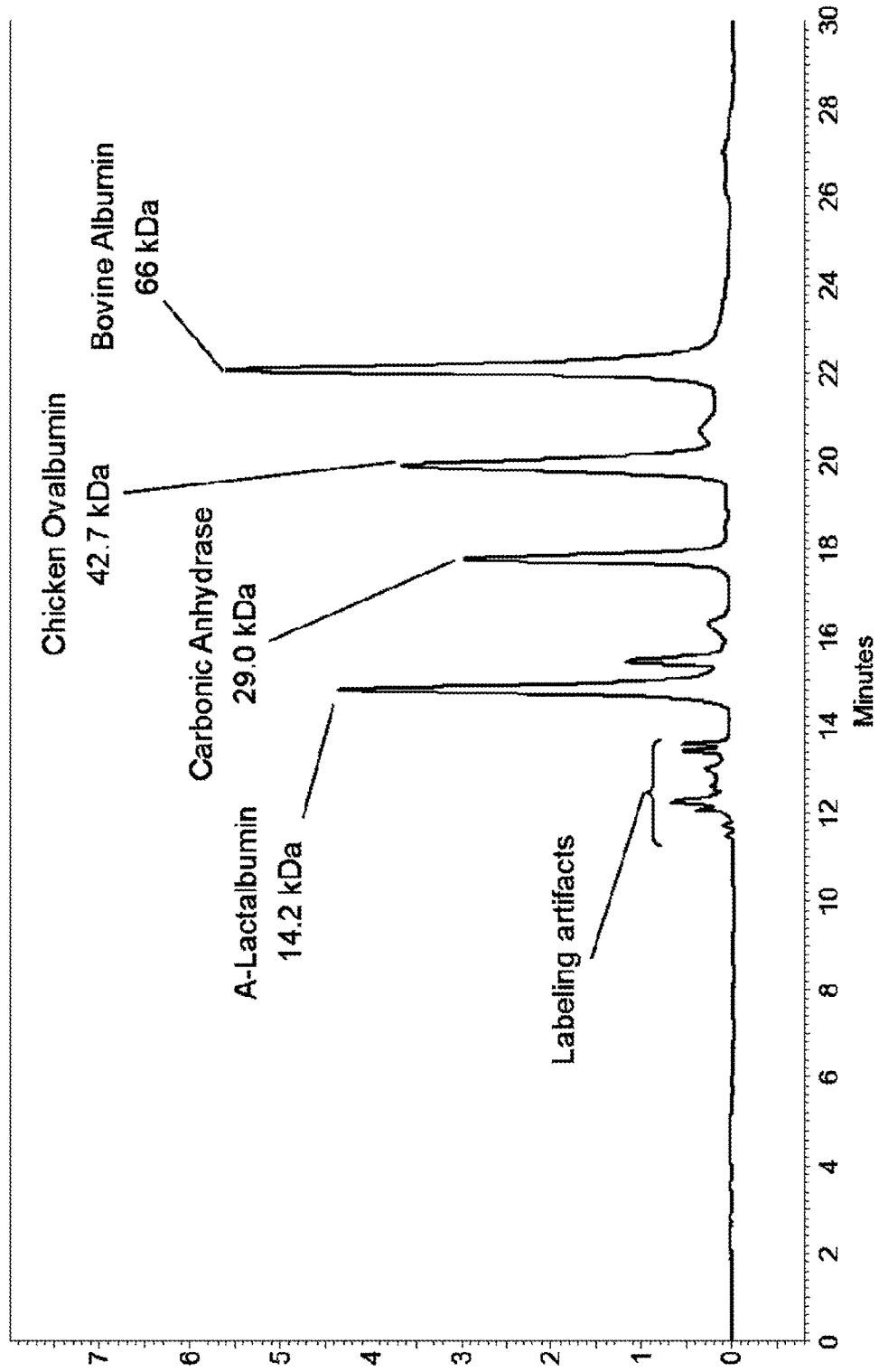
FIG. 17: SDS-CGE of a mixture of proteins individually labeled at a tag-to-protein ratio of 10:1.

Increasing the tag-to-protein ratio in the labeling reaction can increase the response factor for the proteins. Therefore, labeling reactions at a 10:1 ratio were also attempted. A mixture of these labeled proteins was prepared and analyzed by SDS-CGE-LIF (FIG. 17). The response factors increased for every protein, although at different rates. The $LOD_{S/N=3}$ values for the 1:1 labeling ratio were between 80 to 140 ng/mL except for α-lactalbumin which was about 1 μg/mL. For the 10:1 labeling ratio, the $LOD_{S/N=3}$ values were between 20 to 40 ng/mL.

Log MW and $T_m$ from the above SDS-CGE separations were then plotted to see if the higher label incorporation rates had any effect on protein migration, and the plot was still linear at this higher label-to-protein ratio. The slope and y-intercept values for both the 1:1 and 10:1 labeling ratios were almost the same.

Example 6: Design and Synthesis of Cleavable Anchors

Materials and Methods. Tetra(ethylene glycol), 4-hydroxybenzaldehyde, benzylacetone, sodium azide, sodium hydride (60% dispersion in oil), p-toluenesulfonyl chloride (tosyl chloride) and p-toluenesulfonic acid monohydrate (PTSA) were purchased from Sigma Aldrich. Glycerol was from EM Science. Xterra® MS C18 HPLC column was acquired from Waters. Gemini C18 column was from Phenomenex. HPLC analyses were done in a Beckman HPLC system equipped with a 508 autosampler, 126 pump and 168 photodiode array detector.

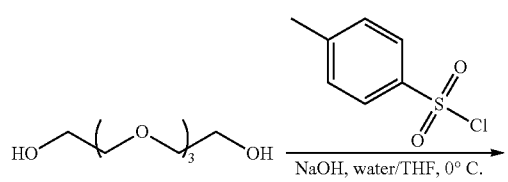

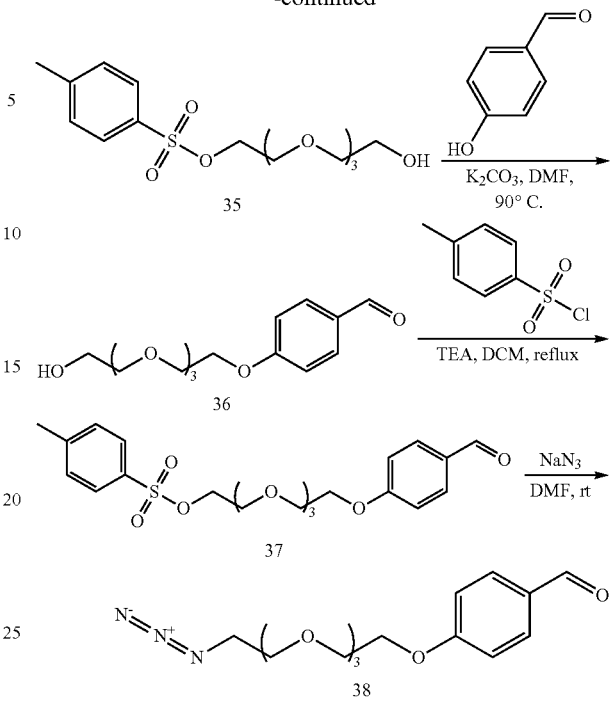

Synthesis of Monotosylated Tetra(ethylene glycol) 35. Compound 35 was prepared by a procedure similar to what was outlined by Ashton and others (Ashton, P. R., Huff, J., Menzer, S., Parsons, I. W., et al., *Chemistry-a European Journal* 1996, 2, 31-44). 175.6 g (904 mmol) tetra(ethylene glycol) and 25 mL THF were charged into a 3-neck 500-mL flask. While mechanically stirred in an ice bath, a mixture of 5.47 g (137 mmol) of NaOH and 30 mL water was incrementally added to the solution. The temperature increased to 30° C. due to the addition. After the temperature went back down to 3° C., 16.7 g (87.6 mmol) of tosyl chloride in 90 mL THF was added, while stirring vigorously, in the span of 1.5 hours using a syringe pump. Stirring was continued for an additional 2 hours in the ice bath. The reaction was monitored by RP-HPLC. 500 mL of ice water was dumped into the reaction mixture. The hazy mixture was extracted three times with 100 mL dichloromethane. The organic phases were combined and washed twice with 50 mL water. The dichloromethane solution was dried with sodium sulfate and the solvent was removed under vacuum to afford a colorless oil (27.37 g, 90% yield). HPLC was done using an Xterra® MS C18 column (3.5 μm, 150 mm×2.1 mm) with a binary gradient of 30% to 70% B in 20 min at 0.3 mL/min (A: water; B: ACN). $^1$H-NMR (300 MHz, CDCl$_3$) δ 7.76 (d, 2H), 7.30 (d, 2H), 4.12 (t, 2H), 3.70-3.49 (m, 14H), 2.84 (s, 1H), 2.40 (s, 3H).

Synthesis of Tetra(ethylene glycol)-decorated 4-Hydroxybenzaldehyde 36. 80 g (230 mmol) of the monotosyl derivative of tetra(ethylene glycol), 35, 30 g (246 mmol) p-hydroxybenzaldehyde and 500 mL DMF were put together in a 2-L round bottom flask, followed by the addition of 93 g (673 mmol) potassium carbonate. The reaction mixture was placed in a heating mantle and its temperature was increased to 90° C. in 30 minutes while stirring with a mechanical stirrer. The reaction was complete in 60 minutes as determined by RP-HPLC. The mixture was allowed to cool and most of DMF was removed under reduced pressure. The resulting residue was partitioned between 1 L dichloromethane and 1 L water. The organic phase was then extracted twice with 1 L 10% aqueous sodium chloride. The dichloromethane solution was then evaporated under vacuum leaving a brownish oil having an assay purity of 90% with p-hydroxybenzaldehyde as the main contaminant. This oil was extracted using a solvent system consisting of 500 mL ACN, 50 mL toluene and 1 L water. The aqueous bottom phase contained 70% of the target as determined by HPLC and was set aside. The top phase was mixed with 400 mL ACN and 1 L water, allowed to form two phases and separated. The aqueous phases from the two extraction steps were combined and the solvent was removed under reduced pressure to give a light brown oil (56.1 g, 96.5% yield). HPLC was carried out using a Gemini C18 column (3 μm, 100 Å, 75 mm×4.6 mm) with a binary gradient of 20% to 70% B in 15 min at 1 mL/min (A: 2 mM N-methylmorpholine and 1 mM acetic acid in water; B: 2 mM N-methylmorpholine and 1 mM acetic acid in ACN). $^1$H-NMR (300 MHz, CDCl$_3$) δ 9.75 (s, 1H), 7.71 (d, 2H), 6.91 (d, 2H), 4.10 (t, 2H), 3.76 (t, 2H), 3.63-3.50 (m, 10H), 3.47 (t, 2H), 3.16 (broad s, 1H); $^{13}$C-NMR (300 MHz, CDCl$_3$) δ 190.8, 163.8, 131.9, 129.9, 114.8, 72.5, 71.2, 70.7, 70.5, 70.4, 70.36, 70.15, 69.3, 67.7, 61.5 (extra two peaks in the alkyl region).

Synthesis of Tosylated Aldehyde 37. 56 g (188 mmol) of 36 was dissolved in 500 mL dichloromethane. 72.3 g (379 mmol) tosyl chloride was then added followed by 105 mL (755 mmol) triethylamine. The mixture was heated to reflux for 2 hours. After determining by HPLC that conversion of 36 was complete, 38 mL (113 mmol) N,N-diethylethanolamine was added to quench excess tosyl chloride and reflux was continued for 40 more minutes. The reaction mixture was cooled to room temperature and extracted twice with 500 mL aqueous monosodium phosphate, then twice with 500 mL water to extract N,N-diethylethanolamine and its tosyl ester into the aqueous phase. The dichloromethane phase was dried with sodium sulfate and the solvent was removed under reduced pressure affording an oil having an HPLC assay purity (detection at 265 nm) of 90% (85.7 g, 90% yield). HPLC was carried out using a Gemini C18 column (3 μm, 100 Å, 75 mm×4.6 mm) with a binary gradient of 20% to 80% B in 18 min at 1 mL/min (A: 2 mM N-methylmorpholine and 1 mM acetic acid in water; B: 2 mM N-methylmorpholine and 1 mM acetic acid in ACN). $^1$H-NMR (300 MHz, CDCl$_3$) δ 9.80 (s, 1H), 7.74 (t, 4H), 7.27 (d, 2H), 6.95 (d, 2H), 4.15 (t, 2H), 4.08 (t, 2H), 3.82 (t, 2H), 3.68-3.49 (m, 10H), 2.36 (s, 3H); $^{13}$C-NMR (300 MHz, CDCl$_3$) δ 190.8, 163.8, 144.8, 132.8, 131.9, 129.9, 129.8, 127.9, 114.9, 70.6, 70.56, 70.51, 70.45, 69.4, 69.3, 68.6, 67.7, 21.6.

Synthesis of Azido Aldehyde 38. 85 g (~180 mmol) tosylate 37 was mixed with 55 g (85 mmol) sodium azide in 500 mL DMF. The mixture was stirred at 65° C. for 20 minutes and at room temperature overnight. DMF was then removed under reduced pressure. The resulting residue was partitioned between 300 ml dichloromethane and 300 mL water. The dichloromethane phase was washed with 300 mL water and then with 450 mL 7% aqueous sodium chloride. The organic phase was dried with sodium sulfate and the solvent removed under reduced pressure to produce a light brown oily residue (60.7 g, ~100% yield). HPLC was carried out the same way as 37 above. $^1$H-NMR (300 MHz, CDCl$_3$) δ 9.81 (s, 1H), 7.76 (d, 2H), 6.96 (d, 2H), 4.15 (t, 2H), 3.82 (t, 2H), 3.69-3.57 (m, 10H), 3.31 (t, 2H); $^{13}$C-NMR (300 MHz, CDCl$_3$) δ 190.8, 163.8, 131.9, 129.9, 114.8, 72.3, 70.8, 70.59, 70.57, 70.0, 69.4, 67.7, 50.6.

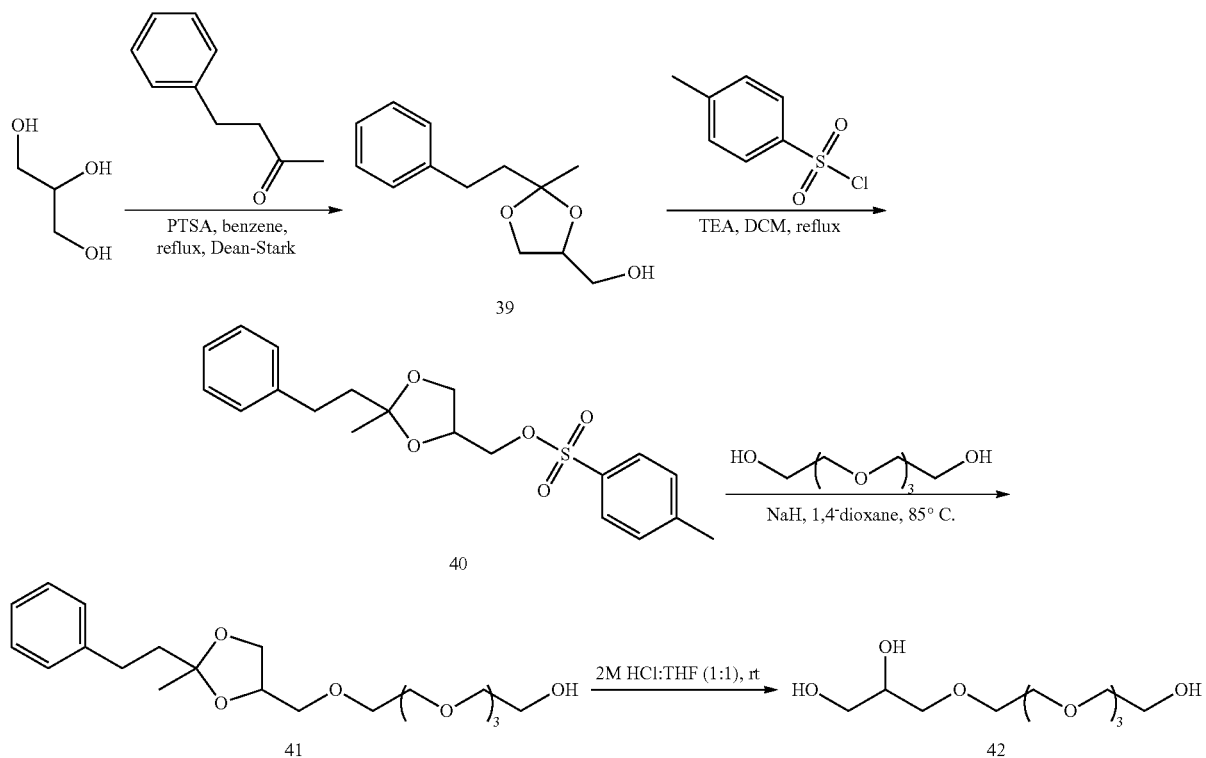

Synthesis of Dioxolane 39. 15 g (101 mmol) benzylacetone, 45 g (489 mmol) glycerol and 0.194 g (1 mmol) p-toluenesulfonic acid were added to 200 mL benzene in a 500 mL round bottom flask with an attached Dean-Stark apparatus. A two phase system was formed. The mixture was refluxed until conversion was complete (about 11 hours) as determined by HPLC with detection at 212 nm. The reaction mixture was then cooled to room temperature and extracted twice with 200 mL of 0.5% aqueous sodium carbonate and once with 200 mL water. The benzene phase was dried with sodium sulfate and the solvent was removed under vacuum (20.6 g, 92% yield). HPLC was carried out using a Gemini C18 column (3 μm, 100 Å, 100 mm×4.6 mm) and isocratic elution with 40% B at 1 mL/min (A: 2 mM N-methylmorpholine and 1 mM acetic acid in water; B: 2 mM N-methylmorpholine and 1 mM acetic acid in ACN). $^1$H-NMR (300 MHz, CDCl$_3$) δ 7.34-7.19 (m, 5H), 4.34-4.26 (m, 1H), 4.14-4.08 (m, 1H), 3.89-3.76 (m, 2H), 3.7-3.6 (m, 1H), 2.81-2.72 (m, 2H), 2.08-1.95 (m, 3H), 1.45 (d, 3H).

Synthesis of Tosylated Dioxolane 40. 20 g (90 mmol) of dioxolane 39 and 100 mL dichloromethane were weighed into a 500 mL round bottom flask. 38 mL (273 mmol) triethylamine was added followed by 19 g (100 mmol) tosyl chloride. 50 mL more dichloromethane was used to wash-in tosyl chloride. The mixture was refluxed and analyzed by HPLC after 10 and 30 minutes. An additional 3.45 g (18 mmol) tosyl chloride was added and refluxing was continued for 15 more minutes when HPLC indicated complete conversion of 39 to 40. At this point, 5 g diethylethanolamine was added to quench excess tosyl chloride. The mixture was further refluxed for 30 minutes and then stirred at room temperature overnight. 150 mL toluene was added to the cooled reaction mixture and extracted twice with 600 mL 1M, pH 6 sodium dihydrogenphosphate buffer and once with 600 mL of 10% aqueous sodium chloride. The organic phase was evaporated under reduced pressure yielding a colorless oil with a 97% purity as determined by HPLC with 262 nm detection (33.0 g, 97% yield). HPLC was done using a Gemini C18 column (3 μm, 100 Å, 100 mm×4.6 mm) with a binary gradient of 40% to 75% B in 14 min at 1 mL/min (A: 2 mM N-methylmorpholine and 1 mM acetic acid in water; B: 2 mM N-methylmorpholine and 1 mM acetic acid in ACN). $^1$H-NMR (300 MHz, CDCl$_3$) δ 7.86-7.81 (m, 2H), 7.41-7.16 (m, 7H), 4.40-4.34 (m, 1H), 4.16-4.06 (m, 3H), 3.85-3.78 (m, 1H), 2.7-2.6 (m, 2H), 2.46 (d, 3H), 1.97-1.9 (m, 2H), 1.37 (d, 3H).

Synthesis of Tetra(ethylene glycol)-decorated Dioxolane 41. 8.5 g (213 mmol) sodium hydride (60% dispersion in oil) was digested in 160 mL of hexanes, allowed to settle and the hexanes were canulated out. A nitrogen blanket was applied over the reaction mixture to prevent moisture contamination. The hexanes rinse was repeated one more time. 100 mL of 1,4-dioxane was then added and to this, a mixture of 165 g (845 mmol) tetra(ethylene glycol) and 160 mL 1,4-dioxane was carefully added, dropwise, using a dropping funnel. Care was taken not to produce too much pressure during this addition. After this, a solution of 32 g (85 mmol) of tosylate 40 and 50 mL 1,4-dioxane was poured in. The mixture was then stirred in a 85° C. oil bath until conversion was complete (about 7 hours) as determined by HPLC and then was stirred overnight at room temperature. The solvent was removed under vacuum and the residue was partitioned between 1 L dichloromethane and 2 L of 5% aqueous sodium chloride. The organic phase was extracted two more times with the same volume of the aqueous sodium chloride. The workup was monitored with HPLC with and without labeling of the residual tetra(ethylene glycol). Tetra(ethylene glycol) labeling was done by first drying a 100 μL aliquot of the dichloromethane phase with sodium sulfate. Then, 20 μL of that solution was added to 5 μL of 5% 4-(dimethylamino) pyridine in DMF, 50 μL, DMF, 20 μL triethylamine and 10 μL benzoyl chloride. The mixture was vortexed, allowed to react for about 5 to 10 minutes and analyzed by HPLC with the UV detector set at 262 nm. The amount of unreacted tetra(ethylene glycol) left in the reaction mixture decreased below detection limit by the second extraction. The dichloromethane phase was then dried with sodium sulfate and the solvent was evaporated under reduced pressure (31.2 g, 92% yield). HPLC monitoring was the same as 40 above. $^1$H-NMR (300 MHz, CDCl$_3$) δ 7.33-7.20 (m, 5H), 4.42-4.30 (m, 1H), 4.14-4.11 (m, 1H), 3.83-3.57 (m, 18H), 2.92 (broad peak, 1H), 2.76-2.70 (m, 2H), 2.20 (s, 1H), 2.04-2.96 (m, 2H), 1.42 (d, 3H).

Synthesis of Diol-terminated Tetra(ethylene glycol) 42. Tetra(ethylene glycol)-decorated dioxolane 41 (30 g, 75 mmol) was added to a mixture of 300 mL of 2M aqueous HCl and 300 mL THF. Hydrolysis of the dioxolane ring was almost complete by 30 minutes at room temperature as shown by HPLC analysis. The reaction mixture was stirred for an additional 1.5 hours, after which sodium carbonate was carefully added until bubble formation ceased. Water and THF were removed under vacuum and the remaining residue was digested in 500 mL THF at room temperature overnight. The slurry was filtered and the filtrate was evaporated yielding an oil. This was then partitioned between 200 mL toluene and 200 mL water. The aqueous phase was extracted with dichloromethane after addition of 10 g sodium chloride. The aqueous solution was evaporated and the residue was digested in a mixture of 120 mL THF and 80 mL MTBE. The slurry was filtered and the solvent was removed under vacuum to afford a light tan viscous oil (17.3 g, 86% yield). Dioxolane hydrolysis was monitored by HPLC in the same manner as for 39; workup discussed for 40. $^1$H-NMR (300 MHz, CDCl$_3$) δ 4.14 (broad m, 1H), 4.03 (broad m, 1H), 3.88 (broad m, 1H), 3.7-3.5 (m, 19H, actual ~23H), 3.40 (broad m, 1H), 3.1 (m, 1H); $^{13}$C-NMR (300 MHz, CDCl$_3$) δ 72.9, 72.7, 70.9, 70.5, 70.43, 70.38, 70.34, 70.1, 63.8, 61.4 (two peaks are not resolved).

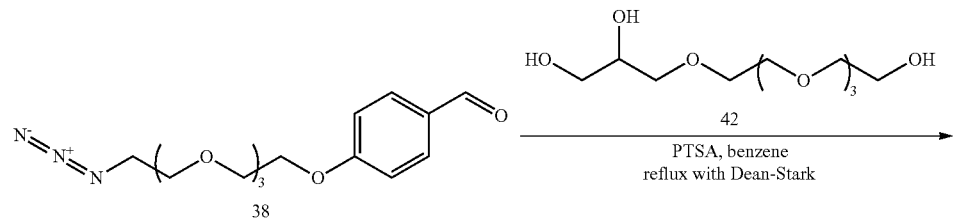

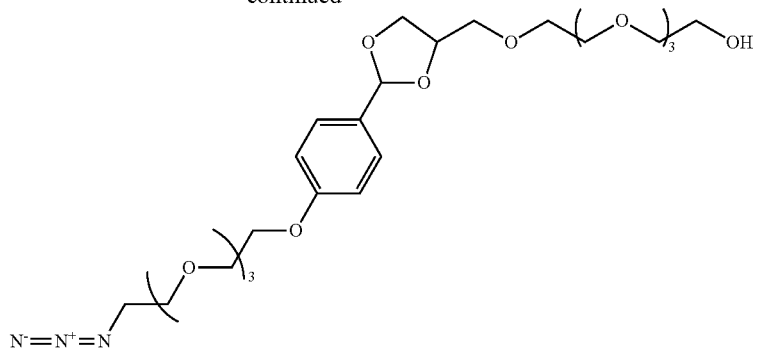

43

Synthesis of Cleavable Anchor Intermediate 43. A mixture of 17.2 g (64 mmol) of diol-terminated tetra(ethylene glycol) 42, 21 g (65 mmol) aldehyde 38, 122 mg (0.64 mmol) PTSA and 200 mL benzene was refluxed in a 500 mL round bottom flask with an attached Dean-Stark apparatus. Dioxolane formation was monitored by HPLC at 224 nm which showed that the reaction stopped progressing after about 24 hours of reflux. The benzene mixture was cooled to room temperature and mixed with 200 mL dichloromethane and 300 mL of an aqueous solution containing 30 g sodium chloride and 0.5 g sodium carbonate. The organic phase was dried with sodium sulfate and evaporated under vacuum to afford 30.4 g of oil with a purity of 64% (HPLC, detection at 224 nm). The oil was stored by adding about 0.1% v/v worth of triethylamine to scavenge any acid that may have contaminated the batch. A 5 g portion of this oil was purified by silica gel flash chromatography using 2 column volumes of ethyl acetate with 0.1% v/v triethylamine followed by 3 column volumes of a 1:1 mixture of acetone and ethyl acetate with 0.1% v/v triethylamine. The fractions containing target compound 43 were combined and evaporated to give a 95% pure colorless oil (6.78 g from 2×5 g portions, 56% yield after reaction and workup). Again, triethylamine was added to prevent hydrolysis of the dioxolane ring during storage.

Dioxolane formation was monitored by HPLC using a Gemini C18 column (3 μm, 100 Å, 100 mm×4.6 mm) with a binary gradient of 20% to 70% B in 15 min at 1 mL/min. The fractions from flash column chromatography were analyzed by HPLC using a Gemini C18 column (3 μm, 100 Å, 150 mm×4.6 mm) with a binary gradient of 20% to 80% B in 17 min at 1 mL/min (A: 2 mM N-methylmorpholine and 1 mM acetic acid in water; B: 2 mM N-methylmorpholine and 1 mM acetic acid in ACN).

Hydrolysis Rates of Different Dioxolanes. Hydrolysis rate of the dioxolane ring as a function of the ring substituents was studied. Four dioxolanes were prepared:

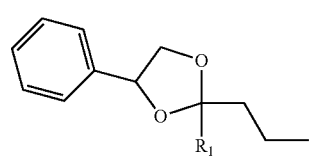

Set A

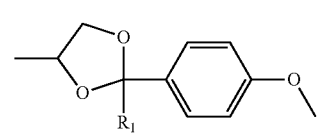

Set B $R_1$ = H or CH3

Two of the dioxolanes were formed from an aryl 1,2-diol with an alkyl ketone and an alkyl aldehyde as partner, respectively. The other two used dioxolanes derived from an alkyl 1,2-diol with an aryl ketone and an aryl aldehyde as partner, respectively. Hydrolyses rates of these dioxolanes at different pH values were monitored at room temperature and their half lives, $t_{1/2}$, were determined at the highest pH value where there was appreciable hydrolysis within an hour. A summary of the experiments is shown in Table 3. The dioxolanes derived from aryl diol/alkyl carbonyl have very slow hydrolysis rates, even at around pH 1. Based on Jaeger's report that $t_{1/2}$ of their alkyl diol/alkyl carbonyl-derived dioxolane was 56 min at pH 3, the aromatic substituent on the diol does not seem to increase hydrolysis rate. On the other hand, the alkyl diol/aryl carbonyl dioxolanes have relatively short half lives at pH 3.5 which suggests that an aromatic substituent, specifically, a p-alkoxyphenyl substituent on the carbonyl group increases the hydrolysis rate in general. These dioxolanes were also found to be stable at pH values 7 and above. Therefore, a dioxolane derived from a p-alkoxybenzaldehyde and an alkyl 1,2-diol was chosen as a cleavable element of the anchor group in SCaLER due to its favorable cleavage rate, although other dioxolanes may be employed. In addition, the chiral centers present in these compounds may offer variability in hydrolysis rates.

TABLE 3

Summary of the results of the dioxolane hydrolysis experiments.

| Diol | Carbonyl | Buffer solution | $t_{1/2}$ |
|---|---|---|---|
| styrene glycol | butyraldehyde | 1N HCl:THF (2:3) | —[a] |
| styrene glycol | methyl ethyl ketone | 1N HCl:THF (2:3) | 85 min |
| 1,2-propanediol | 4-methoxybenzaldehyde | pH 3.5 formic acid with LiOH, 20% ACN | 5 min |
| 1,2-propanediol | 4-methoxyacetophenone | pH 3.5 formic acid with LiOH, 20% ACN | 24 min |

[a] no detectable hydrolysis within 50 minutes

Synthesis of the Cleavable Anchor. The cleavable group is typically flanked by two spacers, one that connects it to the solid phase and another that connects it to the fluorophore. Spacers based on a well-defined oligo(ethylene glycol) (OEG) were elected in order to maintain good water solubility of the fluorophore and local hydrophilicity of the cleavable anchor. Tetra(ethylene glycol) was chosen as the oligo(ethylene glycol) since it is readily available in high purity. The cleavable anchor was planned to build in a convergent manner where dioxolane formation comes last. Therefore, synthesis of the cleavable anchor was divided into two parts: the first the preparation of the benzaldehyde side, the second the preparation of the alkyl diol side. The benzaldehyde side of the cleavable anchor was prepared as shown below.

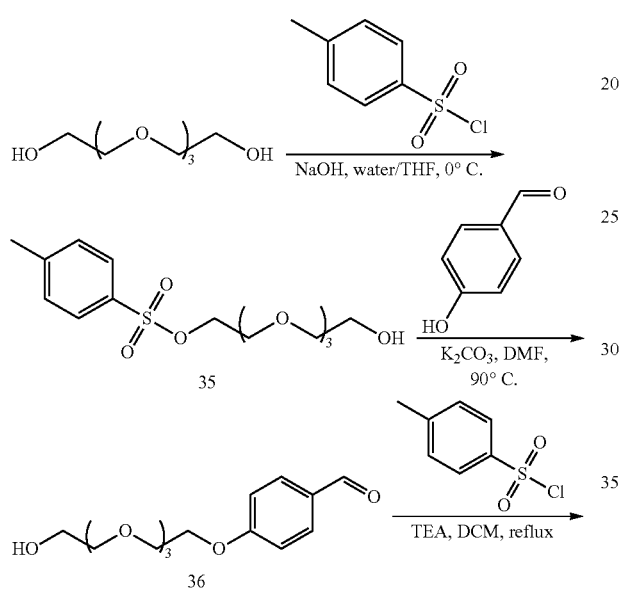

-continued

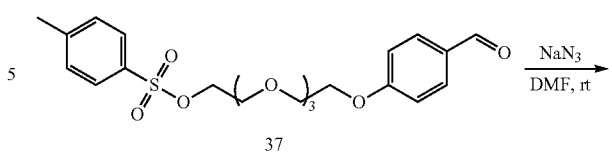

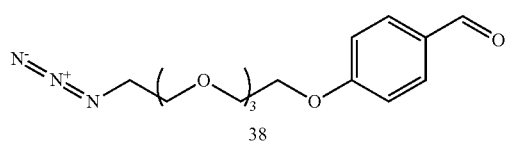

The synthesis started with monotosylation of tetra(ethylene glycol) where monotosylate 35 was obtained in 90% yield (based on tosyl chloride) with a purity of 96%. The procedure used a large excess of tetra(ethylene glycol) to minimize bis-tosylation. This step was improved later, where a similar degree of monotosylation was achieved, at comparable purity, with only 1.2 equivalents of tetra(ethylene glycol) using $Ca(OH)_2$ as base instead of silver oxide suggested in the literature (Bouzide, A., Sauve, G., *Organic Letters* 2002, 4, 2329-2332). Monotosylate 35 was then coupled with 4-hydroxybenzaldehyde to form compound 36 which was subsequently activated with tosyl chloride to allow azido substitution and production of compound 38. The azido group was to be easily converted later on to an active group (i.e., amino group) for attachment to the solid phase.

The alkyl diol part was synthesized according to the scheme depicted below.

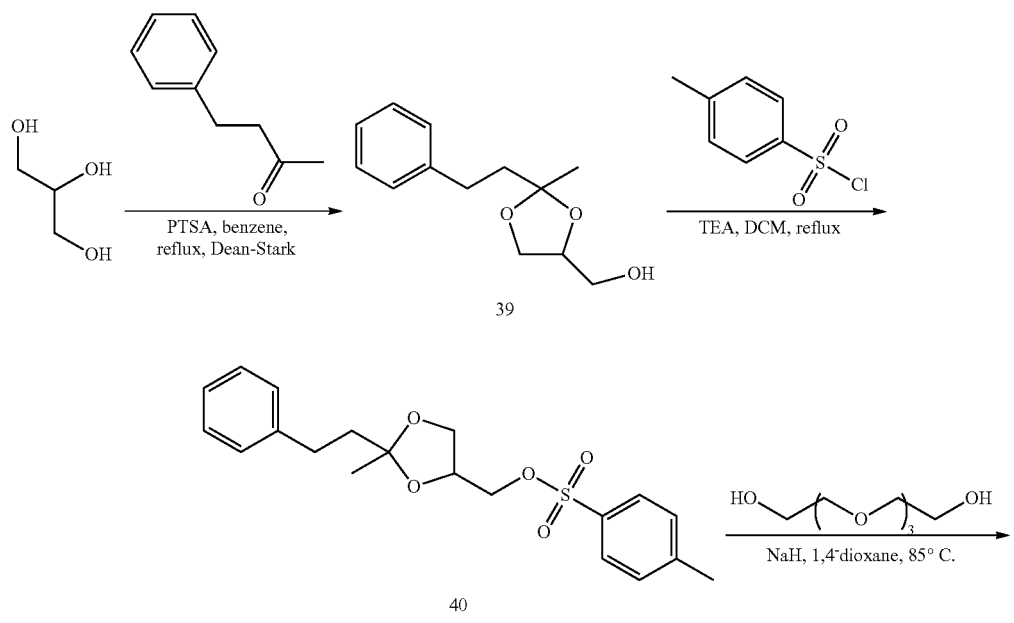

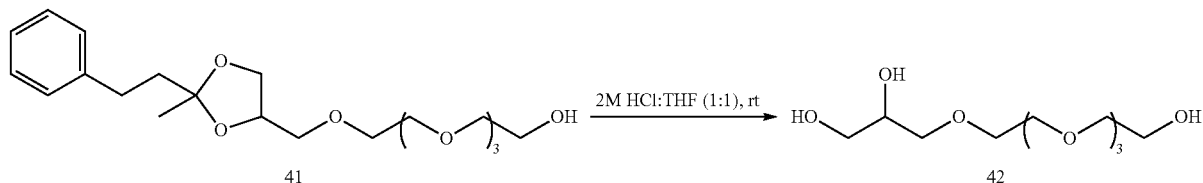

Glycerol was used as the starting material where the 1,2-diol part was protected as a 1,3-dioxolane ring using benzyl acetone to make compound 39. Benzyl acetone was specifically chosen for two reasons. First, the presence of an aromatic ring simplified HPLC analysis. Second, the carbonyl group separated from the aromatic ring by a short alkyl chain was expected to mimic the behavior of acetone which selectively forms the dioxolane ring with the 1,2-diol, not the 1,3-diol. The hydroxyl group of compound 39 was then activated with tosyl chloride, followed by coupling with tetra(ethylene glycol). Disappearance of the latter was analyzed by HPLC using UV detection by first derivatizing the glycol with benzoyl chloride. Tetra(ethylene glycol)-decorated dioxolane 41 was then subjected to acidic conditions to free the diol and form 1,2-diol-terminated tetra(ethylene glycol) 42.

The aldehyde and the diol sides of the cleavable anchor were then put together as shown below using conventional methods to form cleavable anchor intermediate 43.

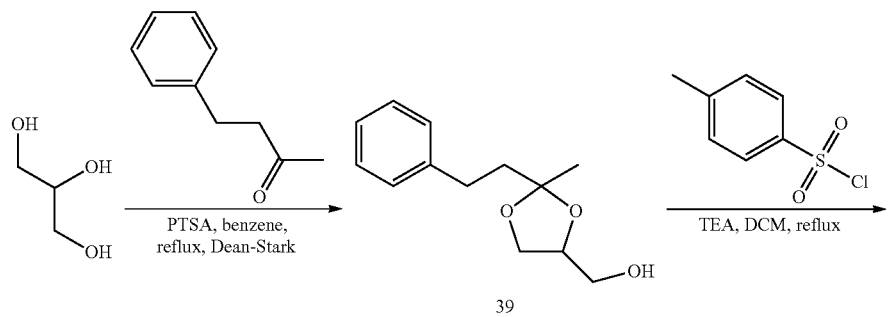

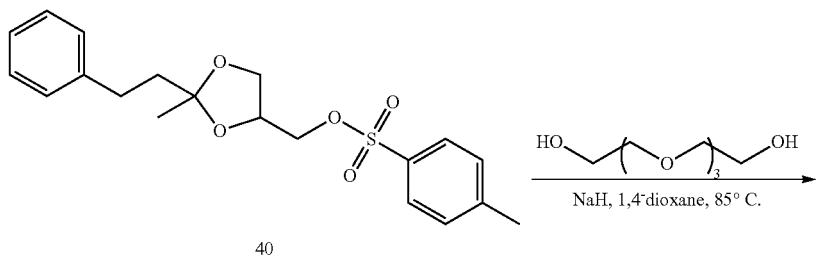

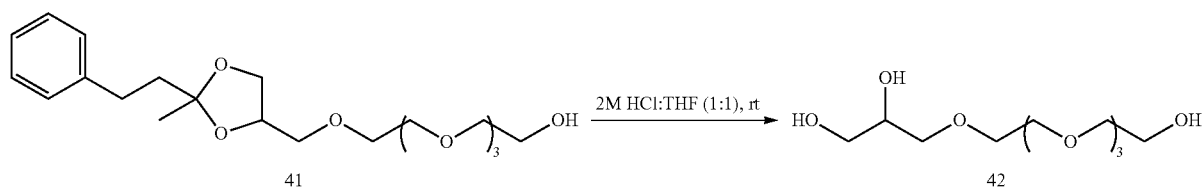

One end of 43 had an azido group which could be later converted to —NH$_2$ for connection to the solid phase. The other end had a hydroxyl group which was to be used to couple with the fluorophore. The reasons for the choice of hydroxyl as the terminating group for 43 are discussed in the next section.

The resulting red/brown residue was mixed with 1 mL water, centrifuged and the target compound was recovered from the supernatant by semi-prep HPLC using a Luna 5 μm HILIC column (250 mm×10 mm I.D.) with a HILIC guard cartridge in a Beckman HPLC system equipped with a 508 autosampler, 126 pump and 168 photodiode array detector.

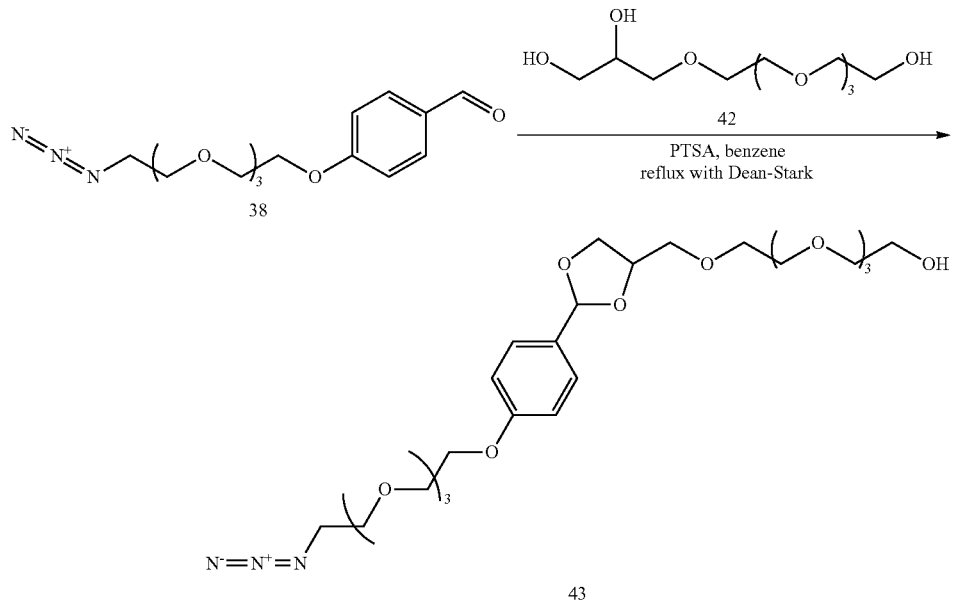

Example 7: Attachment of a Cleavable Anchor to a Fluorophore

Materials and Methods. 1,3-propanedithiol, dimethylsulfoxide (DMSO), trifluoroacetic acid (TFAA) and sodium trifluoroacetate (NaTFA) were purchased from Sigma Aldrich. Sodium hydroxide, pyridine and triethylamine (TEA) were supplied by EMD. 40 μm silica gel for preparative LC was acquired from J. T. Baker Chemical Co. HPLC analyses and semi-preparative HILIC separations were done in a Beckman HPLC system equipped with a 508 autosampler, 126 pump and 168 photodiode array detector.

Synthesis of Fluorophore 44. 50 mg (4 μmol) of fluorophore 33 was dissolved in 700 μL DMSO and added to a mixture of 700 mg (1.2 mmol) cleavable anchor intermediate 43 and 250 μL of a 50% aqueous solution of sodium hydroxide. After addition, the reaction mixture turned dark blue/violet. The reaction mixture was placed into 55-60° C. oil bath. The reaction was monitored by HILIC and was found to be complete in about 20 hours. After cooling to room temperature, a mixture of 757 μL TEA and 377 μL TFA was added to neutralize sodium hydroxide and buffer the system. The color of the reaction mixture turned dull orange. A 15 mL portion of MTBE containing a few drops of TEA was then used to precipitate out the target compound. The heterogeneous mixture was vortexed, centrifuged and the supernatant was decanted. The bottom phase was a viscous liquid containing the target, sodium trifluoroacetate, triethylammonium trifluoroacetate, water and DMSO. 15 mL of MTBE was used to digest the bottom phase twice in order to remove most of DMSO and triethylammonium trifluoroacetate without solubilizing the target. After MTBE, the residue was digested twice with the more polar solvent mixture consisting of 5 mL THF and 10 mL MTBE.

The flow rate was 5 mL/min. After sample injection, there was a 4 min long isocratic elution segment at 98% B that was followed by a step change to 85% B. The eluent composition was maintained at this concentration until the desired component was eluted, followed by a 5-minute cleaning of the column at 50% B. The material that eluted during this wash step was collected and analyzed to confirm that it was free of the target compound. The presence of the target in this fraction would have indicated a severely tailing peak resulting from precipitation of the component during in-line Taylor dilution-mediated injection (described herein). The solvent composition was then changed back to 98% B (A: 20 mM sodium trifluoroacetate in water; B: 20 mM sodium trifluoroacetate in ACN). Solvents were filtered through a 0.65 μm PVDF membrane filter from Millipore.

The fractions containing the target were combined and the solvent was removed under vacuum. To remove NaTFA, the residue was eluted through a 1 cm I.D.×14 cm column packed with 40 μm silica in HILIC mode using a buffer consisting of 10 mM TEA and 5 mM TFA. A step gradient elution was used starting at 100% ACN (sample loading), followed by an elution at 5% water/ACN composition, then at 10% and lastly at 15% water/ACN. Each step used 5 column volumes. The target fractions were then evaporated and the residue was dissolved in the least amount of ACN and precipitated out with 2 mL MTBE that contained a few drops of TEA. The dissolution—precipitation process was repeated five times to remove triethylammonium trifluoroacetate from the target. The solid was dried under vacuum (42 mg, 57% yield).

Note: After drying, the solids were stored without addition of triethylamine. After 1 day, HILIC analysis showed hydrolysis of 10% of the cleavable anchor. Addition of a few drops of triethylamine prevented this hydrolysis even after days of storage at room temperature.

HILIC analysis was done using a Luna HILIC column (3 μm, 200 Å, 150 mm×4.6 mm) with a binary gradient of 95% to 75% B in 20 min at 1 mL/min (A: 10 mM 3-morpholino-propane-1-sulfonic acid (MOPS) and 5 mM NaOH in water; B: 10 mM MOPS and 5 mM NaOH in 5% water in ACN).

Synthesis of Fluorophore 45. The reduction of azido fluorophore 44 to the amine was accomplished by mixing 42 mg of 44 with 600 μL water, 420 μL triethylamine, 2 mL pyridine and 302 μL 1,3-propanedithiol. The reaction was complete after about 2 hours as determined by HPLC. The reaction mixture was concentrated by adding 30 mL MTBE to take in most of the solvent and reagent without solubilizing the product. After centrifuging, the phases were separated. The bottom phase was a red/brown viscous liquid while the top phase was colorless. 20 mL MTBE with a few drops of TEA was again added, the mixture vortexed, centrifuged and the phases separated. The digestion step was repeated with a more polar solvent mixture consisting of 10 mL THF and 20 mL MTBE, followed by digestion with a still more polar solvent, 20 mL THF. The solvent in each step contained a few drops of triethylamine. The residue was dissolved in 200 μL DMF that contained some triethylamine and precipitated out with 20 mL THF. The solid was dissolved in 400 mL DMSO to give an approximate amine-terminated fluorophore 45 (as triethylammonium salt) concentration of 90 mg/mL. The material had the 10% "hydrolyzed" fluorophore contaminant as noted above for 44 and was stored in the freezer.

Rationale for the Direct Attachment of the Cleavable Anchor to the Fluorophore. During the development of fluorophore 33 the stability of the trisulfonamide derivative of APTS was tested when subjected to various, relatively harsh conditions. One of the tests conducted was digestion of trisulfonamide 22 with sodium hydroxide in water and methanol at an elevated temperature.

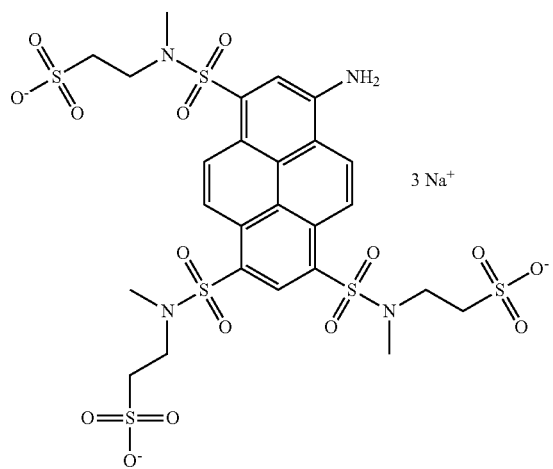

22

Figure 21:
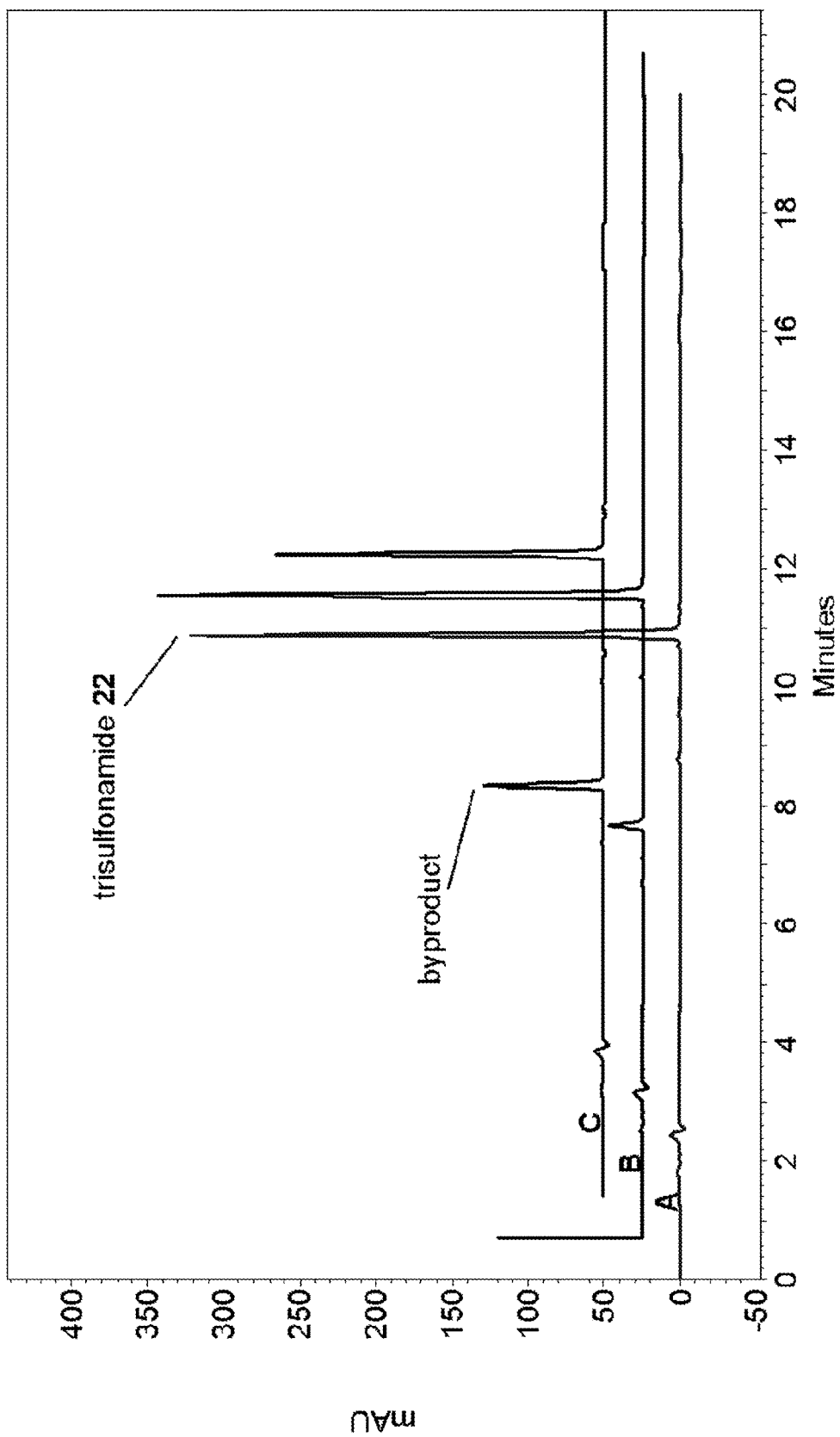
FIG. 21: HILIC analysis of the reaction mixture after treatment of trisulfonamide 22 with sodium hydroxide in a mixture of water and methanol at 65° C. for t=0 h (A), 0.5 h (B) and 2.2 h (C).
Figure 22:
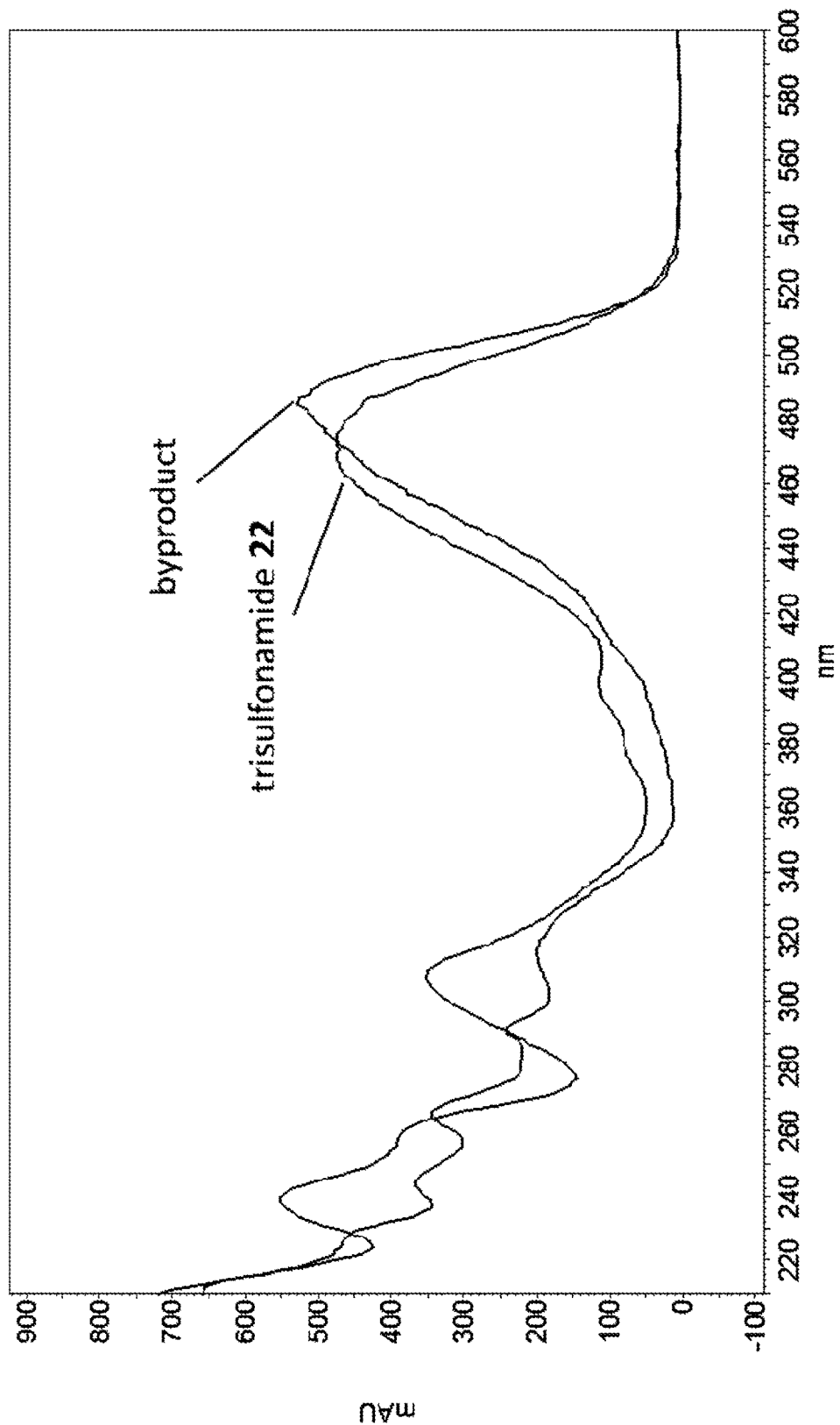
FIG. 22: Overlay of the UV absorbance spectra of trisulfonamide 22 and the unknown byproduct.
Figure 23:
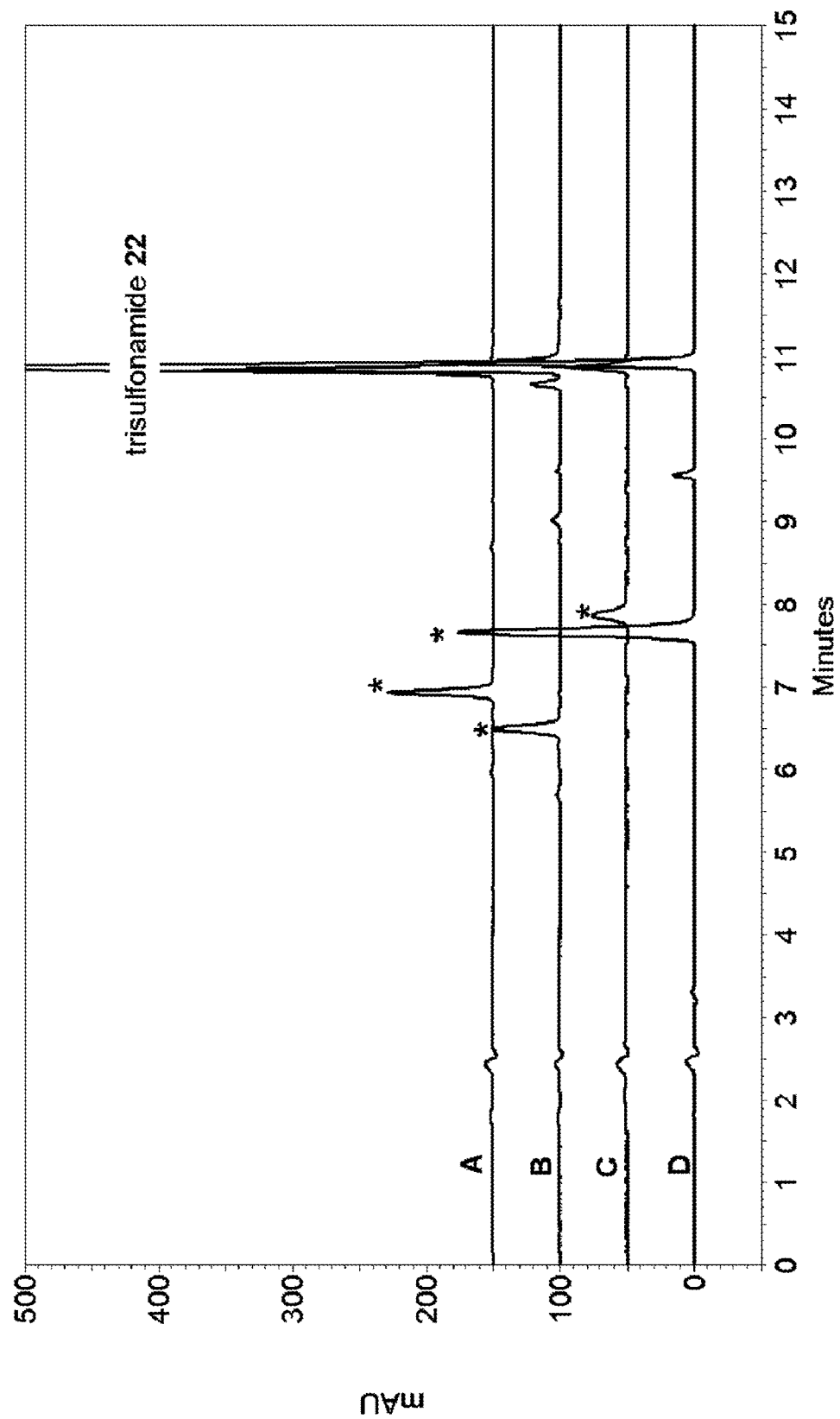
FIG. 23: Treatment of trisulfonamide 22 with different alcohols under basic conditions. The alcohols used were methanol (A), ethanol (B), tetra(ethylene glycol) (C) and glycerol (D).

Byproduct formation was observed by HPLC in half an hour as shown in FIG. 21. The UV absorbance spectrum of the byproduct was significantly different from that of trisulfonamide 22 (FIG. 22). There was a bathochromic shift of about 15 nm and the broad peak profiles in the UV range gave way to narrower, more defined ones. Both of these observations pointed to a change in the aromatic core of the fluorophore. MS analysis of the byproduct showed that it had a [M·H]⁻ value of 648.12 corresponding to the putative structure presented above where one of the sulfonamide groups was replaced by a methoxy group. To test if the transformation was exclusive to methanol, different alcohols were tested under the same basic conditions. Each alcohol gave its own byproduct peak in HILIC as shown in FIG. 23. However, all byproducts had the same UV absorbance spectra. This suggested that their core fluorophore structures were also the same and only the alkoxy substituent was different which would account for the differences in their retention times in HILIC. See the structure below in this regard. It was subsequently determined that the exchange of the sulfonate group to the alkoxy group did not take place with APTS as the fluorophore substrate.

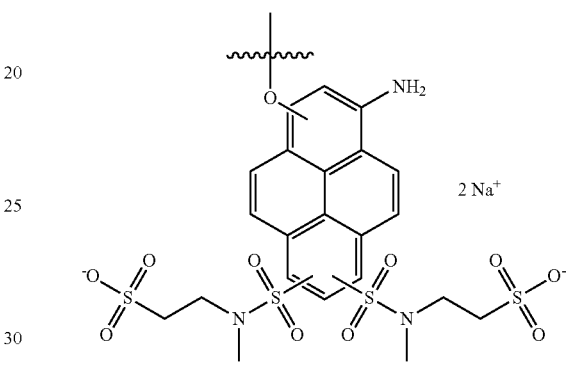

Figure 24:
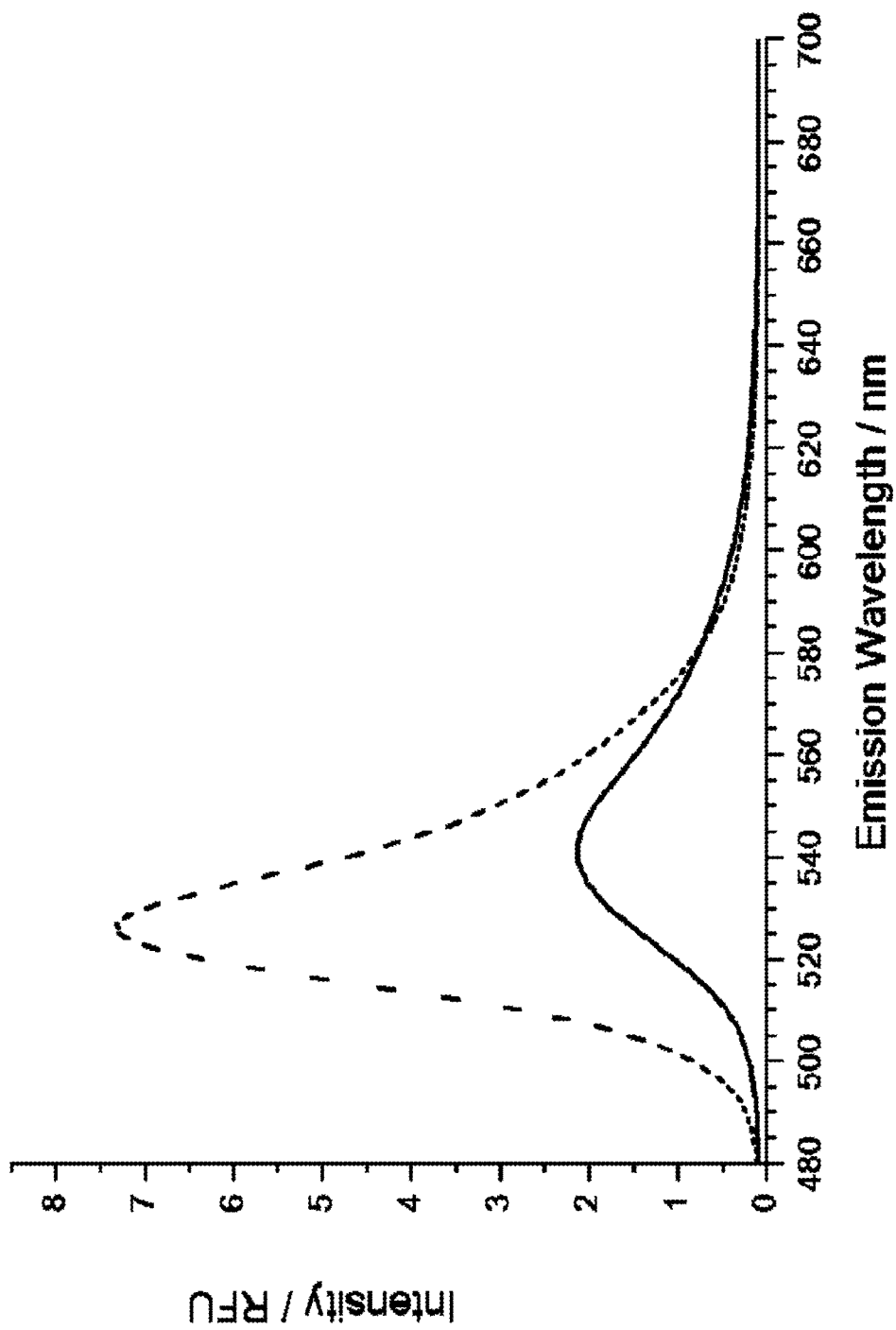
FIG. 24: Fluorescence emission spectra of trisulfonamide 22 (solid line) and the byproduct obtained in basic ethanol (dashed line). Both samples have the same molar absorbance at 480 nm.
Figure 25:
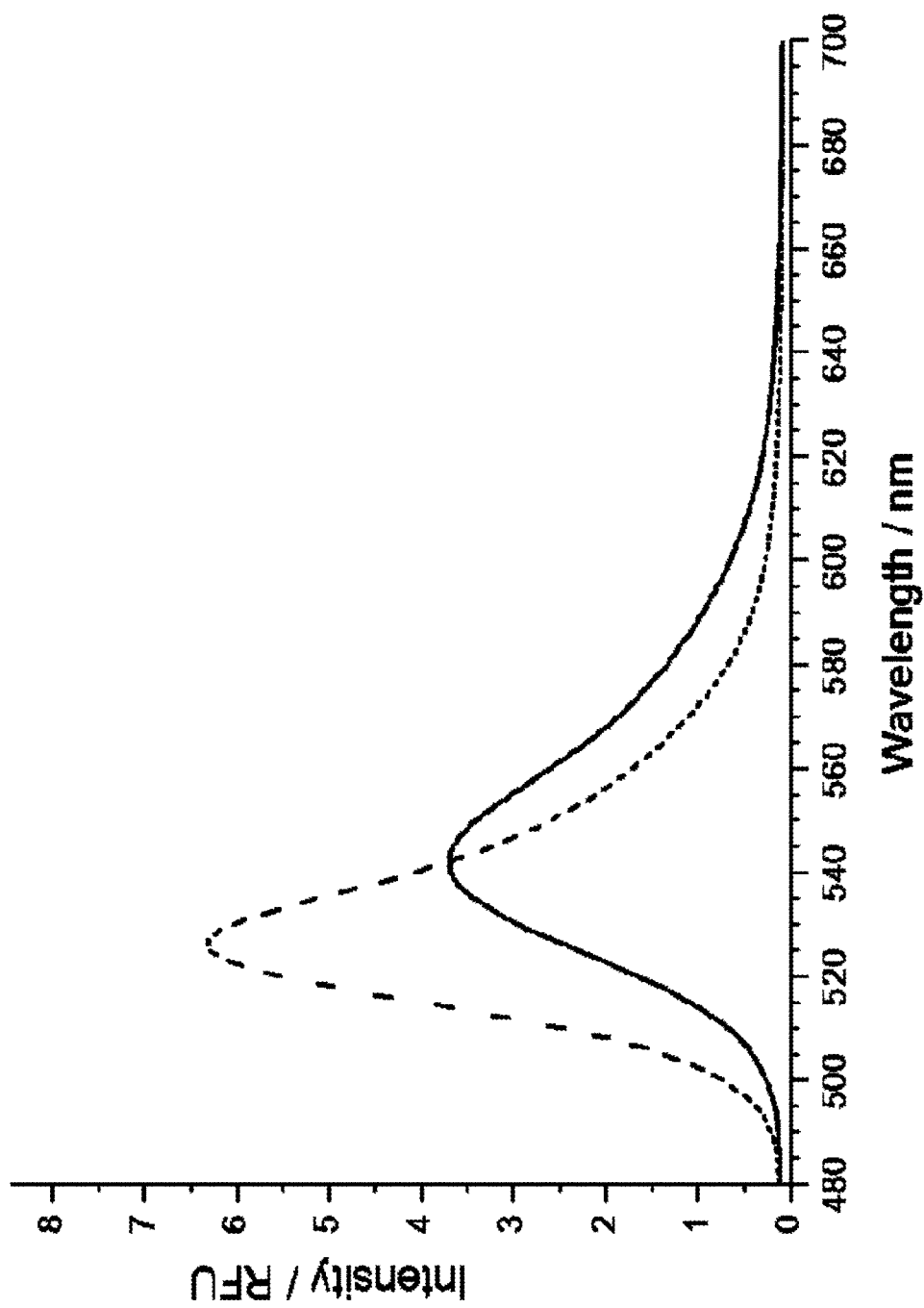
FIG. 25: Fluorescence emission spectra of trisulfonamide 22 (solid line) and the byproduct obtained in basic glycerol (dashed line). Both samples have the same molar absorbance at 480 nm.

To have a qualitative idea of how fluorescence changed due to the alkoxy substitution, the fluorescence spectra of an ethoxy and a glycerol derivative were taken and compared with that of trisulfonamide 22 (FIG. 24 and FIG. 25, respectively). The samples in each pair of measurements had the same UV absorbance at 480 nm. The higher fluorescence intensities of the alkoxy derivatives suggested that there was an increase of the fluorescence quantum yield due to the alkoxy substitution. The figures also show a hypsochromic shift of the $\lambda_{max}^{em}$ of the alkoxy derivatives to 525 from the 540 nm value of trisulfonamide 22. These observations prompted exploitation of the sulfonamide to alkoxy group exchange for the attachment of the cleavable anchor to the APTS core. Also, this decision suggested the synthesis of a cleavable anchor with a terminal primary hydroxyl group for connection to the fluorophore, although this synthetic route is not limiting to achieve the desired fluorophore-cleavable anchor connectivity.

Figure 26:
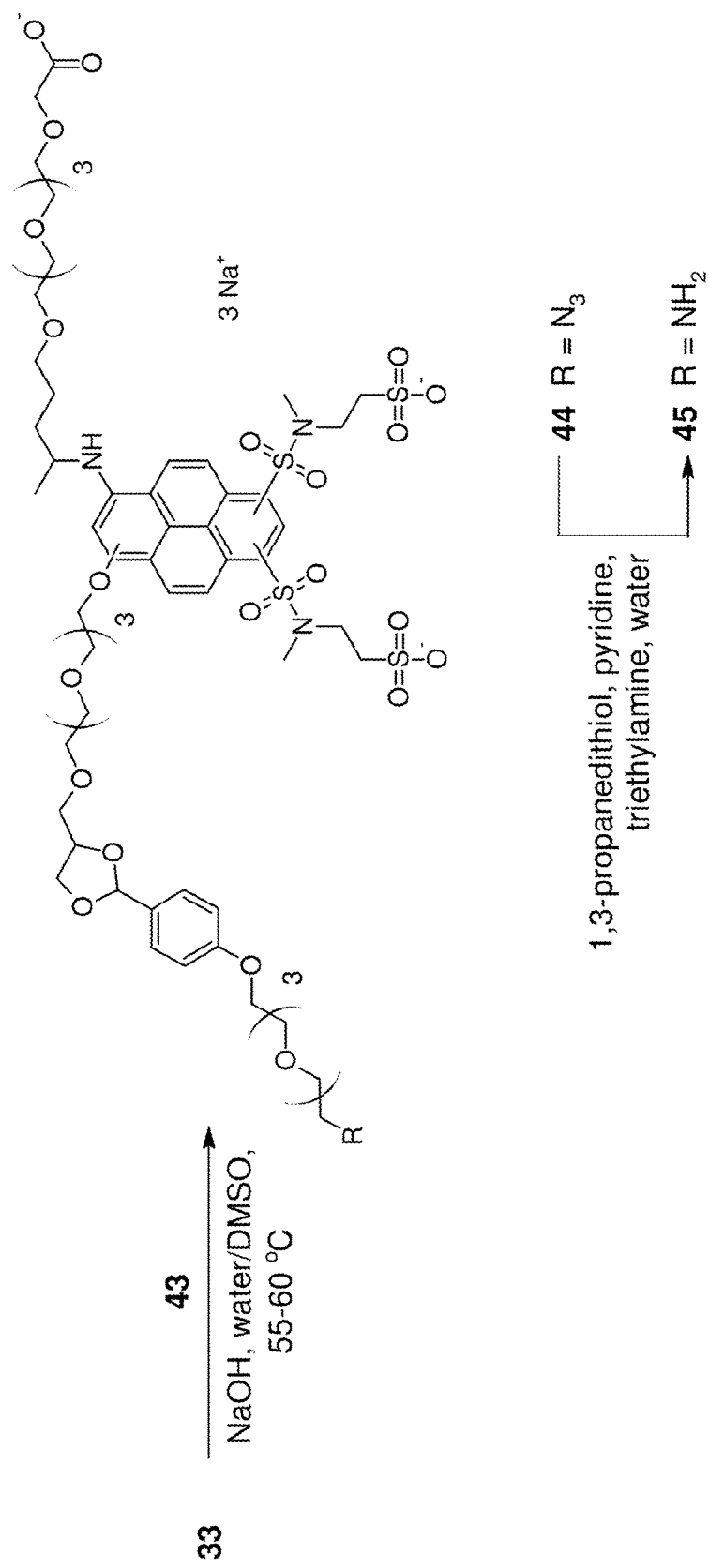
FIG. 26: Scheme for the attachment of hydroxyl-terminated cleavable anchor intermediate 43 to fluorophore 33 and the subsequent reduction of the azido group to the amino group.
Figure 27:
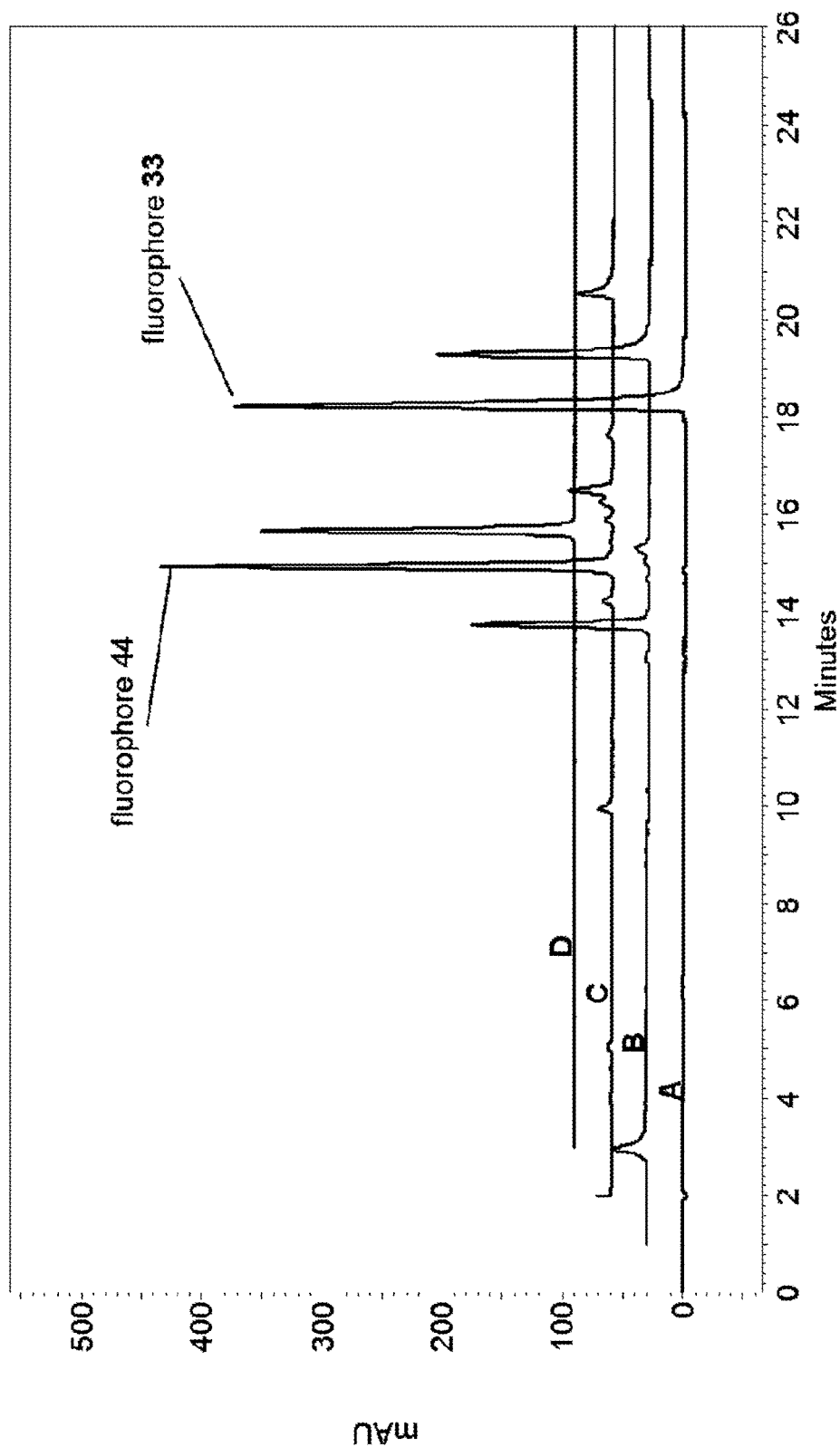
FIG. 27: HPLC monitoring of the attachment of cleavable anchor intermediate 43 to fluorophore 33 showing the chromatograms for the starting material (A), the reaction mixture after 13 hours (B), the reaction mixture after 30 hours (C) and the target after semi-prep HILIC purification (D).

Hydroxyl-terminated cleavable anchor intermediate 43 was connected to fluorophore 33 by reacting the two in the presence of a high concentration of sodium hydroxide in water and DMSO at 50-60° C. (see FIG. 26). HPLC monitoring as shown in FIG. 27 indicated that the reaction was complete after 30 hours. The reaction mixture was purified by semi-preparative HILIC yielding fluorophore 44 with a purity of 99.5%. The azido group on the other end of the cleavable anchor was then reduced to an amino group using very mild, slightly basic conditions to produce fluorophore 45.

Prior to immobilization onto the solid phase, the fluorophore in its final form was subjected to hydrolysis experiments under acidic conditions in pH 3.1, 3.5 and 4.2 solutions. These pH values were chosen because proteins were expected to tolerate them for short periods of time (thus the need for high cleavage rates). It was important to do the cleavage test at this point and not earlier in order to account for any effects the fluorophore might have on the cleavable anchor. The test solutions were analyzed using CE-LIF with a pH 10 background electrolyte to ensure that there was no further cleavage either in the CE sample or in the separation capillary during electrophoresis. An internal standard, 8-hydroxypyrene-1,3,6-trisulfonic acid, trisodium salt, was used to compensate for any variation in sample injections.

then used to calculate the $t_{0.5}$ values of the cleavable group for each pH. The time at which only 1% of the cleavable group population was left intact, $t_{0.01}$ was also determined. These values represent the required residence times of the cleaving agent (i.e., acidic buffer) in the SPR to recover 99% of the label and the labeled analytes. A summary of the $t_{0.5}$ and $t_{0.01}$ values is shown in Table 4.

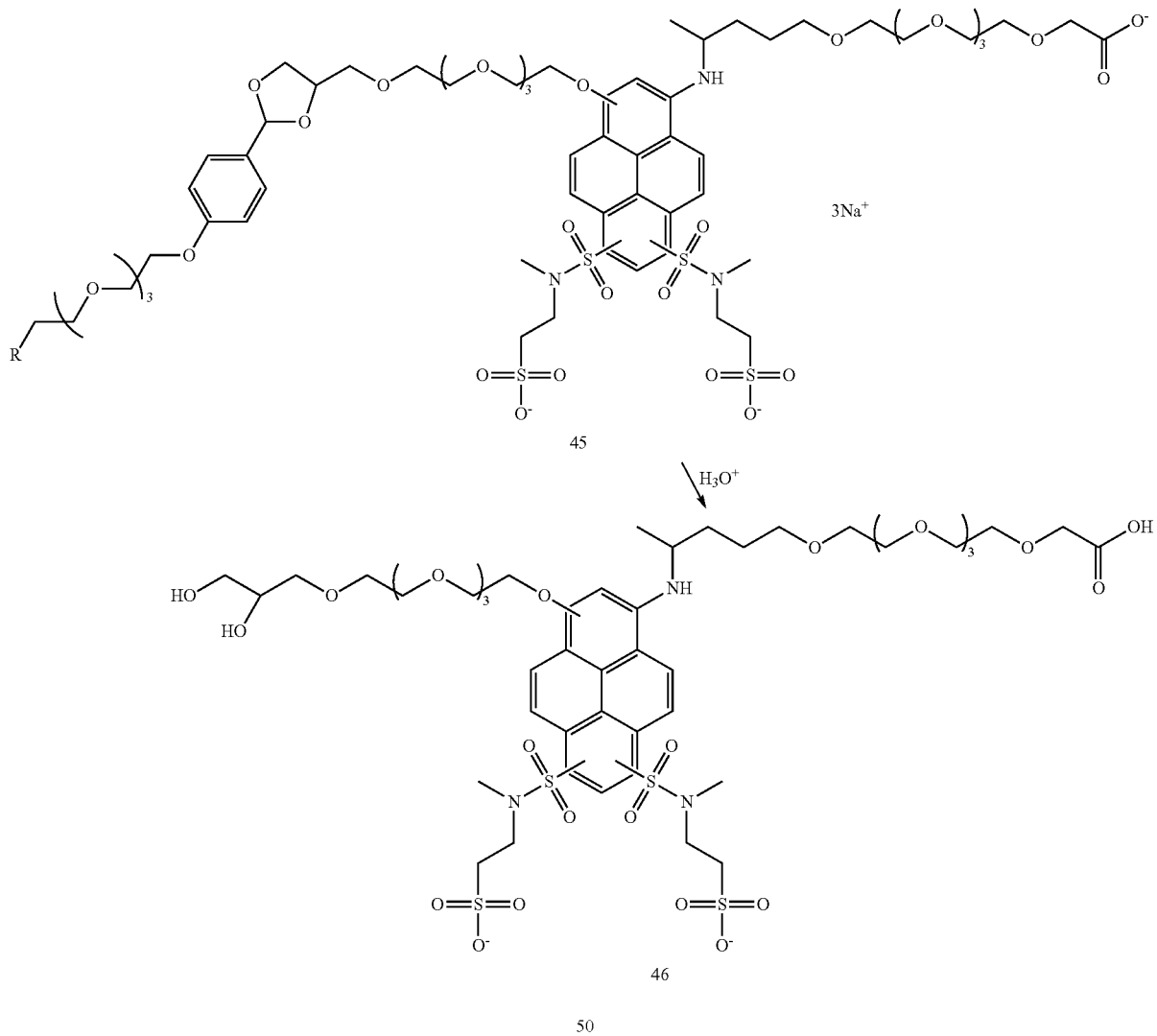

Aliquots were taken from the three hydrolysis mixtures at different times, analyzed by CE and the normalized peak areas corresponding to intact 45 were plotted as a function of hydrolysis time in order to determine the hydrolysis rate constants. Assuming that cleavage followed a pseudo-first order rate kinetics, the following equation was fitted to the measured data:

$$\frac{A}{A_0} = e^{-k't} \quad (4.1)$$

where A and $A_0$ are the normalized peak areas at time t and t=0, k' is the pseudo-first order rate constant (s$^{-1}$) and t is hydrolysis time in seconds. The respective k' values were

TABLE 4

Summary of the $t_{0.5}$ and $t_{0.01}$ values for the hydrolysis of the cleavable group of fluorophore 45 at different pH.

| pH | $t_{0.5}$/min | $t_{0.01}$/min |
|---|---|---|
| 3.1 | 1.0 | 6.5 |
| 3.5 | 2.3 | 15.4 |
| 4.1 | 9.0 | 59.8 |

Ideally, the k' values for cleavage of the cleavable group should be proportional to the hydronium ion concentration, [$H_3O^+$]. A nonlinear relationship would mean that cleavage depended on other unknown factors as well which would have to be determined. Plotting the k' values against [$H_3O^+$] indicates that the relationship is indeed linear. The slope of the fitted line is the second order rate constant of the cleavage, k. Using this equation, one can also predict the $t_{0.5}$ and $t_{0.01}$ values at any pH value.

Fluorescence Properties of Fluorophore 46. The relative fluorescence quantum yield was determined to confirm the initial finding, i.e., that fluorescence improved upon replacement of one of the sulfonamide groups with an alkoxy group in fluorophore 46. With Rhodamine 6G as standard, the relative quantum yield was determined to be 0.86, which is about 15% higher than that of the trisulfonamido APTS, fluorophore 33.

Figure 28:
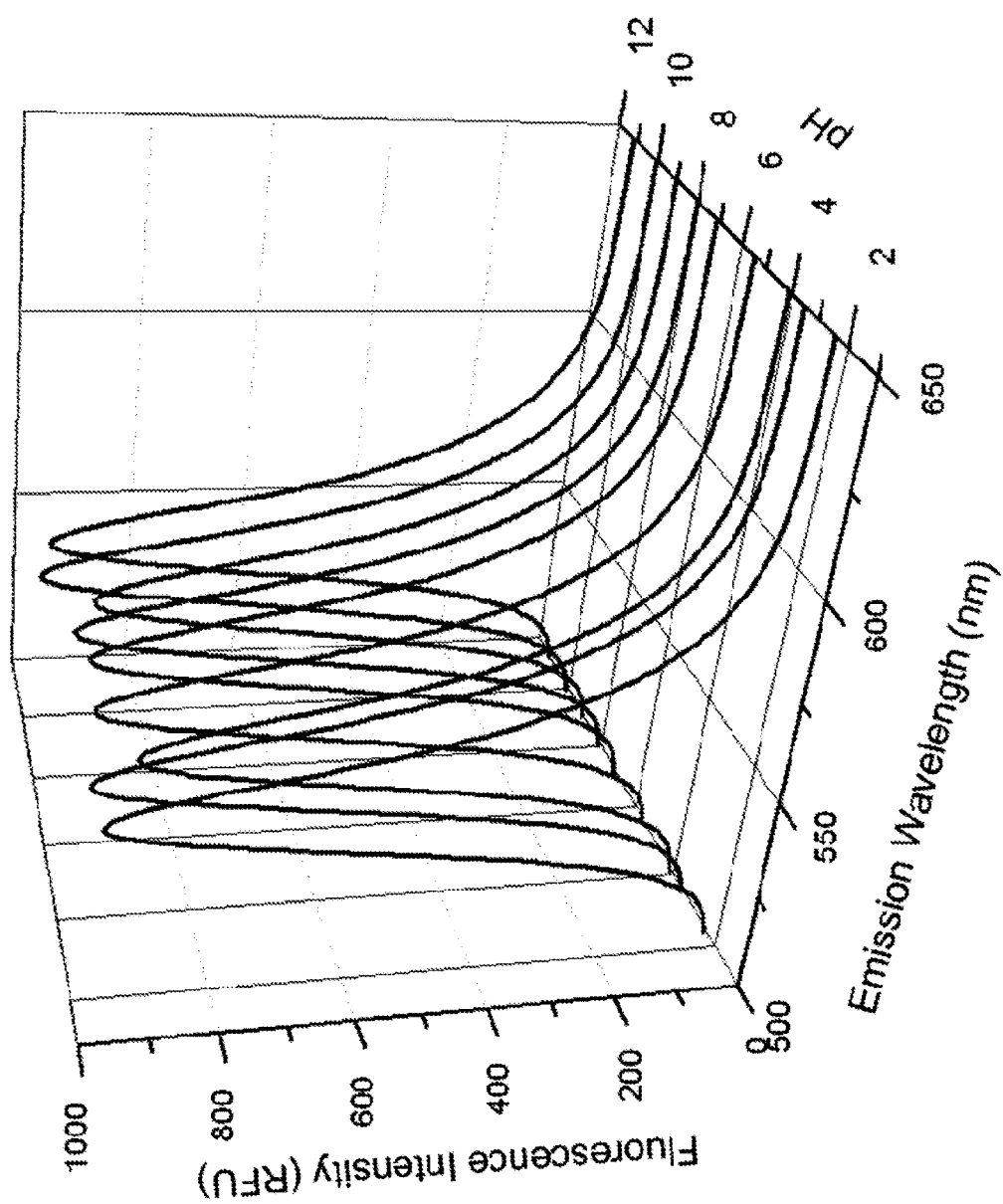
FIG. 28: Fluorescence spectra of fluorophore 46 recorded at different pH values.

The fluorescence spectra at different pH values were also recorded to see if the fluorophore, after the derivatization, still had pH-independent fluorescence properties. FIG. 28 shows that the fluorescence of fluorophore 46 is practically independent of pH in the range of importance for CE. Though there were slight (about 7%) variations in the intensities, they were not correlated with pH and could have been caused by matrix effects (buffer constituents). The $\lambda_{max}^{em}$ was also constant throughout the pH range.

Example 8: Synthesis of a Solid Phase and Immobilization of a Fluorophore Through a Cleavable Anchor Materials and Methods. 2-Hydroxyethylmethacrylate (HEMA), ethylene glycol dimethacrylate (EDMA), 2-methoxyethyl acrylate (MEA), azobisisobutyronitrile (AIBN), 1-octanol, ethanolamine, 2-methoxyethylamine, 3-(trimethoxysilyl)propyl methacrylate (BindSilane), anhydrous dimethylsulfoxide and anhydrous acetonitrile were purchased from Sigma Aldrich. N,N'-Disuccinimidyl carbonate (DSC) was obtained from Chem-Impex International Inc. HPLC columns were acquired from Phenomenex. Capillary melting point tubes, borosilicate glass (0.8-1.1 mm I.D.×100 mm) were purchased from VWR. HPLC analyses were done in a Beckman HPLC system equipped with a 508 autosampler, 126 pump and 168 photodiode detector. UV photoinitiation of the monolith monomers was done in a closed UV box equipped with four UV strip lights designed to emit at 360 nm (Southern New England Ultraviolet Company).

Bifunctionalization of the Capillary Melting Point (MP) Tubes. A modification of the bifunctionalization procedure described by Hjerten and coworkers (Li, Y. M., Liao, J. L., Nakazato, K., Mohammad, J., et al., *Analytical Biochemistry* 1994, 223, 153-158) was used. 20 MP tubes were fully immersed in HPLC-grade acetone in a 50 mL centrifuge tube and sonicated for 10 minutes. Acetone was then removed, the tubes were rinsed with water, fully immersed in 0.1M NaOH, sonicated for 30 minutes and allowed to stand for another 2 hours. The NaOH solution was removed, the tubes were rinsed with water, then immersed in 0.1M HCl and sonicated for 30 minutes. The HCl solution was removed, the tubes were rinsed with water and acetone, then immersed in acetone and sonicated for 10 minutes. The tubes were stored in acetone. Between five to ten MP tubes were transferred to a 15-mL centrifuge tube, immersed in a 20% solution of BindSilane in acetone, sonicated for 10 minutes, then allowed to stand overnight. The tubes were washed with HPLC-grade acetone and used in monolith synthesis.

HEMA-based Monolith Synthesis in Melting Point Capillaries. The monomer mixture was prepared by combining 12 mg AIBN, 0.48 g EDMA, 0.195 g HEMA, 0.455 g MEA and 1.8 g 1-octanol. The mixture was sonicated for about a minute to dissolve AIBN and was deaerated by sparging with nitrogen through a needle for about 15 minutes.

While the monomer mixture was deaerated, a bifunctionalized MP tube was flushed with nitrogen to evaporate acetone. Both ends of the melting point tube were then sealed with rubber septa and very carefully flushed with nitrogen using 22-gauge needles as inlet and outlet at the ends of the tube.

Once the monomer solution was ready, a ~0.3 mL aliquot was taken out using a 1-mL syringe. The melting point tube was detached from the nitrogen source and with the needles still pierced through the septa, was very carefully filled with the monomer solution through one of the needles. Care was taken to remove any bubble from the tube. Once filled, the needles were removed and the sealed MP tube was suspended in a UV box for photoinitiation and curing. The monolith mixture became opaque after only about 10 minutes under the UV light. A stream of air was maintained in the box to keep the temperature from increasing due the warmth of the lamps. After overnight curing in the UV box, about 1.5 cm was cut off from each end of the MP tube. The MP tube was connected to an HPLC pump using a union for 1/16 in O.D. tubings. ACN was pumped through the monolithic column at a flow rate of 0.01 mL/min for 5 minutes and then at 0.05 mL/min for about 30 minutes. Pressure was monitored to be sure that the monolith was not plugged. Pressure was initially high when 1-octanol was still present in the column but decreased to a limiting value later on. After the ACN flush, the monolith was stored in a closed tube with several drops of ACN to prevent its drying.

Activation of the Monolith Surface. The monolithic column, housed in a MP tube, was connected to a syringe pump using a 1/16 in zero dead volume (ZDV) union. The monolith was rinsed with 0.5 mL of anhydrous ACN at a flow rate of 10 µL/min. A solution of the activating agent was prepared by mixing 25 mg DSC and 1.25 mL anhydrous ACN. This was sonicated and filtered through a 0.45 µm PVDF syringe filter. 13 µL TEA was added to 1.2 mL of the filtrate. 0.8 mL of this solution was pumped through the monolith at 10 µL/min, followed by 0.8 mL of anhydrous ACN at 10 µL/min to remove unreacted DSC. The hydroxyl groups on the monolith surface now became activated as N-hydroxysuccinimidyl carbonate (NHS-carbonate) groups.

Immobilization of Fluorophore 45 on the Activated Monolith Surface. A solution of fluorophore 45 in anhydrous DMSO (90 mg fluorophore 45 in 100 µL DMSO) was mixed with 100 µL anhydrous DMSO, 250 µL anhydrous ACN and 1 µL TEA. This solution was pumped through the activated monolith (length was 75.4 mm) at a flow rate of 2 µL/min. While the fluorophore solution was pumped in, the effluent from the monolith (spent fluorophore solution) was collected into 20-µL fractions which were later analyzed by HPLC to determine the breakthrough volume. As mentioned above, the DMSO solution of fluorophore 45 contained 10% diol-terminated fluorophore 46 (lacking the primary amino group-terminated cleavable anchor) as contaminant, which was conveniently used as an internal standard for breakthrough analysis. Yellow green unretained 46 visibly progressed through the monolith while bound fluorophore 45 turned the monolith orange colored. Once the orange colored front reached the end of the monolith, about 80 µL more of the fluorophore mix was pumped through it to ascertain complete loading, after which the monolith was washed with a 200 µL portion of a pH 9, 0.1M sodium bicarbonate solution at 5 µL/min. The alkaline solution was allowed to reside in the monolith for 3 hours to quench any unreacted NHS-carbonate group. The monolith was then rinsed, at a rate of 10 µL/min, with 400 µL of a 1:1 mixture of ACN and water with 0.1% TEA, followed by 600 µL of ACN containing 0.1% TEA. After immobilization, the monoliths were stored in closed vials with a few drops of ACN with 0.1% TEA to prevent their drying. HPLC of the fractions was carried out using a Luna HILIC column (3 μm, 200 Å, 150 mm×4.6 mm) and isocratic elution with 88% B at 1 mL/min (A: 10 mM MOPS and 5 mM NaOH in water; B: 10 mM MOPS and 5 mM NaOH in ACN with 5% v/v water).

Figure 29:
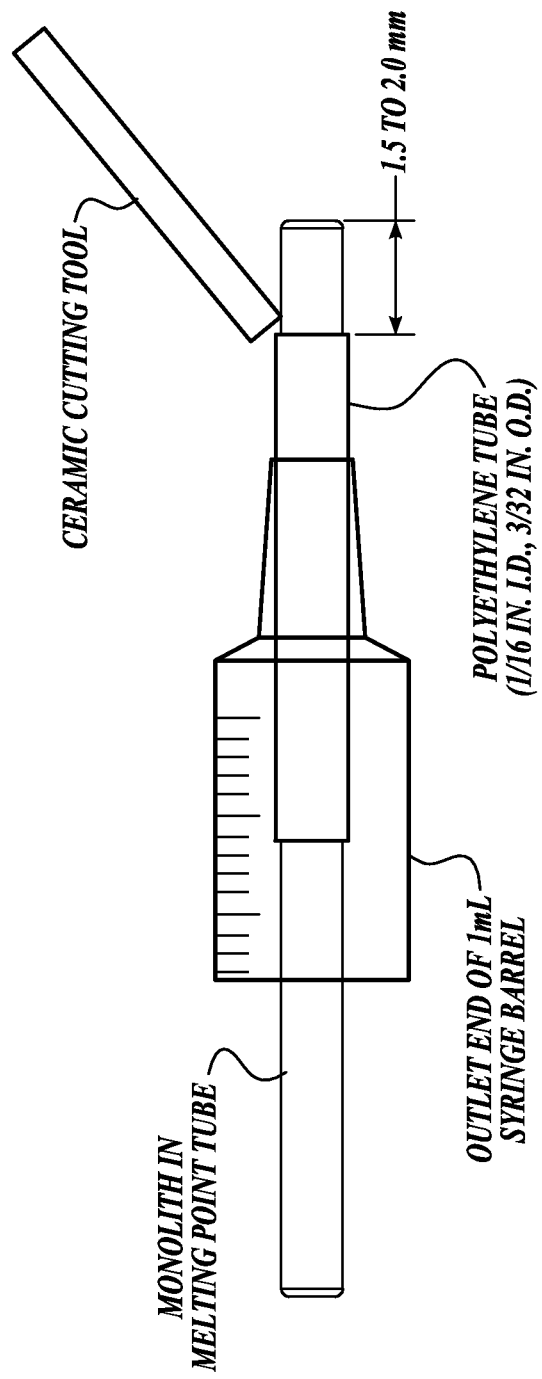
FIG. 29: Cutting of the melting point (MP) tube containing the monolith solid phase reagent using a ceramic cutting tool and a cutting guide/holder consisting of a part of a 1-mL syringe barrel and a polyethylene tube.

Determination of Cleavage Rate of the Immobilized Fluorophore. A 1.5 to 2.0 mm segment of the melting point tube containing the monolith solid phase reagent was cut using a ceramic cutting tool and a specially designed cutting guide/holder (FIG. 29). The segment was then inserted in a polyethylene tube with a 1/16 in. I.D. and 3/32 in. O.D. A 0.25 mm I.D., 1/16 in. O.D. PEEK tubing that was connected to the outlet of an HPLC pump was inserted to one end of the polyethylene tube. Another PEEK tubing of the same dimension that is connected to the inlet of a PDA detector was inserted to the other end. The PEEK tubings and the monolith segment were held in place in the polyethylene tube by inserting tightly fitting polyethylene rings around each. A 50 mM formic acid solution titrated to pH 3.1 using LiOH was flushed at a flow rate of either 0.2 or 0.5 mL/min. The signal was recorded at a detection wavelength of 507 nm.

Figure 30A:
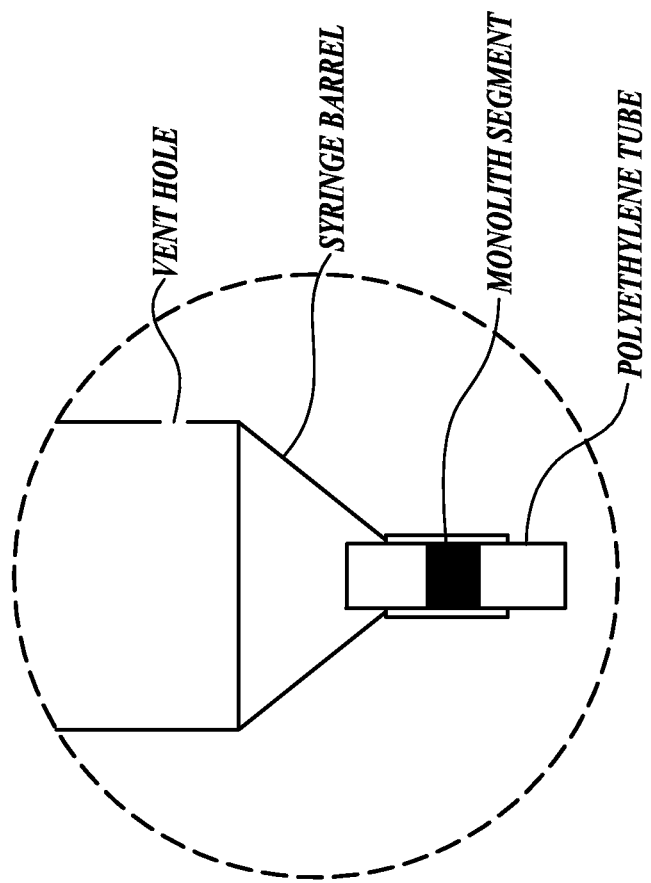
Figure 30:
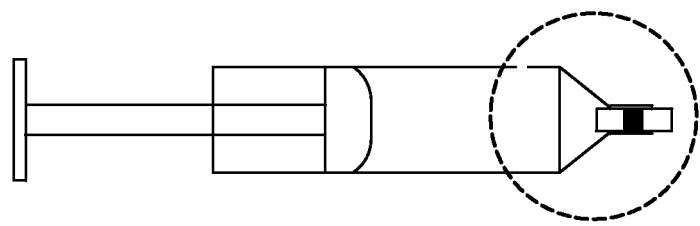

Preparation of the Monolith Pipette Tip Cartridge. The monolith in the 75 mm long MP tube was cut into short segments (~1.5 mm) using a ceramic cutting tool and cutting guide/holder (FIG. 29). A short segment was then placed in the tip of the syringe tool shown in FIGS. 30 and 30A. A polyethylene tubing with a 1/16 in. I.D. was used to keep the monolith segment tightly in place at the syringe tip. The monolith was wetted with a few microliters of water before putting the plunger into the barrel of the syringe. The vent hole in the barrel of the syringe was kept open while pushing the plunger all the way down into the syringe barrel. Then, a finger was placed over the vent hole and the plunger was pulled out, gently, but fast enough to create a good vacuum, to dislodge the monolith from the melting point tube. The monolith segment was then carefully placed into a 200 μL pipette tip, washed with 500 μL of 0.1% v/v TEA in ACN and stored in the same basic ACN solution.

Preparation of the Monolithic Support for SCaLER SPR. The 2-hydroxyethylmethacrylate (HEMA)-based monolith was chosen as a first generation solid support for the SCaLER SPR because of the ease of its activation, ease of quenching and the inertness of the hydroxyl groups which do not participate in the derivatization reaction. Monoliths that were functionalized with carboxylic acid and epoxy groups were also considered initially, but were rejected because of various concerns. Free carboxylic acid groups on the monolith surface that were not coupled to an amine during fluorophore immobilization could become activated during the final activation step of the amine-reactive group of the fluorophore and would permanently bind analytes during labeling. Glycidyl functionalities would require subsequent protection of the secondary amino groups that were formed during immobilization. There is also the possibility of forming tertiary amines which would turn the monolith into a weak anion exchanger, which would bind the multi-anionic fluorophore. The hydroxyl groups of the HEMA-based monolith, on the other hand, are passive during the final activation of the amine-reactive group of the fluorophore and their coupling with the amino group of the cleavable anchor through a carbamate group does not require any protection.

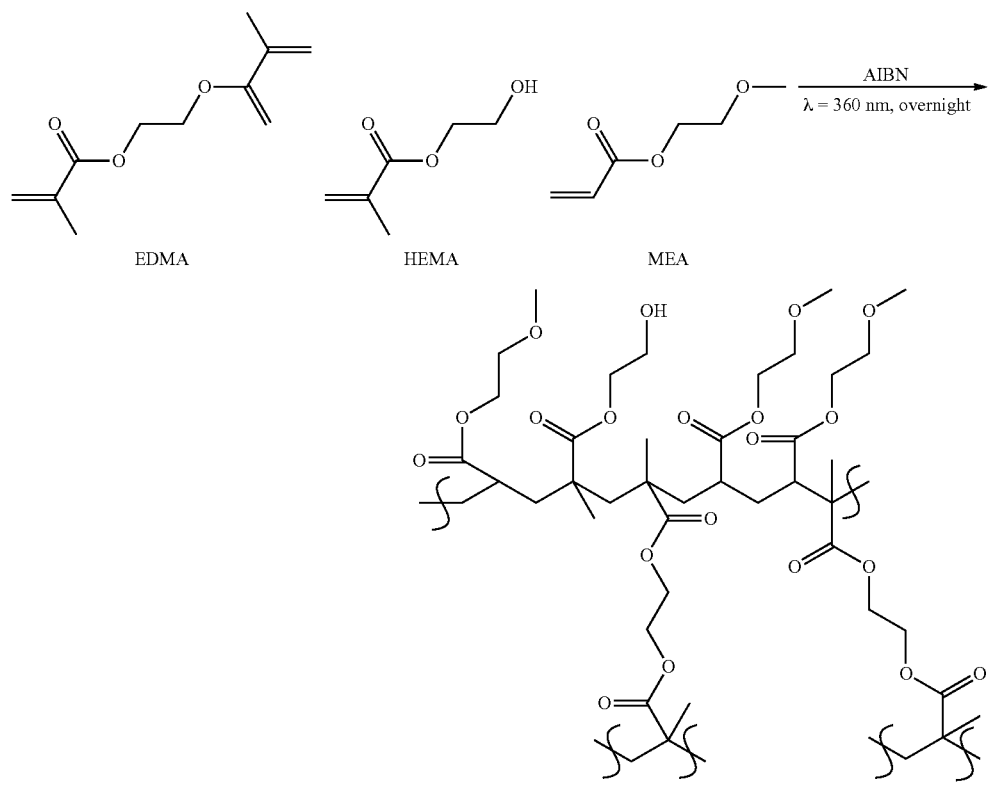

The photoinitiated free-radical polymerization of EDMA, HEMA and MEA to form HEMA-based monolith 47 is depicted above. MEA was added as an inert diluent to regulate the number of hydroxyl groups (coupling sites) on the monolith surface permitting the control, later on, of the surface density of the fluorophore. Different ratios of HEMA and MEA (10/0; 3/7 and 1/9 weight ratio) were tried and all of these monoliths had good permeability and loading of the fluorophore. Other diluents were also tested, such as acrylamide and N,N-dimethylacrylamide, but did not produce satisfactory monoliths.

Immobilization of the Fluorophore onto the Monolith Support. Activation of the hydroxyl groups on the monolith surface using N,N'-disuccinimidyl carbonate (DSC) to give activated monolith 48 was facile forming an amine-reactive carbonate ester that could react with the terminal amino group of the cleavable anchor of the fluorophore:

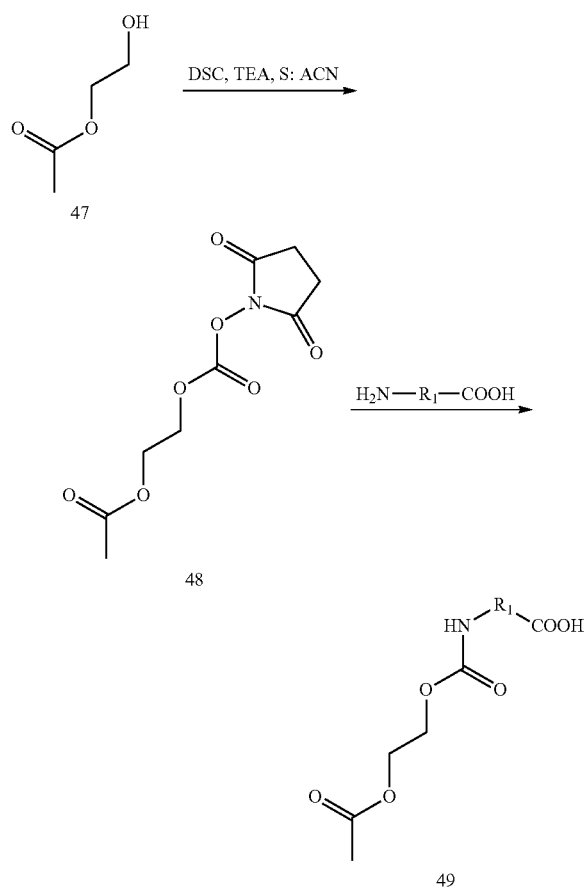

$H_2N-R_1-COOH$ = fluorophore 45

Figure 31:
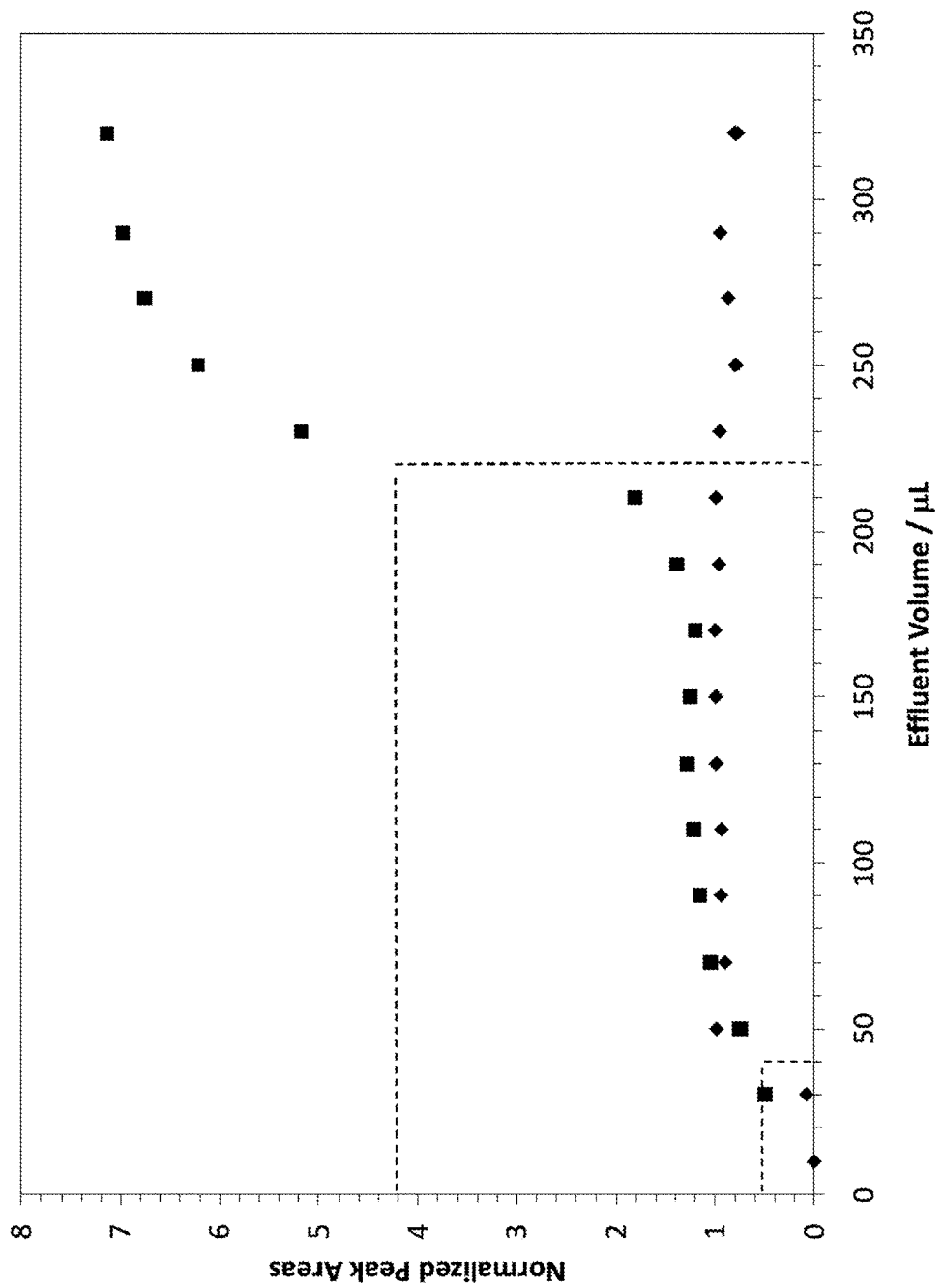
FIG. 31: Plot of the normalized peak area of the internal standard fluorophore 46 (♦) and fluorophore 45 (■) versus the effluent volume. Peak areas of 46 were normalized to the largest peak area and their respective volumes. Peak areas of 45 were normalized to the peak areas of the internal standard.

After activation of the monolith, the fluorophore was loaded for immobilization producing monolith 49. The eluent from the immobilization step was collected in 20-μL fractions except in the end where 40 μL was collected. These were then analyzed by HILIC. FIG. 31 shows the plots of the normalized peak areas of diol-terminated fluorophore 46 and amino-terminated fluorophore 45 with respect to fraction volume. Fluorophore 46, present as a hydrolysis product of fluorophore 45 in the mixture was used as an internal standard. From the plots, the approximate dead volume of the 75.4 mm long monolith column was determined to be about 40 μL, corresponding to about 0.5 μL/mm. The estimated breakthrough point (inflection point) was 220 μL. Using these values, the approximate total amount of fluorophore that was immobilized, X, can be calculated using the following equation:

$$X = C_o\left(1 - \frac{A_{min}}{A_{max}}\right)(V_{break} - V_o) \quad (4.1)$$

where $C_o$ is the concentration of fluorophore 45 in the feed, mM, $A_{min}$ is the averaged normalized area of fluorophore 45 before the breakthrough, $A_{max}$ is the maximum normalized peak area of 45, $V_{break}$ is the volume corresponding to the inflection point of the breakthrough and $V_o$ is the dead volume of the monolith column. Using a feed concentration of 10 mM an approximate total fluorophore load of 1.5 μmol (2.7 mg) or 20 nmol (36 μg) per 1 mm section was calculated. It can be seen in FIG. 31 that a small fraction of fluorophore 45 eluted out before the breakthrough. This may suggest that the rate of carbamate formation was not fast enough for the flow rate used or that there was some sort of channeling in the monolith column.

Figure 32C:
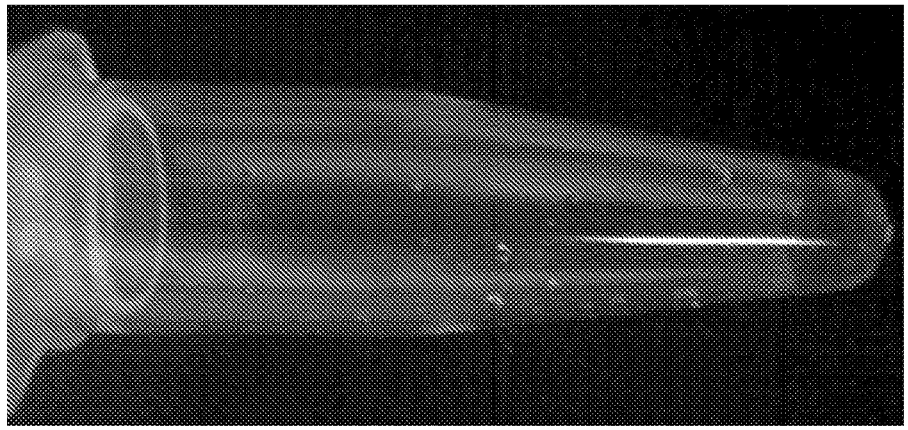
FIG. 32A, FIG. 32B, and FIG. 32C: Photograph of the pipette tip monolithic SPR with the immobilized fluorophore (FIG. 32A) and after cleaving off the fluorophore (FIG. 32B). The 10-μL volume of the cleaving solution used was collected in a 0.2 mL tube (FIG. 32C).
Figure 32B:
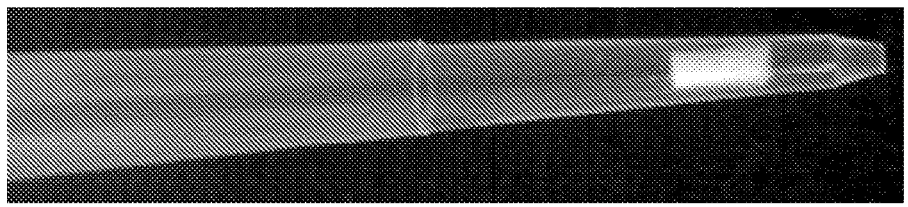
Figure 32A:
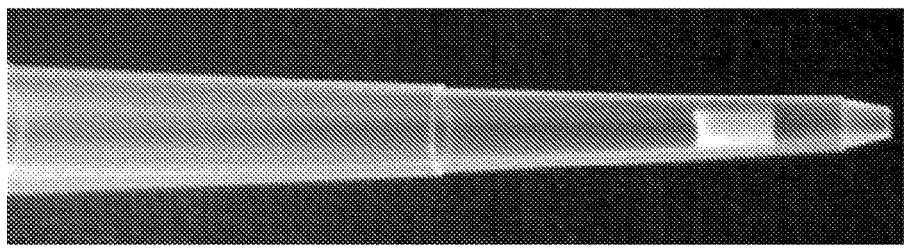
Figure 33C:
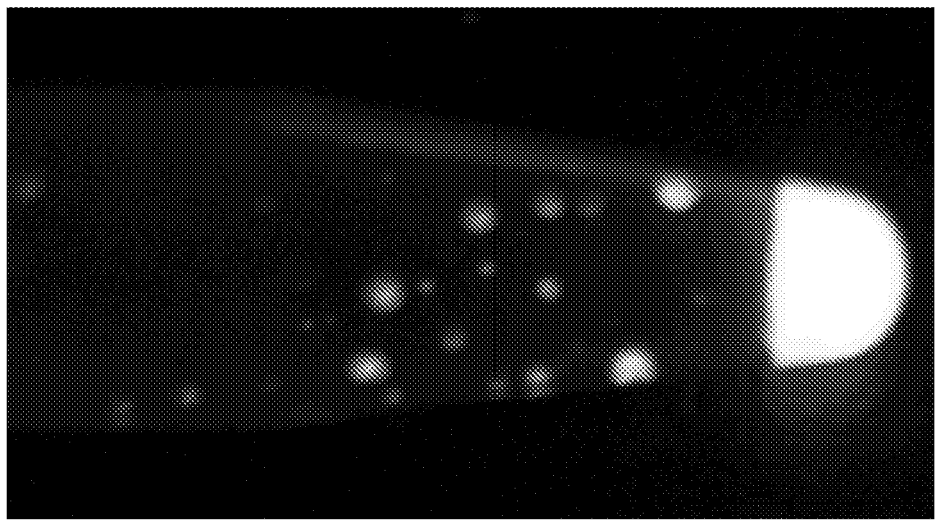
FIG. 33A, FIG. 33B, and FIG. 33C: Photograph of the pipette tip monolithic SPR shown in FIG. 49 under a UV lamp. The designations are the same as in FIG. 49.
Figure 33B:
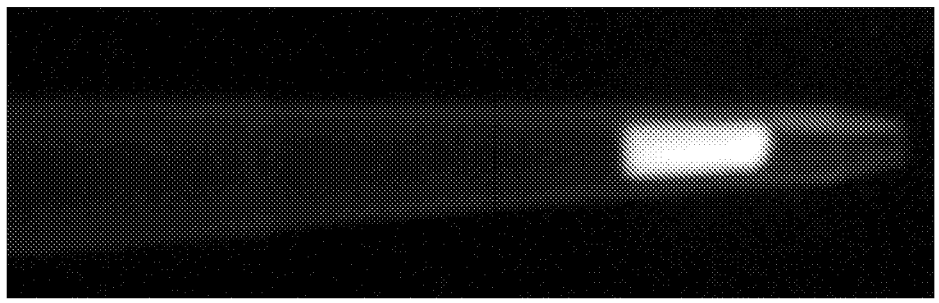
Figure 33A:
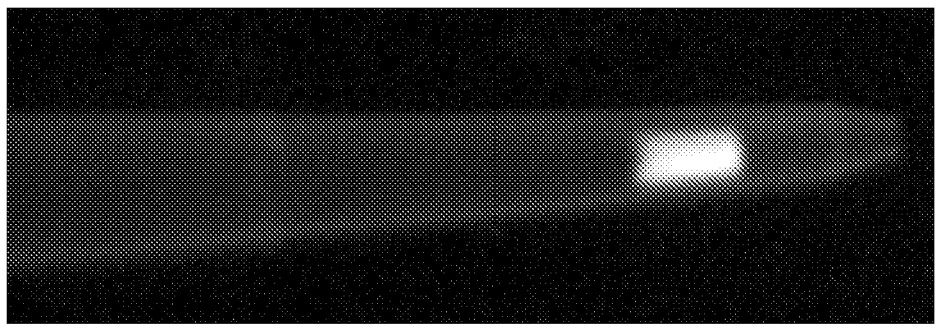

Format of the Monolithic SPR. A large diameter (~1 mm), shallow bed format was selected for the monolithic SPR over a format that has a small diameter and deep bed (e.g., 100 μm capillaries). The shallow bed format makes elution of reagents, solvents and samples through the SPR easier. The pipette tip SPR format shown in FIGS. 32A, 32B, and 32C allowed easy loading of the reagents and solvents and easy collection of the effluents. It can be seen that the SPR with the immobilized fluorophore has an orange color and one that has been treated with 3 μL of 1M acetic acid and washed with 7 μL of water had almost no color. The same SPRs were also placed under a UV lamp (FIGS. 33A, 33B, and 33C). The monolith with the fluorophore still attached had orange color while the one whose fluorophore had been removed had a faint light yellow green color. The eluted cleaving and wash solution (mixture of 3 μL of 1M acetic acid and 7 μL of water) had an intense yellow green fluorescence. The spent monolith bed had a faint fluorescence because the 7 μL water wash still left some of the fluorophore in the monolith bed.

Figure 34:
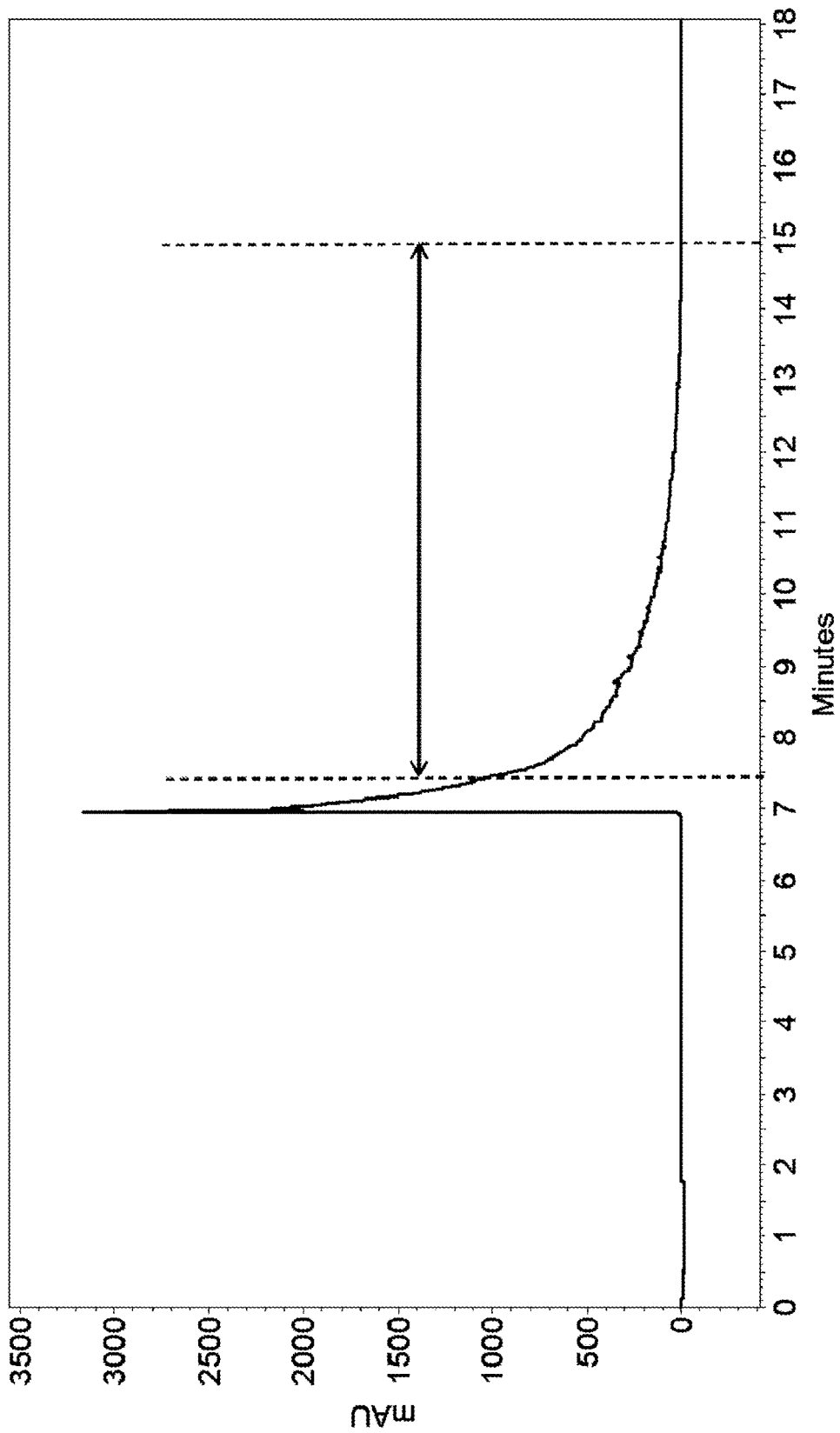
FIG. 34: PDA (photodiode array) signal at 507 nm obtained for the cleaving effluent leaving the 1.5 mm long SPR segment. A pH 3.1 buffer was used as cleaving solution and eluent.

Rate of Cleavage of the Cleavable Group After Immobilization. Cleavage of the dioxolane group was re-examined to ascertain that formation of the carbamate bond, the close proximity of the solid surface or any other unforeseen or unknown factor associated with the immobilization step did not alter its cleavability at low pH. A short monolith segment (~1.5 mm) was connected in between an HPLC pump and a photo diode detector. A pH 3.1 buffer was flushed through at either 0.2 or 0.5 mL/min flow rate and the detector trace was recorded as displayed in FIG. 34. The segment of the detector trace where the PDA signal was no longer overloaded yet the fluorophore was still readily detectable (the section between the two vertical dashed lines in FIG. 34, which is between 7.2 and 15.0 min) was used to determine the pseudo first order rate constant of the cleavage reaction. The time at the start of the curve is designated as t=0 and the time at the end of the curve as t=15.0–7.2 min=7.8 min. Because the curve represents the concentration of the cleaved fluorophore (the product) with the passage of time, and not that of the immobilized fluorophore (the starting material or reactant), the latter has yet to be determined to get the rate of cleavage. Therefore, the area under the curve from FIG. 34 was calculated using Simpson's rule. The curve was divided into short, equal time segments of $\Delta t=1/240$ min. The average absorbance signal in each of these segments, $S(t)$, and $\Delta t$ were then used to calculate the total area under the curve, $A_{total}$, using the following equation:

$$A_{total} = \sum_{t=m}^{n} S(t)\Delta t = \sum_{t=m}^{n} A(t) \quad (4.2)$$

where m is the time at the beginning of the curve, designated as 0 min., n is the time at the end of the curve, 7.8 min, and $A(t)$ is the area under the curve at a given time. $A_{total}$ is the area that represents the concentration of the immobilized fluorophore at $t=0$ min. To find the corresponding area of the immobilized fluorophore as a function of time, $A_{immob}(t)$, the following equation was used:

$$A_{immob}(t) = A_{total} - \sum_{t=m}^{n} A(t) \quad (4.3)$$

Figure 35:
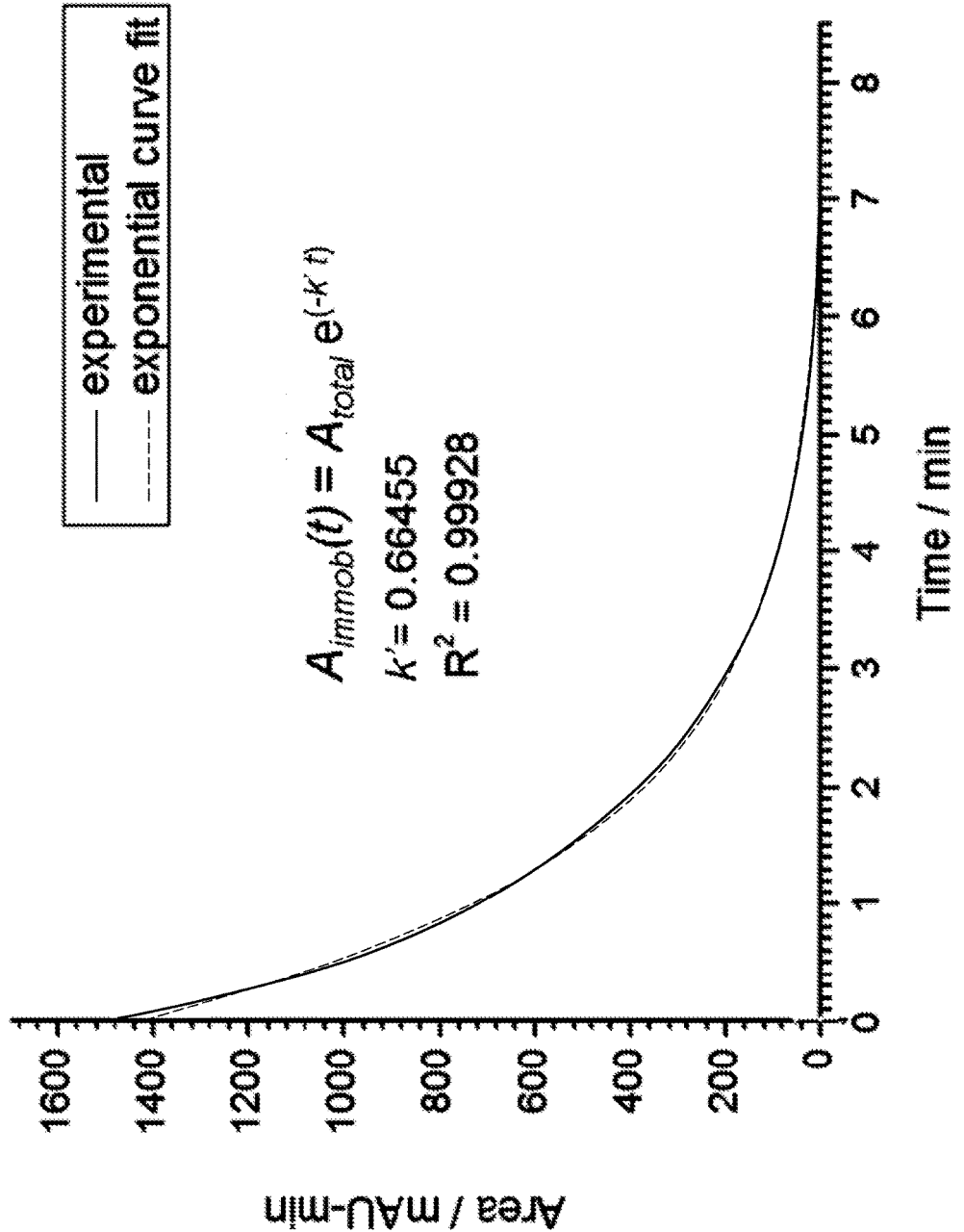
FIG. 35: Plot of $A_{immob}(t)$ with respect to time. $A_{immob}(t)$ is the area that represents the concentration of the fluorophore as a function of time.

$A_{immob}(t)$ was then plotted against time in FIG. 35 and fitted with an exponential decay curve using Equation 4.1. A k' of 0.65 was obtained (for n=3, k'=0.65, RSD=2.3%) leading to a $t_{0.5}$ and $t_{0.01}$ of 1.1 and 7.1 min, respectively. These agree with the values determined for the cleavable anchor in free solution (1.0 and 6.5 min, Rationale for the Direct Attachment of the Cleavable Anchor to the Fluorophore section above, Table 4). Thus, immobilization did not alter the cleavability of the dioxolane ring and mild conditions can still be used to cleave off the fluorophore.

Example 9: Exemplary SCaLER SPR Labeling Tests

Activation of the Fluorophore. Using a gel loader pipette tip, 50 μL ACN with 0.1% v/v TEA was added over the monolith segment in the SCaLER SPR pipette tip cartridge and eluted through it using a 200 μL autopipette by pushing the plunger of the autopipet down to the first stop. An activating mixture containing 1.7 μL pentafluorophenyl trifluoroacetate, 96 μL anhydrous ACN and 2.8 μL TEA was prepared. A 50 μL aliquot of this solution was loaded into the pipette tip cartridge and slowly eluted through the monolith segment in the span of 1 min. The monolith segment was then washed by eluting, three times, with 50 μL of ACN that contained 0.1% v/v TEA. If the SPR was used for labeling immediately after activation, the cartridge was emptied out. Otherwise, it was kept immersed in the ACN/TEA wash/storage solution.

Labeling of Small Amines. A solution of the amine(s) in 0.1M aqueous sodium bicarbonate (pH 9) was loaded into the SPR cartridge using a gel loader pipette tip. The outlet of the SPR cartridge was placed into a collection vial and the sample solution was eluted through it by depressing the plunger of the autopipette to the first stop. The eluted sample was recycled five to twenty times by pipetting it back into the SPR cartridge, depending on the experiment. After labeling, the SPR cartridge was washed with 50 μL of the labeling buffer that was used to prepare the amine sample. The SPR was then quenched by eluting it with 50 μL of 0.1M morpholine in ACN that contained 0.1% v/v TEA. The quenching step was repeated two more times, then the SPR cartridge was washed with 50 μL 0.1% v/v TEA in ACN, followed by 50 μL of 0.1M aqueous sodium bicarbonate solution and 50 μL of water to remove the salts and buffer. The quenched label and the labeled analytes were then cleaved off by loading 3 μL of a 0.1M solution of acetic acid in water directly on top of the SPR (excluding all air bubbles) and eluting a part of the acidic solution through the monolith segment to soak it. The acidic solution was allowed to stand in the monolith for a few minutes to maximize cleavage. The rest of the acidic solution was eluted out into a collection vial, followed by 7 μL wash water, and the combined collected solution was analyzed by CE.

Labeling of Diamines at Low Concentrations. A series of samples having a range of concentrations of 1-methylpiperazine (MP) (from 1 mM down to 1 nM) were prepared. The concentration of AEM, which was used as an internal standard, was kept constant at 10 μM. For the 1 μM to 1 mM MP solutions 20 μL volumes were injected onto the SPR cartridges, for the 1 nM and 10 μM MP solutions 200 μL volumes were used following the procedure in the Labeling of Small Amines section.

Labeling of Amino Acids. Amino acids were labeled the same way as in the Labeling of Small Amines section except that the labeling buffer used was a mixture of 8 parts (v/v) of 25 mM 3-(dimethylamino)-1,2-propanediol titrated to pH 9 with acetic acid and 2 parts (v/v) of water. Also, the quenching solution contained 2 parts (v/v) of 250 mM taurine in water and 8 parts (v/v) of 125 mM 3-(dimethylamino)-1,2-propanediol in ACN.

Labeling of N-Acetyl-L-Lysine-Amide. The lysine residue mimic, N-acetyl-L-lysine-amide, was labeled as described for the Labeling of Small Amines, except the labeling buffer contained 3 parts (v/v) of 50 mM boric acid titrated to pH 9 with NaOH and 7 parts (v/v) of ACN.

Activation of the SCaLER SPR Amine-Reactive Group. The activation of the carboxylic acid group of the fluorophore to form the activated SCaLER SPR 50 was accomplished by the use of pentafluorophenyl trifluoroacetate (PFP-TFA) with TEA as base as depicted below:

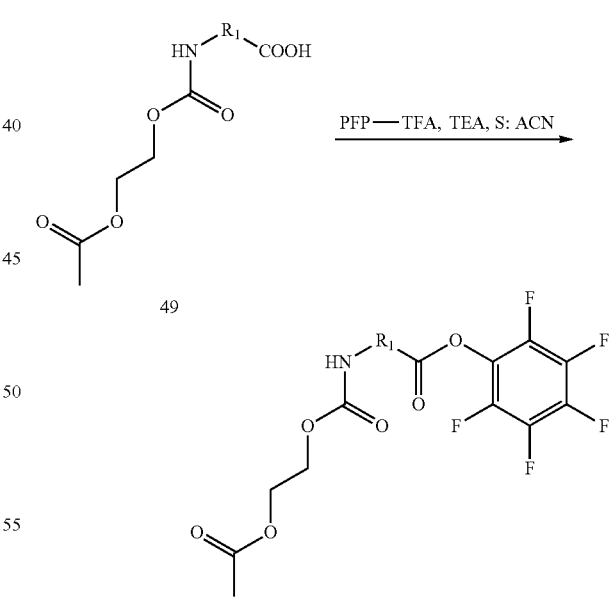

where ——HN—$R_1$—COO—— is the fluorophore

The use of base was necessary to prevent premature cleavage of the cleavable anchor due to the presence of trifluoroacetic acid and pentafluorophenol from any PFP-TFA hydrolysis. The PFP-TFA activation method gave cleaner activated ester products under basic conditions than those that used carbodiimide. In previous tests with a similar pyrene derivative, 1-ethyl-3-(3-dimethylaminopropyl)carbodiimide (EDC) under basic conditions resulted in the formation of stable N-acylurea type adducts with the carboxylate of the fluorophore. The resulting fluorophore pentafluorophenyl ester was also found to be significantly more stable under alkaline conditions than the NHS ester.

Figure 36:
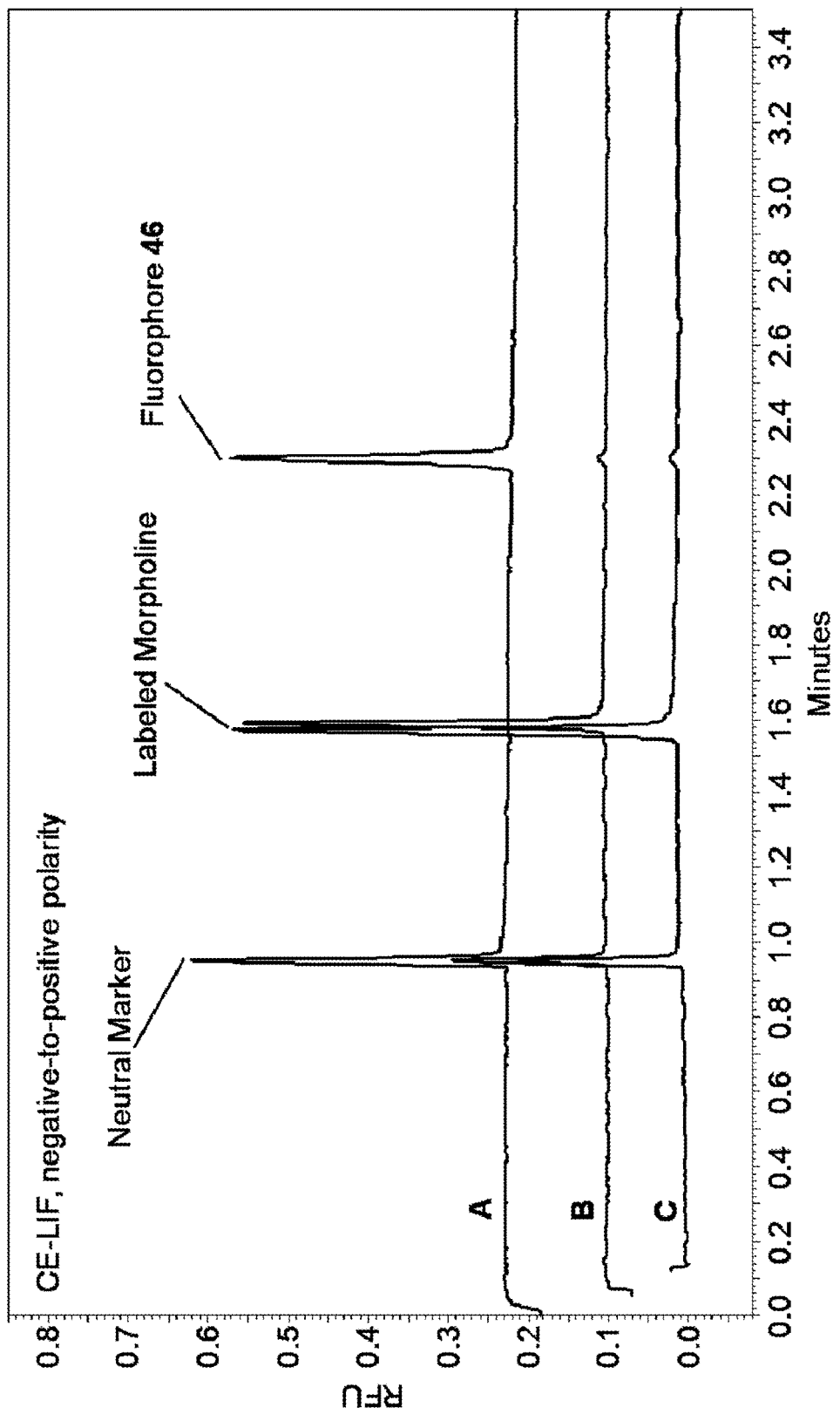
FIG. 36: CE-LIF analysis of the cleaving solutions of an unactivated SCaLER SPR (A), SPR quenched with morpholine immediately after activation (B) and SPR quenched with morpholine 100 minutes after activation (C). The fluorescent neutral marker is a trisulfonamide derivative of APTS obtained with diethanolamine.

To determine the degree of activation, SPR 50 was reacted with an excess of morpholine. CE-LIF analysis revealed that relative to the labeled morpholine there was very little of the free carboxylic acid in the cleaving solution when morpholine quenching occurred right after activation (FIG. 36, A). This indicates complete activation of the fluorophore in the SPR. The short-term stability of the PFP-ester was determined in the storage solution, 0.1% v/v TEA in ACN, for 100 mM, which was a conservative representation of any lag time between SPR activation and sample loading due to sample preparation. CE-LIF analysis of the cleaving solution obtained when morpholine quenching was done 2 hours after the activation is shown in FIG. 36, electropherogram B. The result showed that the PFP-ester is indeed stable in the storage solution.

Figure 37:
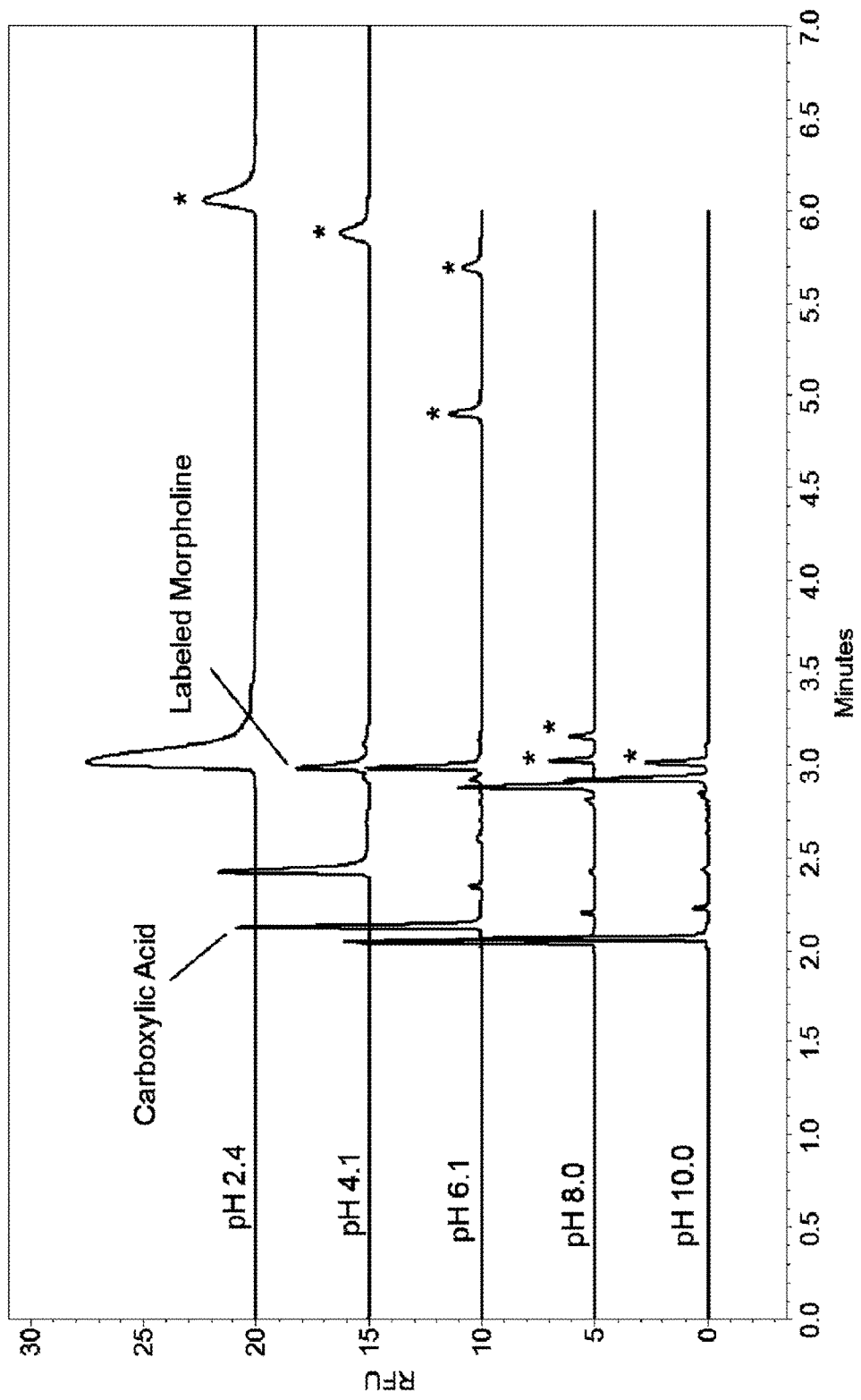
FIG. 37: CE-LIF analysis, at different pH values, of the cleaving solutions obtained from the diamine labeling experiments.

Labeling of Diamines and Their Analysis by CE-LIF at Different pH Values. A mixture of the diamines, AEM and MP, were labeled using the SCaLER SPR and the cleaved solution was analyzed in buffers having different pH values, the same way it was done with fluorophore 33. The pH values ranged from 2 to 10 to represent the entire operating pH range for CE. The electropherograms, which are overlaid in FIG. 37, showed comparable fluorescence intensity between runs signifying that fluorescence is independent of the pH. The peak position of the labeled morpholine, whose charge is solely from the fluorophore, is also the same for all the runs indicating that the charge state of the fluorophore is also pH-independent. As with fluorophore 33, CE separation selectivity for the labeled diamines (marked with *) changed with pH and had a maximum in the 6.1<pH<8.0 range.

Labeling of Diamines at Low Concentrations. To test the ability of SCaLER SPR to label amines at low concentrations, solutions having both diamines AEM and MP were used as samples. The concentration of MP was decreased from 1 mM down to 1 nM. That of AEM, which was used as internal standard, was kept constant in all of the samples. The sample with the higher concentatrations of MP was labeled using only 20 μL aliquots. To improve detection, samples with the lower concentration of MP were labeled using 200 μL aliquots.

Figure 38:
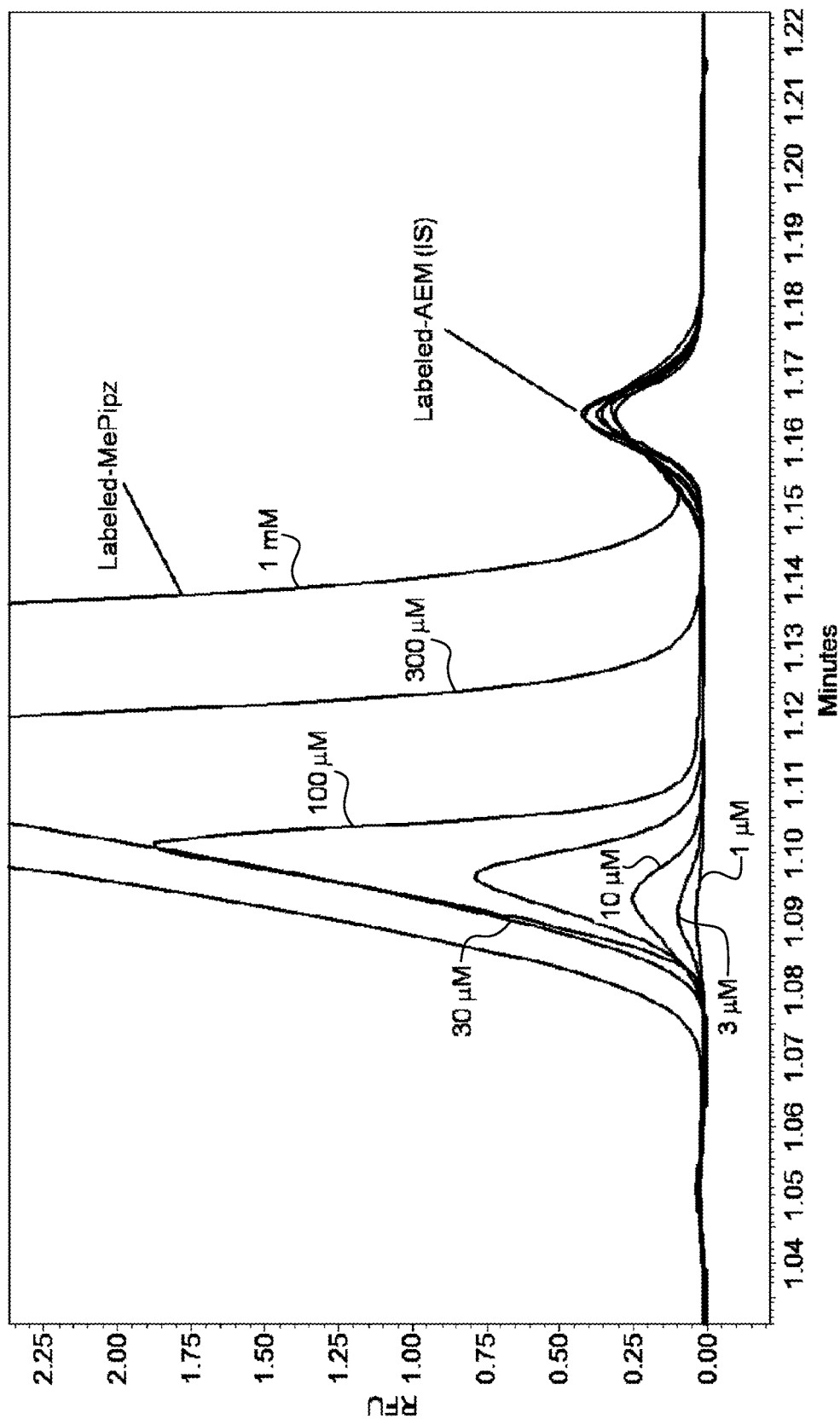
FIG. 38: CE-LIF analysis of the cleaving solutions from the labeling of the diamine samples having concentrations from 1 mM down to 1 μM. The electropherograms are normalized to the area of the labeled AEM peak.
Figure 39:
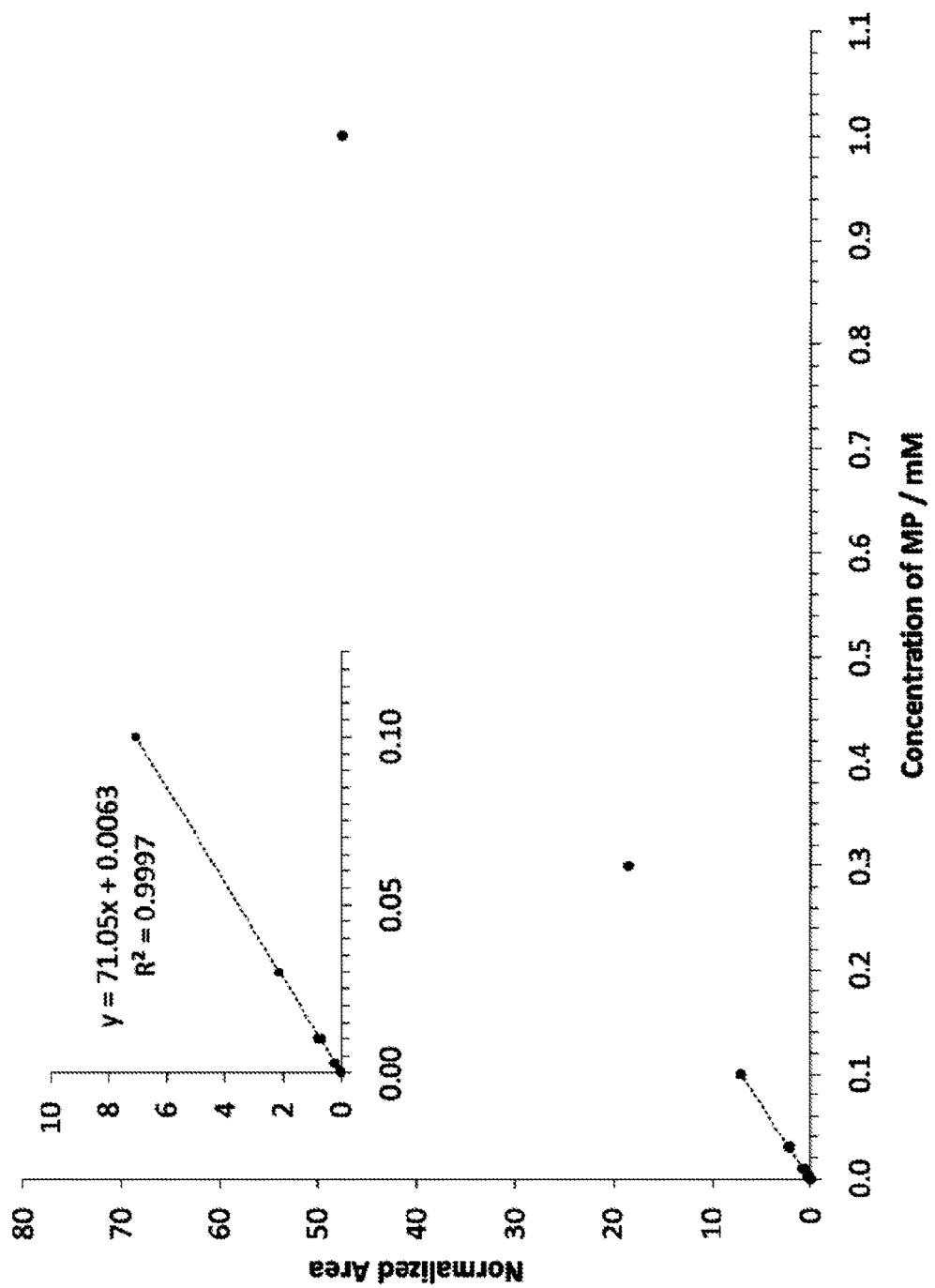
FIG. 39: Plot of the normalized peak areas of MP against their concentrations. Inset is an expansion for the concentration range of 0 to 0.1 mM. The trend line was fitted from $1 \times 10^{-5}$ to 0.1 mM (10 nM to 100 μM). The two highest concentration data points deviate from this linearity and are not included in the fit.

A portion of the electropherograms of the 20-μL set of samples is shown in FIG. 38. As expected, the size of the peak corresponding to labeled MP went down relative to that of AEM (internal standard) as the concentration of the sample was decreased from 1 mM to 1 μM. The samples for the 200-μL set were also analyzed the same way. When the normalized peak areas of MP were plotted against concentration (FIG. 39), a linear relationship was obtained from 10 nM up to 100 μM. Samples with higher concentrations showed a nonlinearity: it could be caused by incomplete labeling due to depletion of the active fluorophore in the SPR. The data for the 1 nM sample was not included because it was below the LOQ (S/N=10). FIG. 39 demonstrates the dynamic range of the labeling of MP and its CE-LIF analysis which is about 4 orders of magnitude. The lower limit of this range could still be improved (lowered) by using a 560 nm emission-side filter, a larger diameter capillary for the CE analysis and employing on-line preconentration techniques. The reproducibility of the relative peak areas of the CE-LIF analyses were found to be about ±0.2%.

Figure 40:
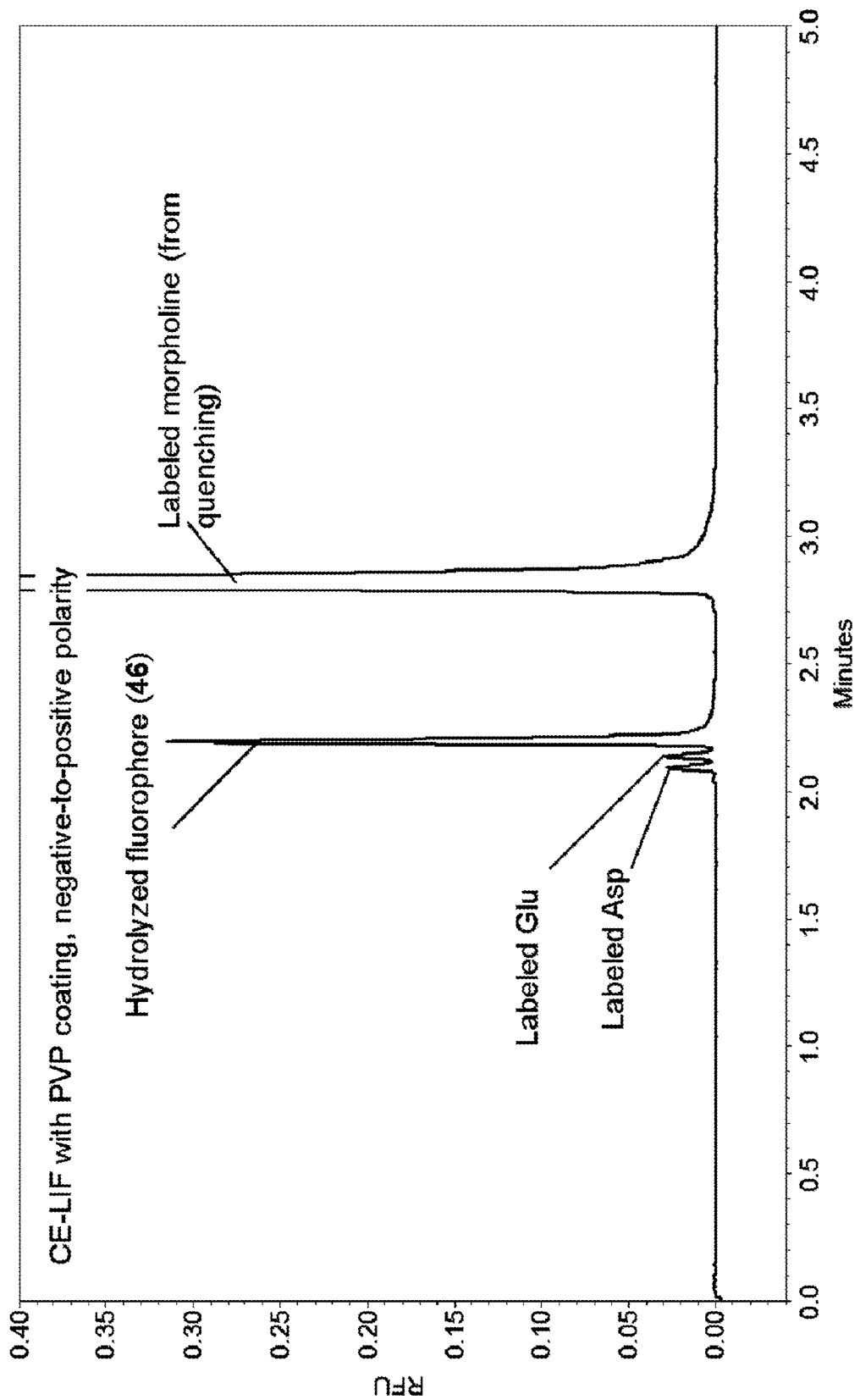
FIG. 40: CE-LIF of cleaving solution from the labeling of a 20 μL sample of 0.2 mM aspartic and glutamic acid. BGE: 12.5 mM acetic acid titrated to pH 4.5 with LiOH.
Figure 41:
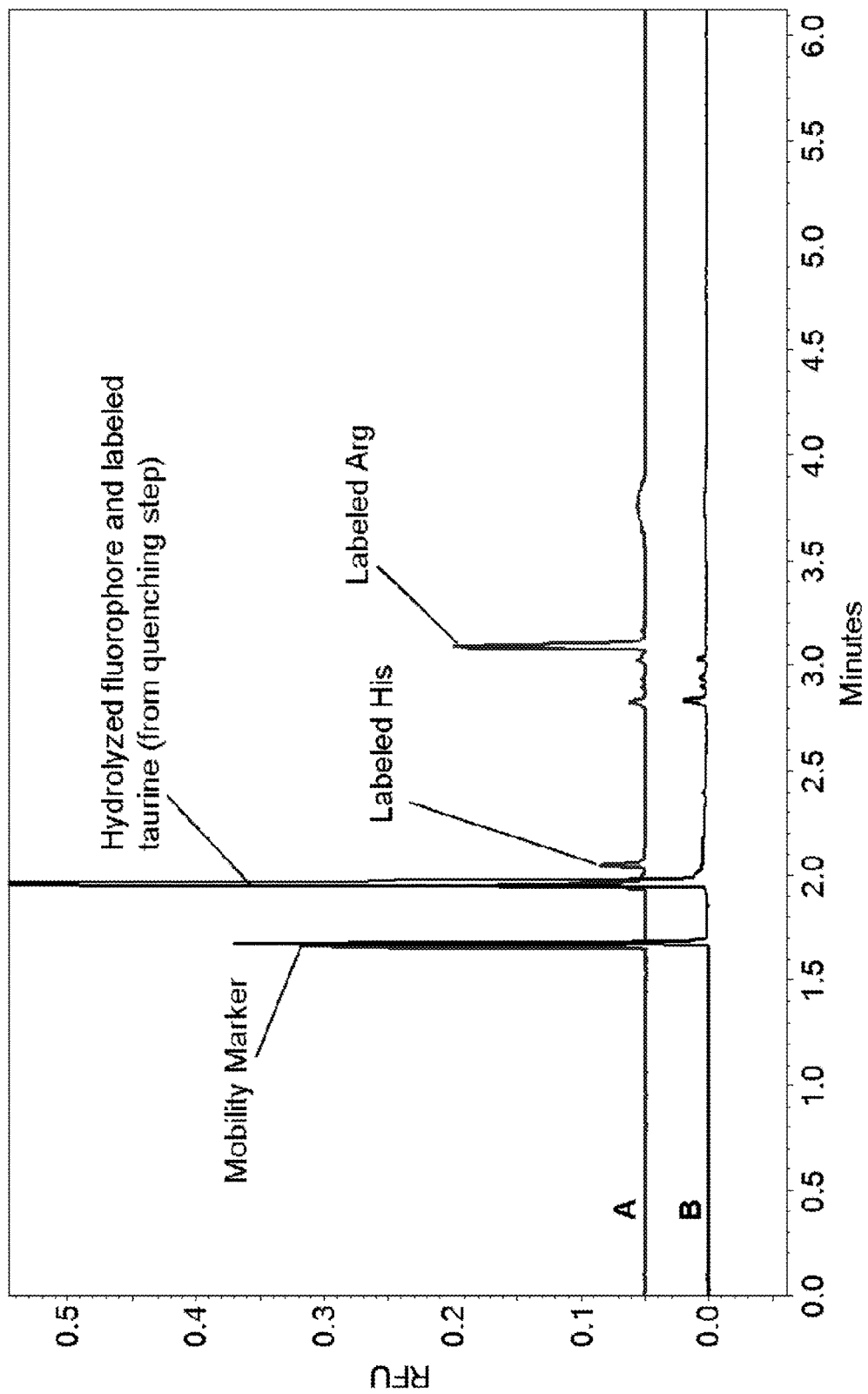
FIG. 41: CE-LIF of the cleaving solution from the labeling of a 20 μL sample of 0.2 mM histidine and arginine. BGE: 13 mM CHES titrated to pH 4.5 with LiOH.

Labeling of Amino Acids. Labeling tests using the SPR were done on aspartic and glutamic acid. Since the molecular weights of the labeled analytes are very similar, CE separation selectivity was based on their charge difference. The pH of the background electrolyte that led to maximum separation selectivity was determined by analyzing the samples at different pH values as described in labeling of Diamines and Their Analysis by CE-LIF at Different pH Values above, except a narrower pH range was used. The CE-LIF analysis at pH 4.5 is shown in FIG. 40 indicating good separation selectivity. Histidine and arginine were also derivatized and analyzed by CE-LIF (FIG. 41) at pH 10 where separation selectivity was good.

Figure 42:
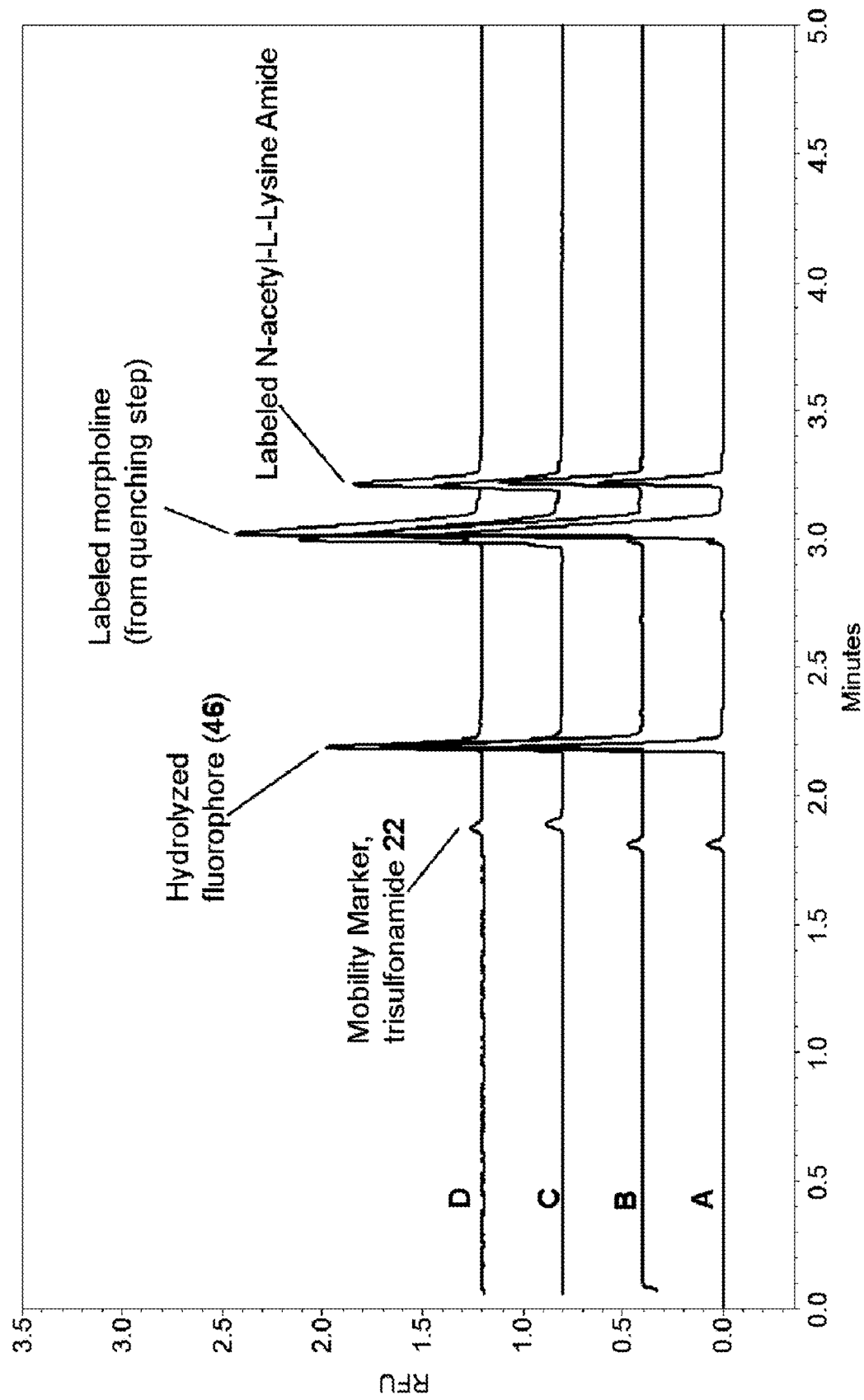
FIG. 42: CE-LIF of cleaving solution from the labeling of a 20 μL solution of 0.2 mM N-acetyl-L-lysine amide. Different labeling reactions whose samples were passed through the SPR twice (A), 5 times (B), 10 times (C) and 20 times (D) were conducted.

To mimic the reactivity of the ε-amino groups of lysine residues in proteins and peptides, N-acetyl-L-lysine amide was labeled. Four labeling experiments were conducted with increasing number of passes of the sample through the SPR. FIG. 42 shows that there is practically no change in the peak areas between the $2^{nd}$ and $20^{th}$ pass indicating that labeling was already complete at the $2^{nd}$ pass and demonstrating that the fluorophore is very reactive toward the ε-amino groups of lysine residues.

While illustrative embodiments have been illustrated and described, it will be appreciated that various changes can be made therein without departing from the spirit and scope of the invention.

The invention claimed is:

1. A solid phase reagent for simultaneously capturing and fluorescently monolabeling an analyte having multiple reactive sites, comprising a solid phase and a plurality of moieties tethered to the solid phase, wherein each moiety of the plurality of moieties comprises:
   (a) a single analyte-reactive group for capturing an analyte to provide a captured analyte having a gyration radius,
   (b) a single fluorescent group, and
   (c) a single cleavable anchor group,
   wherein
   the analyte-reactive group is covalently attached to the fluorescent group either directly or indirectly, and wherein any two analyte-reactive groups of the plurality of moieties are separated by a distance greater than the gyration radius of the captured analyte;
   the fluorescent group is covalently attached to the cleavable anchor group either directly or through a first spacer; and
   the cleavable anchor group is covalently attached to the solid phase either directly or through a second spacer, and
   wherein the fluorescent group is selected from the group consisting of:

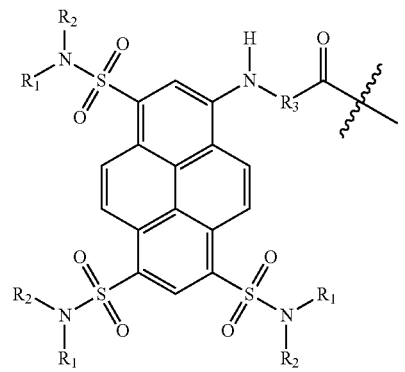

and

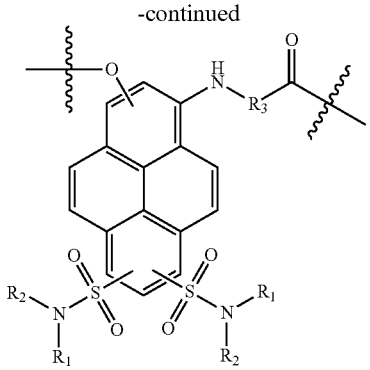

wherein:
R$_1$, independently at each occurrence, is hydrogen, alkyl$_{C1-12}$, or hetero(backbone)alkyl$_{C1-12}$, wherein when substituted, at least one hydrogen atom of the alkyl$_{C1-12}$, or hetero(backbone)alkyl$_{C1-12}$ moiety is replaced with a functional group carrying a net zero, net negative, or net positive charge;

R$_2$, independently at each occurrence, is hydrogen, alkyl$_{C1-12}$, or hetero(backbone)alkyl$_{C1-12}$, wherein when substituted, at least one hydrogen atom of the alkyl$_{C1-12}$, or hetero(backbone)alkyl$_{C1-12}$ moiety is replaced with a functional group carrying a net zero, net negative, or net positive charge; and R$_3$ is divalent alkyl$_{C1-12}$ or divalent hetero(backbone) alkyl$_{C1-12}$.

2. The solid phase reagent of claim 1, wherein the functional group is a carboxylate, a sulfonate, a sulfate, a primary amino group, a secondary amino group, or a tertiary amino group.

3. The solid phase reagent of claim 1, wherein the analyte-reactive group is an amine-reactive group.

4. The solid phase reagent of claim 1, wherein the solid phase is selected from the group consisting of a particle-based porous solid phase, a monolith porous solid phase, and a gel.

5. The solid phase reagent of claim 1, wherein the first spacer, the second spacer, or both comprise an oligo(oxyethylene) group with a mer-number between 1 and 100.

6. The solid phase reagent of claim 1, wherein the cleavable anchor group is a 1,3-dioxolane selected from the group consisting of

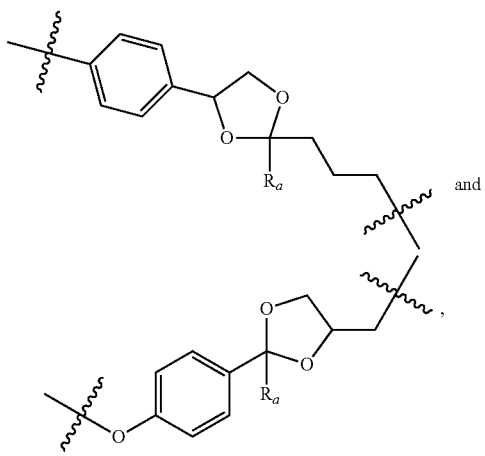

wherein R$_a$ is selected from the group consisting of
(a) H and
(b) CH$_3$.

7. The solid phase reagent of claim 1, wherein the solid phase is a monolith solid phase comprising a functional group selected from the group consisting of epoxy, carboxylic acid, hydroxyl, and combinations thereof.

8. The solid phase reagent of claim 1, wherein the solid phase is a 2-hydroxyethylmethacrylate-based monolith solid phase.

9. A method of simultaneously immobilizing and fluorescently monolabeling an analyte having multiple reactive sites in an analyte-containing solution, comprising:
(a) contacting an analyte having multiple reactive sites with a solid phase reagent of claim 1;
(b) reacting the analyte with an analyte-reactive group of the solid phase reagent to provide an immobilized monolabeled analyte;
(c) reacting any analyte-reactive group of the solid phase reagent not reacted with the analyte with a quencher to provide quenched analyte-reactive groups;
(d) releasing the immobilized monolabeled analyte and quenched analyte-reactive groups from the porous solid phase by cleaving the cleavable anchor group to provide a monolabeled analyte; and
(e) isolating or analyzing the monolabeled analyte.

10. The method of claim 9 further comprising analyzing the monolabeled analyte by a method selected from the group consisting of capillary electrophoresis, liquid chromatography, absorption spectroscopy, fluorescence spectroscopy, mass spectrometry, and combinations thereof.

11. The method of claim 9, wherein the analyte comprises an amino group that reacts with the analyte-reactive group.

12. The method of claim 9, wherein the analyte is selected from the group consisting of a peptide, a protein, and a carbohydrate.

13. The method of claim 9, wherein the solid phase is a porous solid phase.

14. The method of claim 9, wherein the solid phase is a gel.

15. A solid phase reagent for simultaneously capturing and fluorescently monolabeling an analyte having multiple reactive sites, comprising a solid phase and a plurality of moieties tethered to the solid phase, wherein each moiety of the plurality of moieties comprises:
(a) a single analyte-reactive group for capturing an analyte to provide a captured analyte having a gyration radius,
(b) a single fluorescent group, and
(c) a single cleavable anchor group,
wherein
the analyte-reactive group is covalently attached to the fluorescent group either directly or indirectly, and wherein any two analyte-reactive groups of the plurality of moieties are separated by a distance greater than the gyration radius of the captured analyte;
the fluorescent group is covalently attached to the cleavable anchor group either directly or through a first spacer; and
the cleavable anchor group is covalently attached to the solid phase either directly or through a second spacer, and wherein the fluorescent group is:

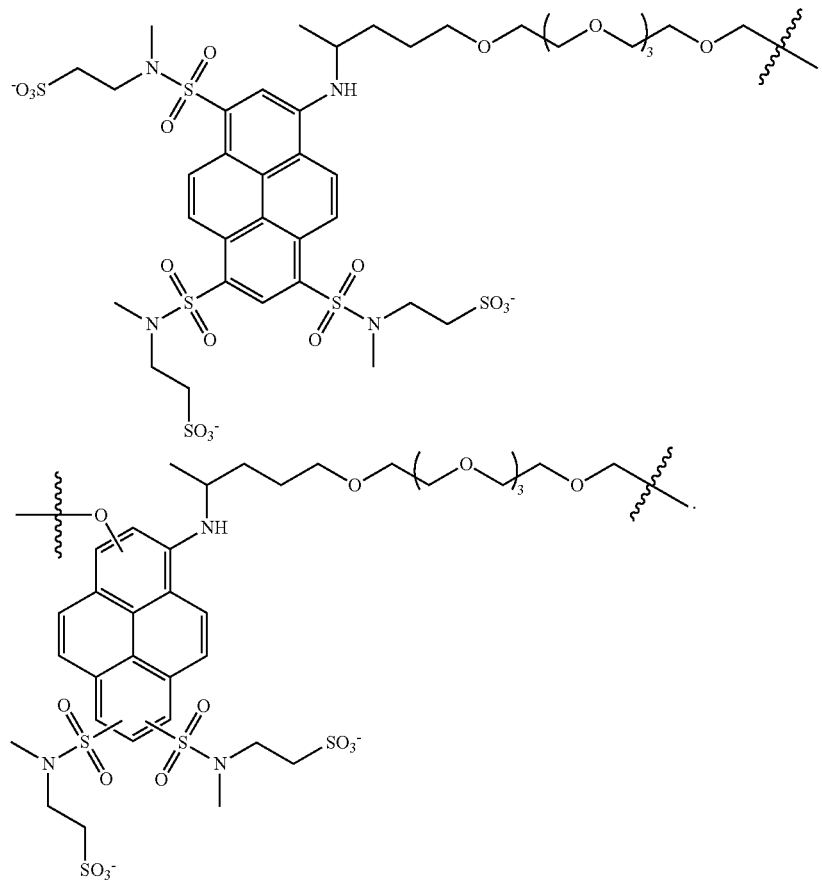

or

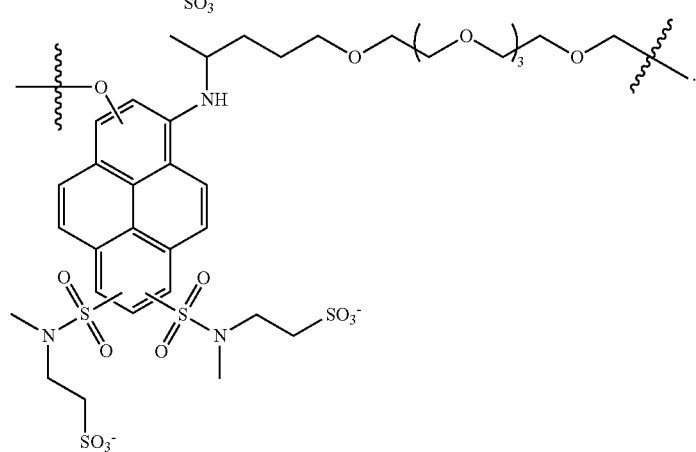

16. The solid phase reagent of claim 15, wherein the analyte-reactive group is an amine-reactive group.

17. The solid phase reagent of claim 15, wherein the solid phase is selected from the group consisting of a particle-based porous solid phase, a monolith porous solid phase, and a gel.

18. The solid phase reagent of claim 15, wherein the first spacer, the second spacer, or both comprise an oligo(oxyethylene) group with a mer-number between 1 and 100.

19. The solid phase reagent of claim 15, wherein the cleavable anchor group is a 1,3-dioxolane selected from the group consisting of

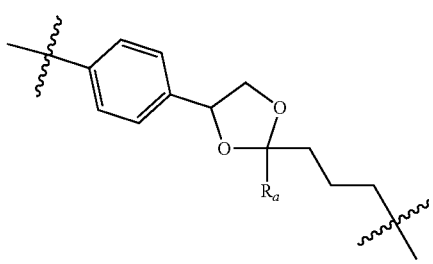

and

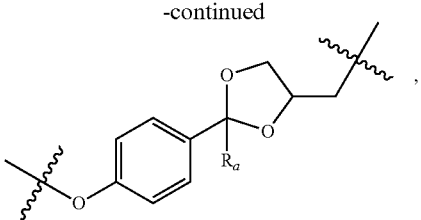

wherein $R_a$ is selected from the group consisting of
(a) H and
(b) $CH_3$.

20. The solid phase reagent of claim 15, wherein the solid phase is a monolith solid phase comprising a functional group selected from the group consisting of epoxy, carboxylic acid, hydroxyl, and combinations thereof.

21. The solid phase reagent of claim 15, wherein the solid phase is a 2-hydroxyethylmethacrylate-based monolith solid phase.

22. A method of simultaneously immobilizing and fluorescently monolabeling an analyte having multiple reactive sites in an analyte-containing solution, comprising:
(a) contacting an analyte having multiple reactive sites with a solid phase reagent of claim 15;
(b) reacting the analyte with an analyte-reactive group of the solid phase reagent to provide an immobilized monolabeled analyte;

(c) reacting any analyte-reactive group of the solid phase reagent not reacted with the analyte with a quencher to provide quenched analyte-reactive groups;

(d) releasing the immobilized monolabeled analyte and quenched analyte-reactive groups from the porous solid phase by cleaving the cleavable anchor group to provide a monolabeled analyte; and (e) isolating or analyzing the monolabeled analyte.

23. The method of claim 22 further comprising analyzing the monolabeled analyte by a method selected from the group consisting of capillary electrophoresis, liquid chromatography, absorption spectroscopy, fluorescence spectroscopy, mass spectrometry, and combinations thereof.

24. The method of claim 22, wherein the analyte comprises an amino group that reacts with the analyte-reactive group.

25. The method of claim 22, wherein the analyte is selected from the group consisting of a peptide, a protein, and a carbohydrate.

26. The method of claim 22, wherein the solid phase is a porous solid phase.

27. The method of claim 22, wherein the solid phase is a gel.

28. A solid phase reagent for simultaneously capturing and fluorescently monolabeling an analyte having multiple reactive sites, comprising a solid phase and a plurality of moieties tethered to the solid phase, wherein each moiety of the plurality of moieties comprises:

(a) a single analyte-reactive group for capturing an analyte to provide a captured analyte having a gyration radius, (b) a single fluorescent group, and (c) a single cleavable anchor group, wherein the analyte-reactive group is covalently attached to the fluorescent group either directly or indirectly, and wherein any two analyte-reactive groups of the plurality of moieties are separated by a distance greater than the gyration radius of the captured analyte;

the fluorescent group is covalently attached to the cleavable anchor group either directly or through a first spacer; and the cleavable anchor group is covalently attached to the solid phase either directly or through a second spacer, and wherein the cleavable anchor group is a 1,3-dioxolane selected from the group consisting of

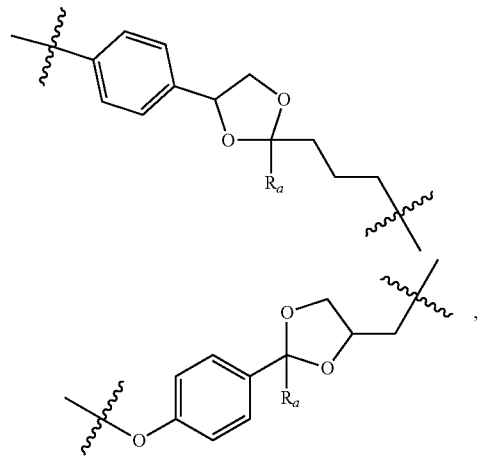

and wherein $R_a$ is selected from the group consisting of (a) H and (b) $CH_3$.

29. The solid phase reagent of claim 28, wherein the solid phase comprises a functional group selected from the group consisting of epoxy, carboxylic acid, hydroxyl, and combinations thereof.

30. The solid phase reagent of claim 28, wherein the solid phase is a 2-hydroxyethylmethacrylate-based monolith solid phase.

31. The solid phase reagent of claim 28, wherein the fluorescent group is selected from the group consisting of:

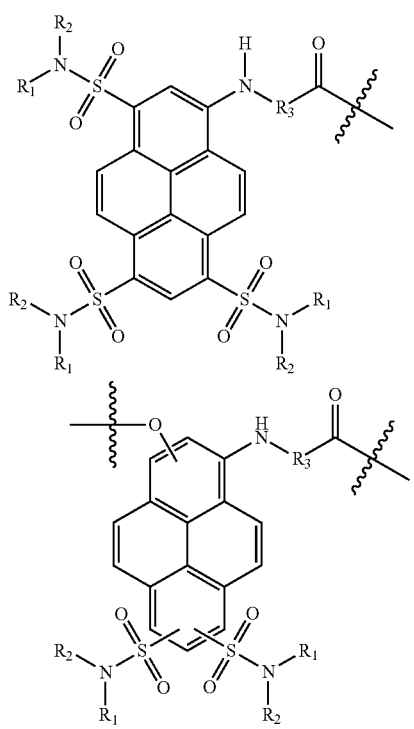

and wherein:

$R_1$, independently at each occurrence, is hydrogen, alkyl$_{C1-12}$, or hetero(backbone)alkyl$_{C1-12}$, wherein when substituted, at least one hydrogen atom of the alkyl$_{C1-12}$, or hetero(backbone)alkyl$_{C1-12}$ moiety is replaced with a functional group carrying a net zero, net negative, or net positive charge;

$R_2$, independently at each occurrence, is hydrogen, alkyl$_{C1-12}$, or hetero(backbone)alkyl$_{C1-12}$, wherein when substituted, at least one hydrogen atom of the alkyl$_{C1-12}$, or hetero(backbone)alkyl$_{C1-12}$ moiety is replaced with a functional group carrying a net zero, net negative, or net positive charge; and $R_3$ is divalent alkyl$_{C1-12}$ or divalent hetero(backbone)alkyl$_{C1-12}$.

32. The solid phase reagent of claim 31, wherein the functional group is a carboxylate, a sulfonate, a sulfate, a primary amino group, a secondary amino group, or a tertiary amino group.

33. The solid phase reagent of claim 28, wherein the fluorescent group is selected from:

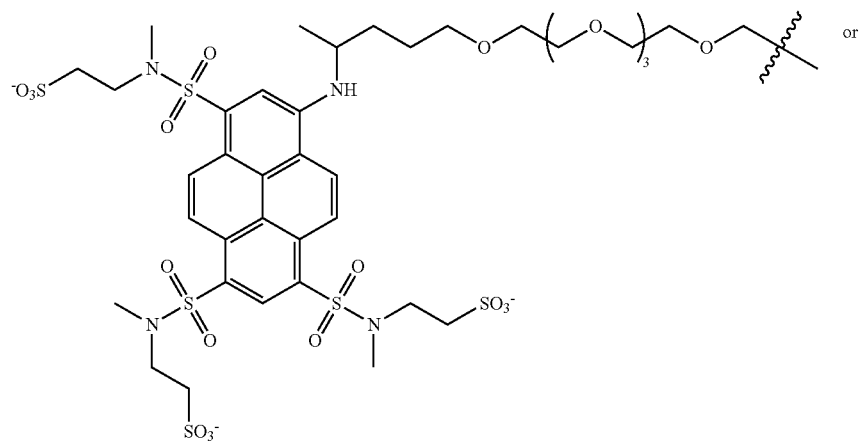

or

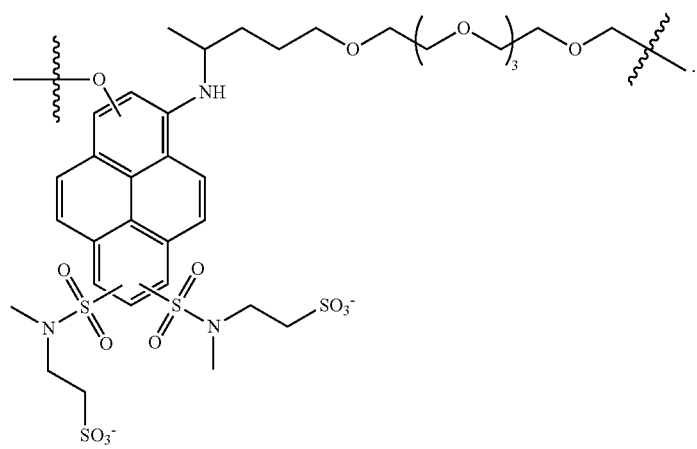

34. The solid phase reagent of claim 28, wherein the analyte-reactive group is an amine-reactive group.

35. The solid phase reagent of claim 28, wherein the solid phase is selected from the group consisting of a particle-based porous solid phase, a monolith porous solid phase, and a gel.

36. The solid phase reagent of claim 28, wherein the first spacer, the second spacer, or both comprise an oligo(oxyethylene) group with a mer-number between 1 and 100.

37. A method of simultaneously immobilizing and fluorescently monolabeling an analyte having multiple reactive sites in an analyte-containing solution, comprising:
(a) contacting an analyte having multiple reactive sites with a solid phase reagent of claim 28;
(b) reacting the analyte with the analyte-reactive group of the solid phase reagent to provide an immobilized monolabeled analyte;
(c) reacting any analyte-reactive group of the solid phase reagent not reacted with the analyte with a quencher to provide quenched analyte-reactive groups;
(d) releasing the immobilized monolabeled analyte and quenched analyte-reactive groups from the solid phase by cleaving the cleavable anchor group to provide a monolabeled analyte; and
(e) isolating or analyzing the monolabeled analyte.

38. The method of claim 37 further comprising analyzing the monolabeled analyte by a method selected from the group consisting of capillary electrophoresis, liquid chromatography, absorption spectroscopy, fluorescence spectroscopy, mass spectrometry, and combinations thereof.

39. The method of claim 37, wherein the analyte comprises an amino group that reacts with the analyte-reactive group.

40. The method of claim 37, wherein the analyte is selected from the group consisting of a peptide, a protein, and a carbohydrate.

41. The method of claim 37, wherein the solid phase is a porous solid phase.

42. The method of claim 37, wherein the solid phase is a gel.

43. A solid phase reagent having the formula:
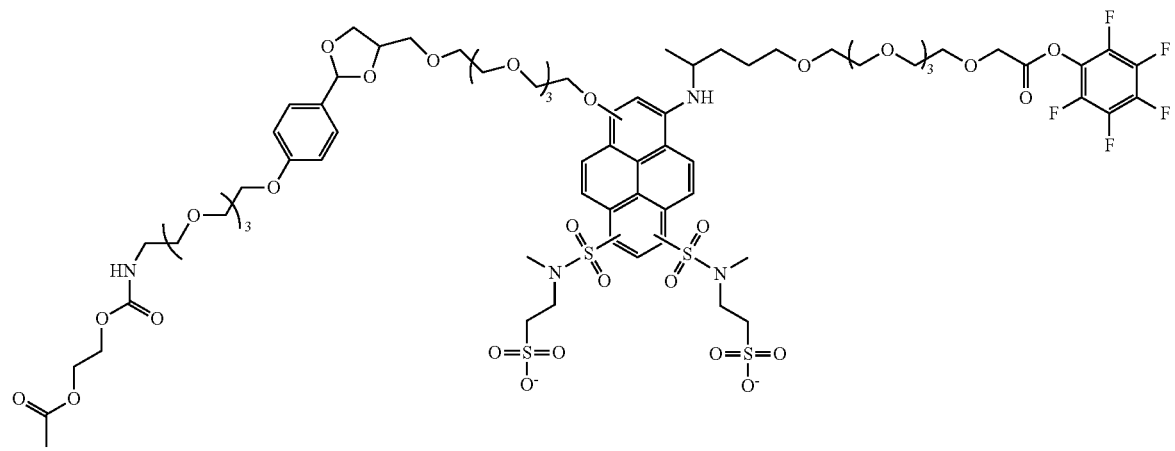
wherein the "Solid Phase" is selected from the group consisting of a porous solid and a gel.
* * * * *